US008546793B2

(12) United States Patent
Kim et al.

(10) Patent No.: US 8,546,793 B2
(45) Date of Patent: Oct. 1, 2013

(54) ORGANIC LIGHT-EMITTING DEVICE

(75) Inventors: Young-Kook Kim, Yongin (KR); Seok-Hwan Hwang, Yongin (KR); Hye-Jin Jung, Yongin (KR); Jin-O Lim, Yongin (KR); Jong-Hyuk Lee, Yongin (KR)

(73) Assignee: Samsung Display Co., Ltd. (KR)

( * ) Notice: Subject to any disclaimer, the term of this patent is extended or adjusted under 35 U.S.C. 154(b) by 208 days.

(21) Appl. No.: 13/078,853

(22) Filed: Apr. 1, 2011

(65) Prior Publication Data

US 2012/0097925 A1 Apr. 26, 2012

(30) Foreign Application Priority Data

Oct. 26, 2010 (KR) ........................ 10-2010-0104734
Mar. 29, 2011 (KR) ........................ 10-2011-0028213

(51) Int. Cl.
*H01L 51/00* (2006.01)

(52) U.S. Cl.
USPC 257/40; 257/103; 257/E51.018; 257/E51.026; 257/E51.028; 548/417; 548/445; 548/447; 428/690

(58) Field of Classification Search
USPC .................... 257/40, 103, E51.018, E51.026, 257/E51.028; 548/417, 445, 447; 428/690
See application file for complete search history.

(56) References Cited

U.S. PATENT DOCUMENTS

| | | | | |
|---|---|---|---|---|
| 5,635,308 | A | 6/1997 | Inoue et al. | |
| 5,972,247 | A | 10/1999 | Shi et al. | |
| 6,465,115 | B2 | 10/2002 | Shi et al. | |
| 6,596,415 | B2 | 7/2003 | Shi et al. | |
| 8,115,200 | B2 * | 2/2012 | Meng et al. | 257/40 |
| 8,247,089 | B2 * | 8/2012 | Otsu et al. | 428/690 |
| 2007/0023749 | A1 | 2/2007 | Hwang et al. | |
| 2008/0012475 | A1 | 1/2008 | Oyamada et al. | |
| 2008/0049413 | A1 | 2/2008 | Jinde et al. | |
| 2008/0203905 | A1 | 8/2008 | Je et al. | |
| 2009/0096356 | A1 | 4/2009 | Murase et al. | |
| 2011/0049478 | A1 * | 3/2011 | Meng et al. | 257/40 |

FOREIGN PATENT DOCUMENTS

| | | | |
|---|---|---|---|
| JP | 8-12600 | A | 1/1996 |
| JP | 2000-003782 | A | 1/2000 |
| JP | 2008-078362 | A | 4/2008 |
| JP | 2010-073987 | | 4/2010 |
| KR | 10-2006-0117038 | A | 11/2006 |
| KR | 10-2007-0003586 | A | 1/2007 |
| KR | 10-2007-0093401 | A | 9/2007 |
| KR | 10-2009-0042272 | A | 4/2009 |
| KR | 10-2010-0108924 | | 10/2010 |
| WO | WO 2010/114264 | A3 | 10/2010 |

OTHER PUBLICATIONS

Official Action issued by the Korean Industrial Property Office dated Feb. 23, 2013, 4 pages.

* cited by examiner

*Primary Examiner* — Tu-Tu Ho
(74) *Attorney, Agent, or Firm* — Knobbe Martens Olson & Bear LLP

(57) ABSTRACT

A heterocyclic compound represented by Formula 1 below and an organic light-emitting device including the heterocyclic compound:

Formula 1

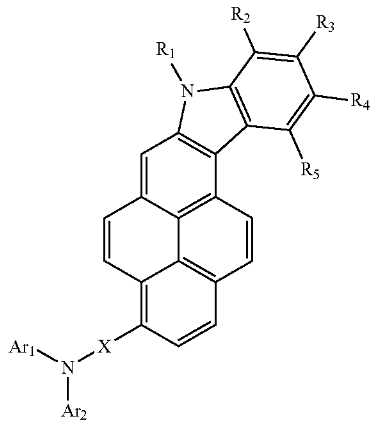

wherein $Ar_1$, $Ar_2$, X, and $R_1$ to $R_5$ are defined as in the specification.

28 Claims, 1 Drawing Sheet

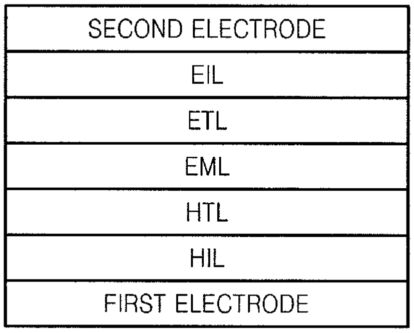
SECOND ELECTRODE
EIL
ETL
EML
HTL
HIL
FIRST ELECTRODE

ORGANIC LIGHT-EMITTING DEVICE

CROSS-REFERENCE TO RELATED APPLICATIONS

This application claims the benefit of Korean Patent Application No. 10-2010-0104734 filed on Oct. 26, 2010 and the benefit of Korean Patent Application No. 10-2011-0028213 filed on Mar. 29, 2011, in the Korean Intellectual Property Office, the disclosure of which is incorporated herein by reference.

BACKGROUND

1. Field

The present embodiments relate to a heterocyclic compound represented by Formula 1 and an organic light-emitting device including the heterocyclic compound.

Formula 1

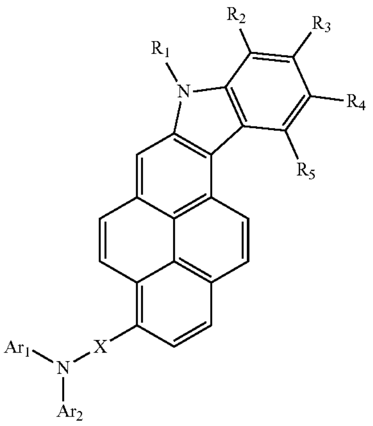

2. Description of the Related Technology

Light-emitting devices are self-emitting display devices and have a wide viewing angle, a high contrast ratio, and a short response time. Due to these characteristics, light-emitting devices are drawing attention.

Such organic light-emitting devices can be roughly classified as either inorganic light-emitting devices that include emission layers containing inorganic compounds, or organic light-emitting devices that include emission layers containing organic compounds.

Organic light-emitting devices have higher luminance, lower driving voltages, and shorter response times than inorganic light-emitting devices, and can render multi-colored displays. Thus, much research into such organic light-emitting devices has been conducted.

Typically, an organic light-emitting device has a stack structure including an anode, a cathode and an organic emission layer interposed therebetween. However, a hole injection layer, a hole transport layer, an electron transport layer, or an electron injection layer may be further stacked between either the anode or the cathode and the organic emission layer. In other words, an organic light-emitting device may have a stack structure of anode/hole transport layer/organic emission layer/cathode or a stack structure of anode/hole transport layer/organic emission layer/electron transport layer/cathode.

As a material for forming the organic emission layer, naphthalene derivatives can be used. However, organic light-emitting devices including such materials may not have satisfactory life span, efficiency, and power consumption characteristics, thereby improvement in this regard still necessary.

SUMMARY OF CERTAIN INVENTIVE ASPECTS

The present embodiments provide a heterocyclic compound having improved electrical characteristics, charge transporting capabilities, light-emission capabilities, and a high glass-transition temperature that is high enough to prevent crystallization.

The present embodiments provide an organic light-emitting device including the heterocyclic compound.

The present embodiments provide a flat panel display device including the organic light-emitting device.

According to an aspect of the present embodiments, there is provided a heterocyclic compound represented by Formula 1 below:

Formula 1

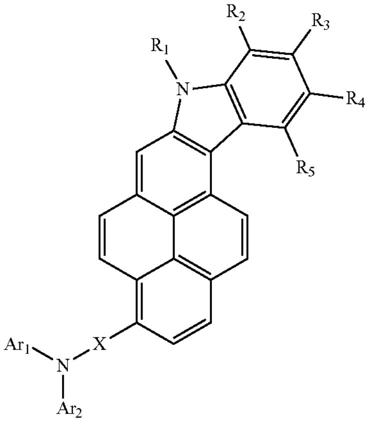

wherein, in Formula 1, $R_1$ through $R_5$ are each independently a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a substituted or unsubstituted $C_5$-$C_{60}$ aryloxy group, a substituted or unsubstituted $C_5$-$C_{60}$ arylthio group, a substituted or unsubstituted $C_5$-$C_{60}$ aryl group, a substituted amino group with a $C_5$-$C_{60}$ aryl or a $C_3$-$C_{60}$ heteroaryl group, a substituted or unsubstituted $C_3$-$C_{60}$ heteroaryl group, a substituted or unsubstituted $C_6$-$C_{60}$ condensed polycyclic group, a halogen atom, a cyano group, a nitro group, a hydroxyl group, or a carboxyl group;

$Ar_1$ and $Ar_2$ are each independently a substituted or unsubstituted $C_3$-$C_{50}$ cycloalkyl group, a substituted or unsubstituted $C_5$-$C_{60}$ aryloxy group, a substituted or unsubstituted $C_5$-$C_{60}$ arythio group, a substituted or unsubstituted $C_5$-$C_{60}$ aryl group, a substituted amino group with a $C_5$-$C_{60}$ aryl or $C_3$-$C_{60}$ heteroaryl group, a substituted or unsubstituted $C_3$-$C_{60}$ heteroaryl group, or a substituted or unsubstituted $C_6$-$C_{60}$ condensed polycyclic group; and X is a divalent linking group represented by $-(Ar_3)_n-$ where $Ar_3$ is a substituted or unsubstituted $C_5$-$C_{60}$ arylene group, a substituted or unsubstituted $C_3$-$C_{60}$ heteroarylene group, or a substituted or unsubstituted $C_6$-$C_{60}$ condensed polycyclic group, and n is an integer from 1 to 10, wherein n groups of $Ar_3$ are identical to or different from each other, and at least two adjacent groups of the n $Ar_3$ groups are fused or linked to each other by a single bond.

In Formula 1 above, $R_1$ to $R_5$ may be each independently a hydrogen atom, a deuterium atom, a cyano group, a halogen atom, an unsubstituted $C_1$-$C_{20}$ alkyl group, a substituted $C_1$-$C_{20}$ alkyl group with at least one fluorine (—F) substituent, a substituted or unsubstituted $C_5$-$C_{20}$ aryl group, or a substituted or unsubstituted $C_3$-$C_{20}$ heteroaryl group.

In Formula 1 above, $R_1$ to $R_5$ may be each independently a hydrogen atom, a deuterium atom, a halogen atom, a cyano group, a substituted or unsubstituted $C_1$-$C_{20}$ alkyl group, or groups represented by Formulae 2a to 21 below:

formula 2a

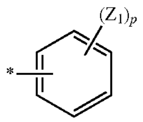

formula 2b

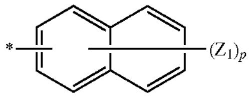

formula 2c

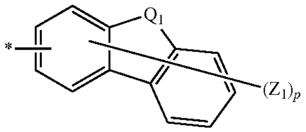

formula 2d

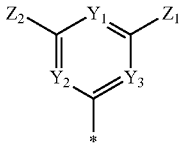

formula 2e

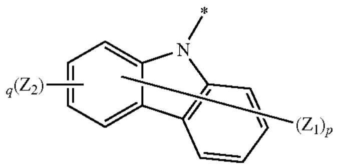

formula 2f

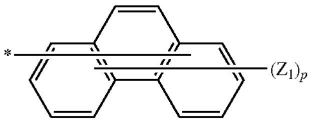

formula 2g

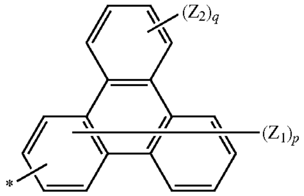

formula 2h

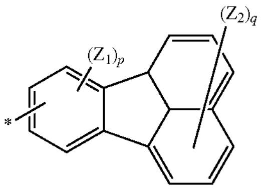

-continued formula 2i

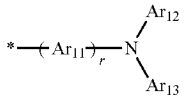

wherein, in Formulae 2a to 2i, $Q_1$ is a linking group represented by —$C(R_6)(R_7)$—, —$N(R_6)$—, —S—, or —O—;

$Y_1$, $Y_2$, and $Y_3$ are each independently a linking group represented by —N= or —$C(R_8)$=;

$Z_1$, $Z_2$, $Ar_{12}$, $Ar_{13}$, $R_6$, $R_7$, and $R_8$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group;

$Ar_{11}$ is a substituted or unsubstituted $C_1$-$C_{20}$ alkylene group, a substituted or unsubstituted $C_5$-$C_{20}$ arylene group, or a substituted or unsubstituted $C_3$-$C_{20}$ heteroarylene group;

p is an integer from 1 to 12;

q is an integer from 1 to 12;

r is an integer from 0 to 5; and

* indicates a binding site.

According to an embodiment, in Formula 1 above, $R_1$ to $R_5$ may be each independently a hydrogen atom, a deuterium atom, a halogen atom, a cyano group, a methyl group, an ethyl group, a propyl group, a butyl group, a pentyl group, or groups represented by Formulae 3a to 31 below:

formula 3a

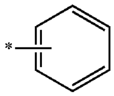

formula 3b

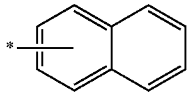

formula 3c

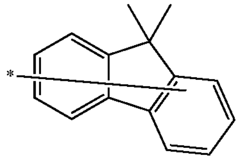

formula 3d

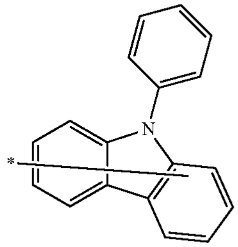

formula 3e

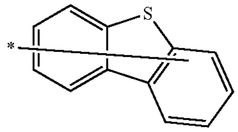

-continued formula 3f

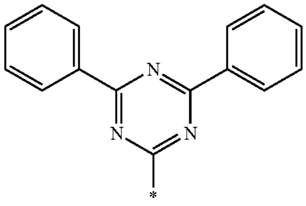

formula 3g

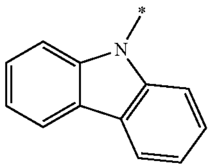

formula 3h

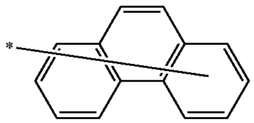

formula 3i

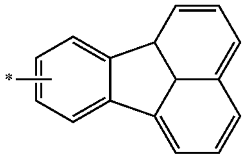

formula 3j

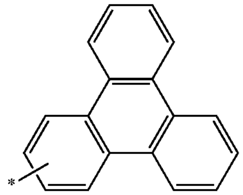

formula 3k

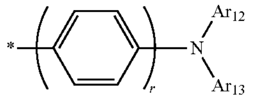

formula 3l

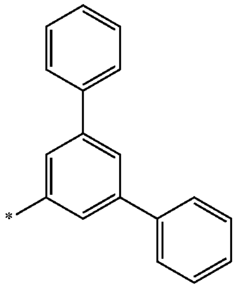

wherein in Formula 3a to 31, $Ar_{12}$ and $Ar_{13}$ are each independently an unsubstituted aryl group, a substituted or unsubstituted $C_3$-$C_{20}$ heteroaryl group, or a substituted or unsubstituted $C_6$-$C_{20}$ condensed polycyclic group;

r is an integer from 0 to 2; and

* indicates a binding site.

According to an embodiment, in Formula 1 above, $R_2$ and $R_5$ may be hydrogen atoms; and $R_1$, $R_3$, and $R_4$ may be each independently a hydrogen atom, a deuterium atom, a halogen atom, a cyano group, a methyl group, an ethyl group, a propyl group, a butyl group, a pentyl group, or groups represented by Formulae 3a to 31 below:

formula 3a

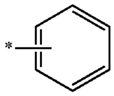

formula 3b

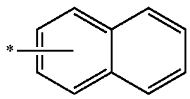

formula 3c

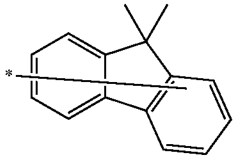

formula 3d

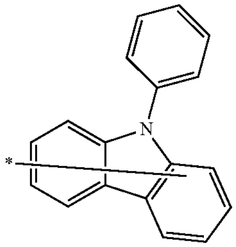

formula 3e

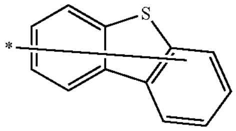

formula 3f

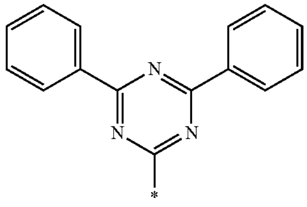

formula 3g

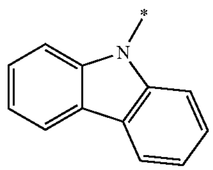

formula 3h

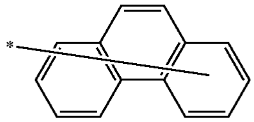

formula 3i

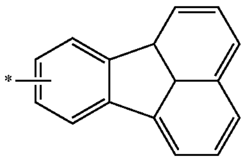

-continued formula 3j

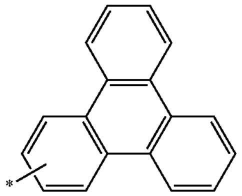

formula 3k

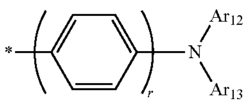

formula 3l

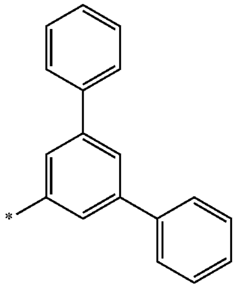

wherein, in Formula 3a to 31, $Ar_{12}$ and $Ar_{13}$ are each independently an unsubstituted aryl group, a substituted or unsubstituted $C_3$-$C_{20}$ heteroaryl group, or a substituted or unsubstituted $C_6$-$C_{20}$ condensed polycyclic group; r is an integer from 0 to 2; and * indicates a binding site.

In Formula 1 above, $R_2$ and $R_5$ may be hydrogen atoms, and $R_1$ may be a substituted or unsubstituted $C_6$-$C_{20}$ aryl group or a substituted or unsubstituted $C_3$-$C_{20}$ heteroaryl group, $R_3$ may be a hydrogen atom or a substituted or unsubstituted $C_6$-$C_{20}$ aryl group, and $R_4$ may be a hydrogen atom or an amino group substituted with a $C_3$-$C_{20}$ heteroaryl group.

In Formula 1 above, $Ar_1$ and $Ar_2$ may be each independently a substituted or unsubstituted $C_1$-$C_{20}$ alkyl group, a substituted or unsubstituted $C_5$-$C_{20}$ aryl group, or a substituted or unsubstituted $C_3$-$C_{20}$ heteroaryl group.

In Formula 1 above, $Ar_1$ and $Ar_2$ may be each independently a group represented by one of Formulae 4a to 4d below:

formula 4a

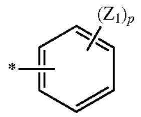

formula 4b

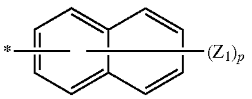

formula 4c

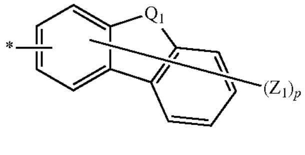

-continued formula 4d

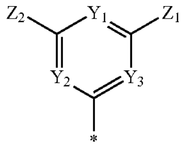

wherein, in Formula 4a to 4d, $Q_1$ is a linking group represented by —C($R_6$)($R_7$)—, —N($R_6$)—, —S—, or —O—;

$Y_1$, $Y_2$, and $Y_3$ are each independently a linking group represented by —N= or —C($R_8$)=;

$Z_1$, $Z_2$, $R_6$, $R_7$, and $R_8$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group;

p is an integer from 1 to 8; and

* indicates a binding site.

In Formula 1 above, $Ar_1$ and $Ar_2$ may be each independently a group represented by one of Formulae 5a to 51 below:

formula 5a

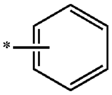

formula 5b

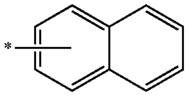

formula 5c

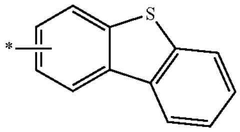

formula 5d

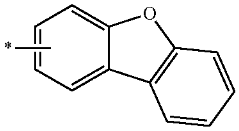

formula 5e

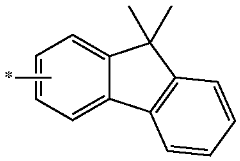

formula 5f

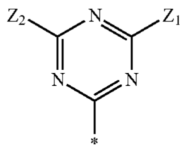

formula 5g

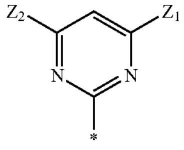

-continued formula 5h

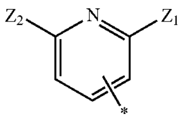

formula 5i

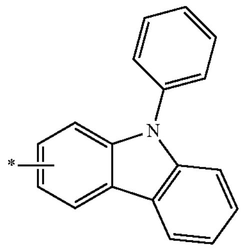

wherein $Z_1$ and $Z_2$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, or a substituted or unsubstituted $C_6$-$C_{20}$ condensed polycyclic group; and * indicates a binding site.

$Ar_3$ for X in Formula 1 may be a substituted or unsubstituted $C_5$-$C_{20}$ arylene group, a substituted or unsubstituted $C_3$-$C_{20}$ heteroarylene group, or a substituted or unsubstituted $C_6$-$C_{20}$ condensed polycyclic group.

$Ar_3$ for X in Formula 1 may include a group represented by one of Formulae 6a to 6e below:

formula 6a

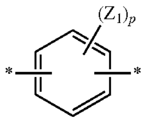

formula 6b

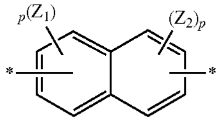

formula 6c

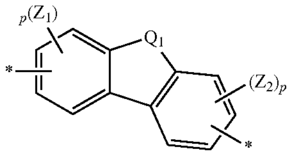

formula 6d

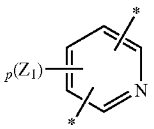

formula 6e

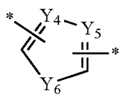

wherein, in Formula 6a to 6e, $Q_1$ is a linking group represented by —C($R_6$)($R_7$)—, —N($R_6$)—, or —S—;

$Y_4$, $Y_5$, and $Y_6$ are each independently a linking group represented by —N= or —C($R_8$)=, —S—, or —O—;

$Z_1$, $Z_2$, $R_6$, $R_7$, and $R_8$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group;

p is an integer from 1 to 8;

q is an integer from 1 to 8; and

* indicates a binding site.

In Formula 1 above, n may be 1 or 2.

In Formula 1, X may include a group represented by one of Formulae 7a to 7j:

forlmua 7a

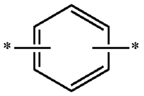

forlmua 7b

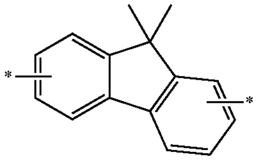

forlmua 7c

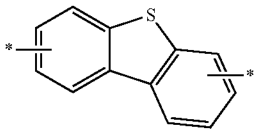

forlmua 7d

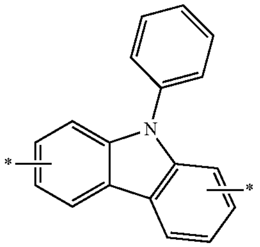

forlmua 7e

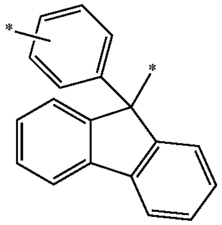

forlmua 7f

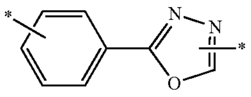

forlmua 7g

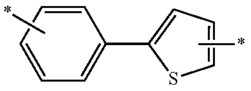

forlmua 7h

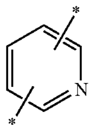

-continued forlmua 7i

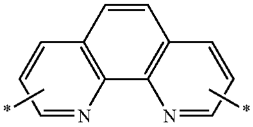

forlmua 7j

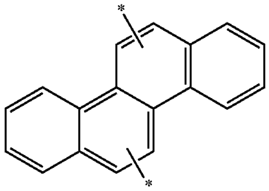

wherein, in Formula 7a to 7j, * indicates a binding site.

In Formula 1 above, $R_1$, $R_3$, and $R_4$ may be each independently a hydrogen atom, a deuterium atom, a halogen atom, a cyano group, a methyl group, an ethyl group, a propyl group, a butyl group, a pentyl group, or groups represented by Formulae 3a to 3l below:

formula 3a

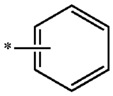

formula 3b

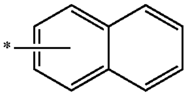

formula 3c

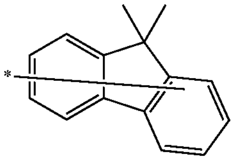

formula 3d

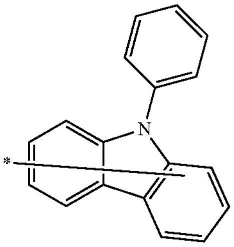

formula 3e

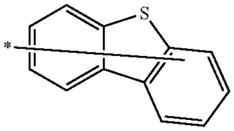

formula 3f

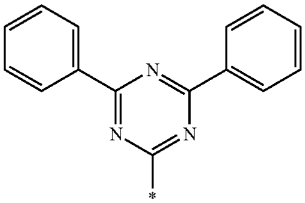

-continued formula 3g

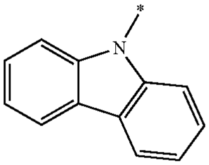

formula 3h

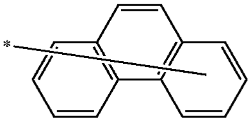

formula 3i

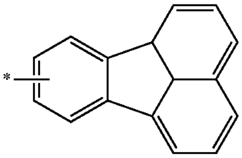

formula 3j

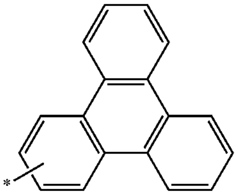

formula 3k

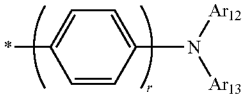

formula 3l

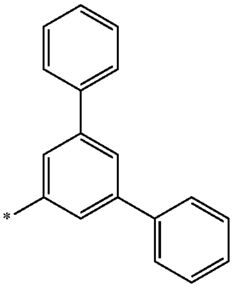

wherein, in Formula 3a to 3l, $Ar_{12}$ and $Ar_{13}$ are each independently an unsubstituted aryl group, a substituted or unsubstituted $C_3$-$C_{20}$ heteroaryl group, or a substituted or unsubstituted $C_6$-$C_{20}$ condensed polycyclic group; r is an integer from 0 to 2, and * indicates a binding site;

$R_2$ and $R_5$ are hydrogen atoms;

$Ar_3$ comprises a group represented by one of Formulae 6a to 6e below:

formula 6a

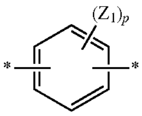

-continued formula 6b

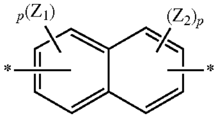

formula 6c

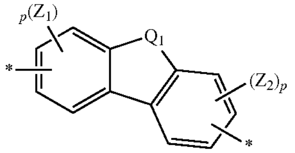

formula 6d

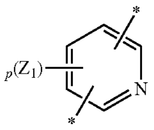

formula 6e

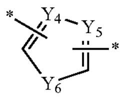

wherein, in Formulae 6a to 6e, $Q_1$ is a linking group represented by —$C(R_6)(R_7)$—, —$N(R_6)$—, or —S—; $Y_4$, $Y_5$ and $Y_6$ are each independently a linking group represented by —N═, —$C(R_8)$═, —S—, or —O—; $Z_1$, $Z_2$, $R_6$, $R_7$, and $R_8$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group; p is an integer from 1 to 8; q is an integer from 1 to 8; and * indicates a binding site;

n in Formula 1 is 1 or 2; and $Ar_1$ and $Ar_2$ are each independently selected from among groups represented by Formulae 4a to 4d below:

formula 4a

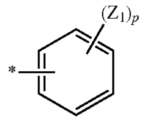

formula 4b

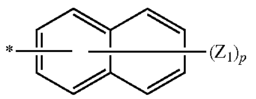

formula 4c

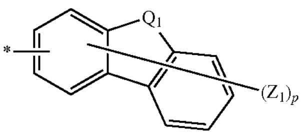

formula 4d

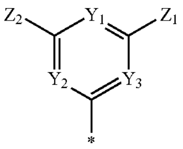

wherein, in Formulae 4a to 4d, $Q_1$ is a linking group represented by —$C(R_6)(R_7)$—, —$N(R_6)$—, —S—, or —O—; $Y_1$, $Y_2$ and $Y_3$ are each independently a linking group represented by —N═ or —$C(R_8)$═; $Z_1$, $Z_2$, $R_6$, $R_7$, and $R_8$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group; p is an integer from 1 to 8; and * indicates a binding site.

The heterocyclic compound may include one of the compounds below:

2

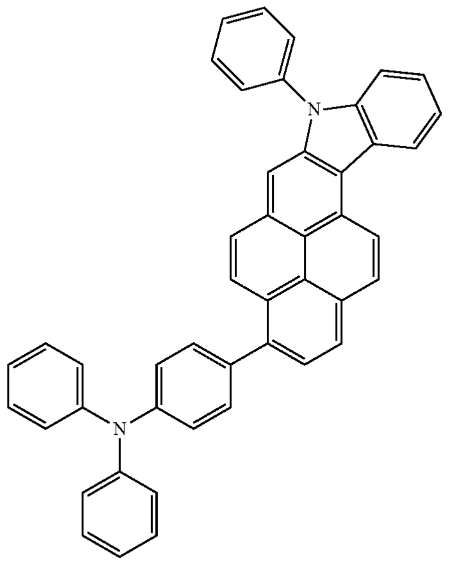

11

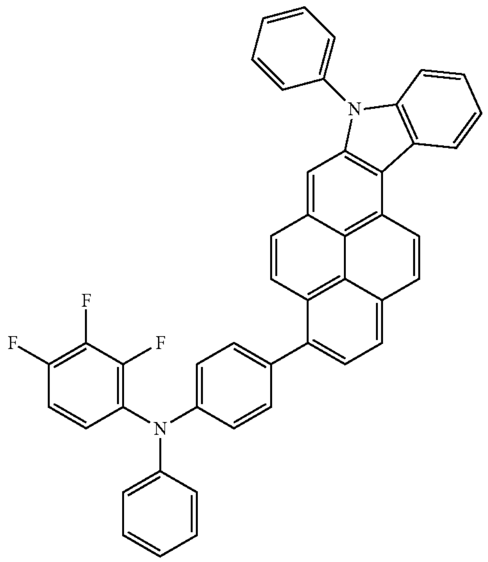

-continued
24
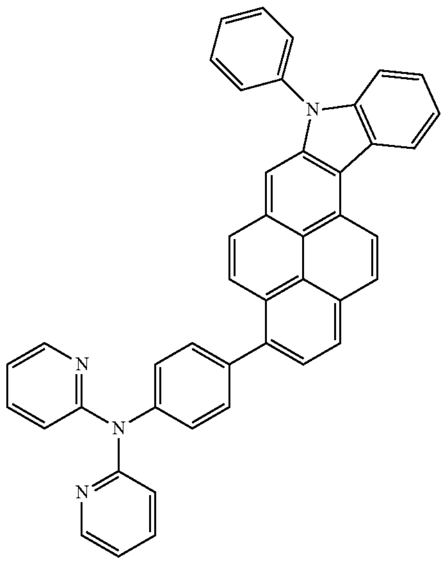
34
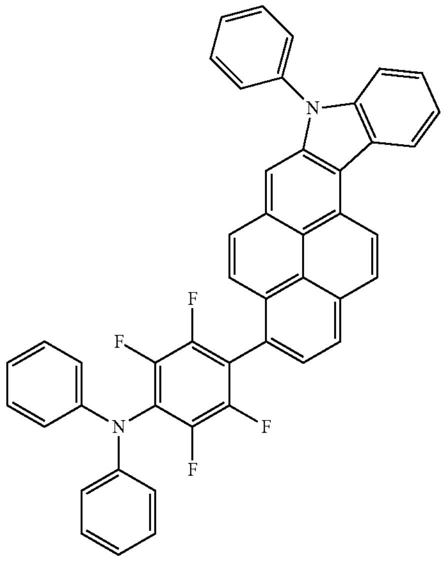
-continued
45
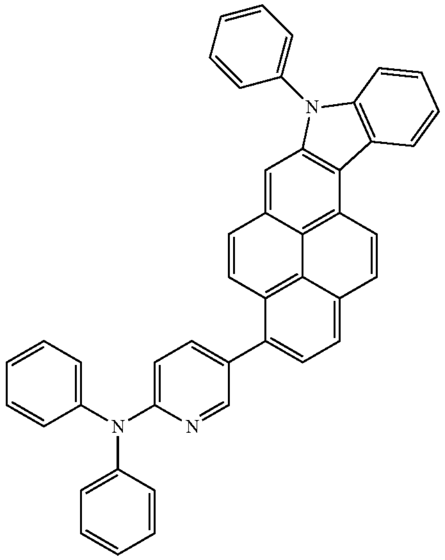
48
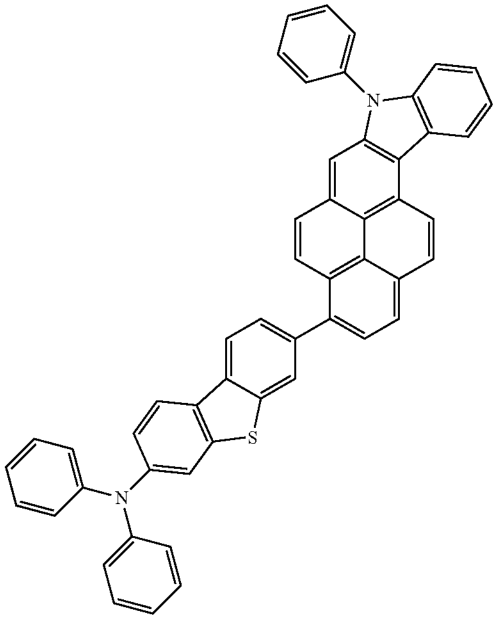

-continued

55

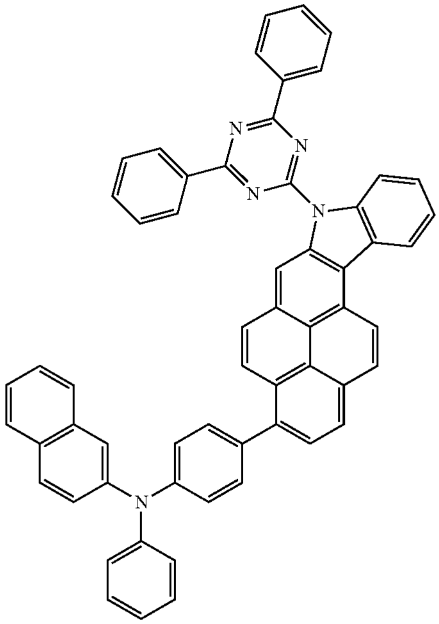

57

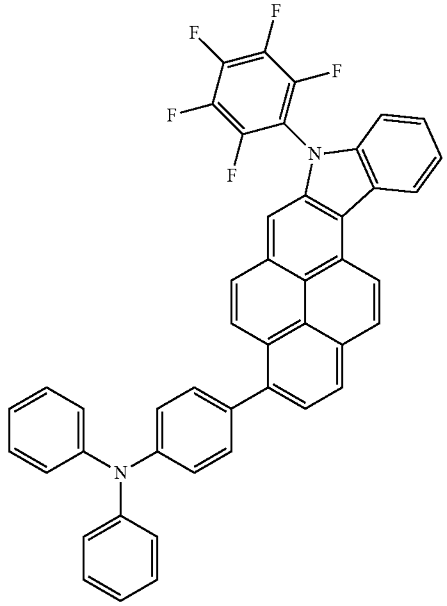

-continued

73

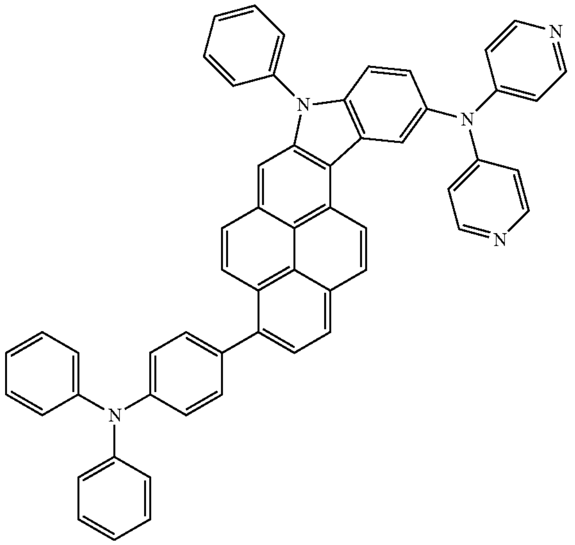

82

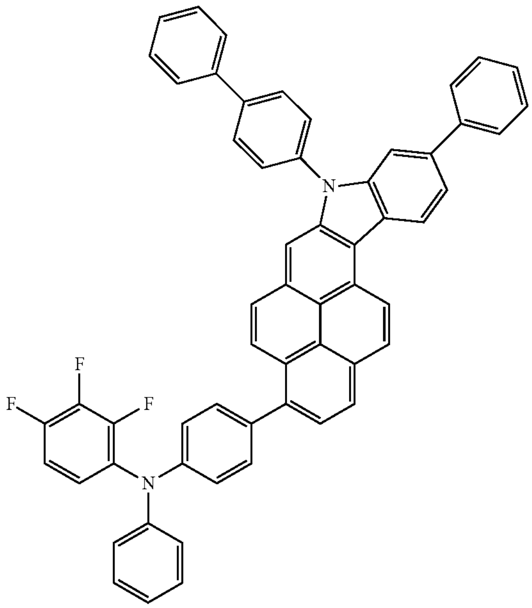

According to another aspect of the present embodiments, an organic light-emitting device includes: a first electrode; a second electrode; and an organic layer between the first electrode and the second electrode, wherein the organic layer includes a first layer including a heterocyclic compound above.

The first layer may include at least one layer a hole injection layer, a hole transport layer, a functional layer having both hole injection and hole transport capabilities, an electron injection layer, an electron transport layer, a functional layer having both electron injection and electron transport capabilities or any combination thereof.

The first layer may include an emission layer, and the heterocyclic compound of Formula 1 may be used in the emission layer as a host or a dopant for a fluorescent or phosphorescent device.

The first layer may include an emission layer. The emission layer may further include an anthracene compound, an arylamine compound, or a styryl compound.

The first layer may include an emission layer. A red layer, a green layer, a blue layer, and a white layer of the emission layer may further include a phosphorescent compound.

The first layer may include a blue emission layer.

The first layer may include a blue emission layer, and the heterocyclic compound of Formula 1 may be used as a blue dopant.

The organic layer of the organic light-emitting device may include a hole injection layer, a hole transport layer, a functional layer having hole injecting and transporting capabilities, an emission layer, a hole blocking layer, an electron transport layer, an electron injecting layer, or a combination of two or more layers thereof.

At least one layer selected from the hole injection layer, the hole transport layer, or the functional layer having hole injecting and transporting capabilities may further include a charge-generating material.

The electron transport layer of the organic light-emitting device may include an electron transporting organic material and a metal-containing material.

The metal-containing material may further include a Li complex.

The first layer may be formed using a wet process by using a heterocyclic compound according to an embodiment of the present invention.

According to another aspect of the present embodiments, a flat panel display device includes the organic light-emitting device according to the one or more embodiments described above, wherein the first electrode of the organic light-emitting device may be electrically connected to a source electrode or a drain electrode of a thin-film transistor.

BRIEF DESCRIPTION OF THE DRAWINGS

The above and other features and advantages of the present embodiments will become more apparent by describing in detail example embodiments thereof with reference to the attached drawing in which:

FIG. 1 illustrates the structure of an organic light-emitting device according to an embodiment.

DETAILED DESCRIPTION OF CERTAIN INVENTIVE EMBODIMENTS

An organic light-emitting device manufactured using a compound of phenylanthracene dimer or trimer as an organic emission layer material is widely known. However, such organic light-emitting devices have a narrow energy gap and lower blue-light color purity since two or three oligomeric species of anthracene are linked by conjugation. In addition, such compounds are highly vulnerable to oxidation and thus are liable to produce impurities, necessitating purification. In order to overcome these drawbacks, organic light-emitting devices manufactured using an anthracene compound including naphthalene substituted for anthracene at 1,9 positions or using a diphenylanthracene compound including an aryl group substituted for a phenyl group at m-position have been introduced. However, these organic light-emitting devices have a lower light-emission efficiency.

Organic light-emitting devices may also be manufactured using nathphalene-substituted monoanthracene derivatives. However, the light-emission efficiency thereof is low at about 1 cd/A, and thus such organic light-emitting devices are not suitable for practical use.

Furthermore, organic light-emitting devices may be manufactured using phenylanthracene compounds including aryl substituents at m-position. Such a compound has excellent thermal resistance but leads to an unsatisfactorily low light-emission efficiency of about 2 cd/A.

The present embodiments will now be described more fully with reference to the accompanying drawings, in which example embodiments are shown.

A heterocyclic compound according to an embodiment is represented by Formula 1 below:

Formula 1

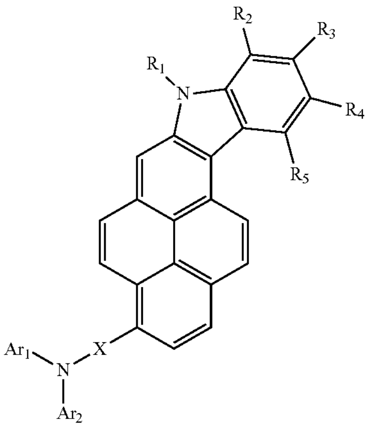

In Formula 1, $R_1$ through $R_5$ are each independently a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a substituted or unsubstituted $C_5$-$C_{60}$ aryloxy group, a substituted or unsubstituted $C_5$-$C_{60}$ arylthio group, a substituted or unsubstituted $C_5$-$C_{60}$ aryl group, a substituted amino group with a $C_5$-$C_{60}$ aryl or $C_3$-$C_{60}$ heteroaryl group, a substituted or unsubstituted $C_3$-$C_{60}$ heteroaryl group, a substituted or unsubstituted $C_6$-$C_{60}$ condensed polycyclic group, a halogen atom, a cyano group, a nitro group, a hydroxyl group, or a carboxyl group;

$Ar_1$ and $Ar_2$ are each independently a substituted or unsubstituted $C_3$-$C_{50}$ cycloalkyl group, a substituted or unsubstituted $C_5$-$C_{60}$ aryloxy group, a substituted or unsubstituted $C_5$-$C_{60}$ arythio group, a substituted or unsubstituted $C_5$-$C_{60}$ aryl group, a substituted amino group with a $C_5$-$C_{60}$ aryl or $C_3$-$C_{60}$ heteroaryl group, a substituted or unsubstituted $C_3$-$C_{60}$ heteroaryl group, or a substituted or unsubstituted $C_6$-$C_{60}$ condensed polycyclic group; and X is a divalent linking group represented by $-(Ar_3)_n-$ where $Ar_3$ is a substituted or unsubstituted $C_5$-$C_{60}$ arylene group, a substituted or unsubstituted $C_3$-$C_{60}$ heteroarylene group, or a substituted or unsubstituted $C_6$-$C_{60}$ condensed polycyclic group, and n is an integer from 1 to 10, wherein n groups of $Ar_3$ may be identical to or different from each other, and at least two adjacent groups of the n $Ar_3$ groups may be fused or linked to each other by a single bond.

In some embodiments the heterocyclic compound of Formula 1 may be used as a light-emitting material, a hole transporting material, or an electron transporting material. The compound of Formula 1 has better performance as a blue emission material than conventional blue emission materials, and thus may be used as a deep blue material for use in a large display having a non-resonance structure. The heterocyclic compound of Formula 1 having a heterocyclic group in the molecules thereof has a high glass transition temperature (Tg)

or a high melting point due to the inclusion of the heterocyclic group. Thus, the heterocyclic compound has high heat resistance against Joule's heat generated in an organic layer, between organic layers, or between an organic layer and a metal electrode when light emission occurs, and has high durability in high-temperature environments.

An organic light-emitting device manufactured using the heterocyclic compound of Formula 1 has high durability when stored or operated. In addition, due to the inclusion of a substituent such as an aryl group or heteroaryl group, molecular layers formed as thin films may be maintained in good condition, thereby improving the characteristics of the organic light-emitting device.

Substituents in the heterocyclic compound of Formula 1 will now be described in detail.

$R_1$ to $R_5$ in Formula 1 above may be each independently a hydrogen atom, a deuterium atom, a cyano group, a halogen atom, an unsubstituted $C_1$-$C_{20}$ alkyl group, a substituted $C_1$-$C_{20}$ alkyl group with at least one fluorine (—F) substituent, a substituted or unsubstituted $C_5$-$C_{20}$ aryl group, or a substituted or unsubstituted $C_3$-$C_{20}$ heteroaryl group.

In some embodiments $R_1$ to $R_5$ in Formula 1 may be each independently a hydrogen atom, a deuterium atom, a halogen atom, a cyano group, a substituted or unsubstituted $C_1$-$C_{20}$ alkyl group, or compounds represented by Formulae 2a to 2i below:

formula 2a

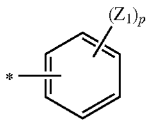

formula 2b

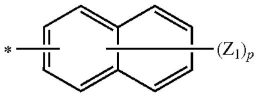

formula 2c

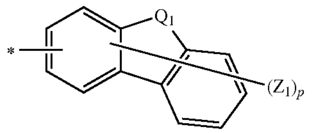

formula 2d

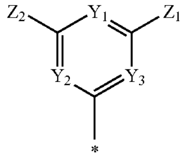

formula 2e

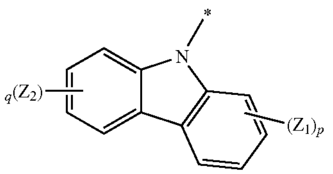

formula 2f

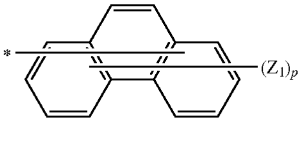

-continued formula 2g

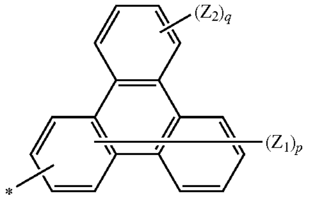

formula 2h

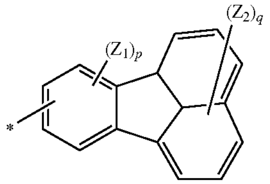

formula 2i

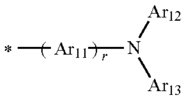

In Formula 2a to 21 above, $Q_1$ is a linking group represented by —C($R_6$)($R_7$)—, —N($R_6$)—, —S—, or —O—; $Y_1$, $Y_2$ and $Y_3$ are each independently a linking group represented by —N= or —C($R_8$)=;

$Z_1$, $Z_2$, $Ar_{12}$, $Ar_{13}$, $R_6$, $R_7$, and $R_8$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group;

$Ar_{11}$ is a substituted or unsubstituted $C_1$-$C_{20}$ alkylene group, a substituted or unsubstituted $C_5$-$C_{20}$ arylene group, or a substituted or unsubstituted $C_3$-$C_{20}$ heteroarylene group;

p is an integer from 1 to 12; q is an integer from 1 to 12; r is an integer from 0 to 5; and * indicates a binding site.

In some embodiments $R_1$ to $R_5$ in Formula 1 above may be each independently a hydrogen atom, a deuterium atom, a halogen atom, a cyano group, a methyl group, an ethyl group, a propyl group, a butyl group, a pentyl group, or compounds represented by Formulae 3a to 31 below:

formula 3a

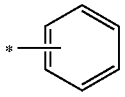

formula 3b

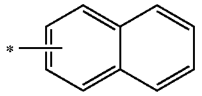

formula 3c

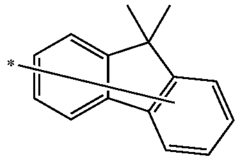

-continued formula 3d

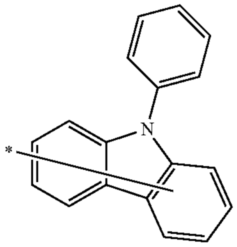

formula 3e

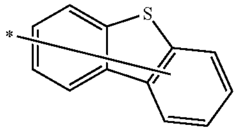

formula 3f

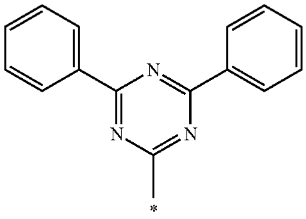

formula 3g

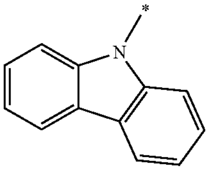

formula 3h

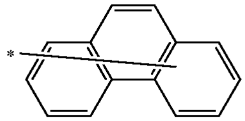

formula 3i

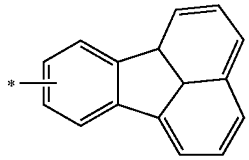

formula 3j

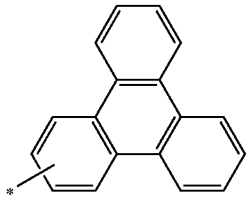

formula 3k

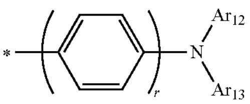

-continued formula 3l

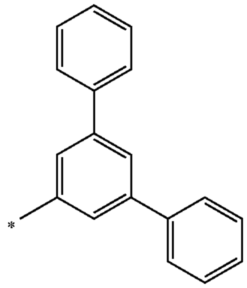

In Formula 3a to 3l above, $Ar_{12}$ and $Ar_{13}$ are each independently an unsubstituted aryl group, a substituted or unsubstituted $C_3$-$C_{20}$ heteroaryl group, or a substituted or unsubstituted $C_6$-$C_{20}$ condensed polycyclic group;

r is an integer from 0 to 2; and

* indicates a binding site.

In some embodiments, $R_2$ and $R_5$ in Formula 1 are hydrogen atoms; and $R_1$, $R_3$, and $R_4$ are each independently a hydrogen atom, a deuterium atom, a halogen atom, a cyano group, a methyl group, an ethyl group, a propyl group, a butyl group, a pentyl group, or groups represented by Formulae 3a to 3l below:

formula 3a

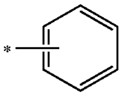

formula 3b

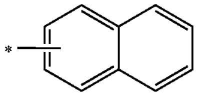

formula 3c

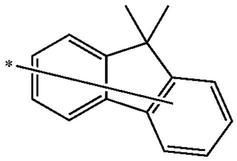

formula 3d

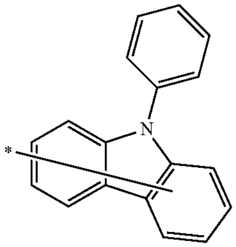

formula 3e

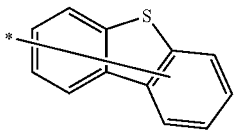

-continued formula 3f

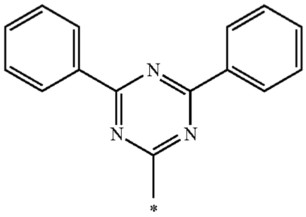

formula 3g

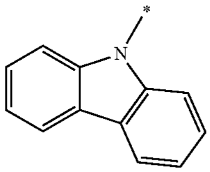

formula 3h

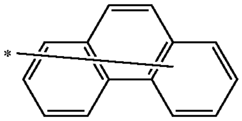

formula 3i

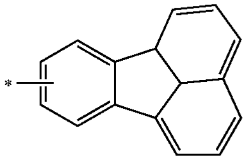

formula 3j

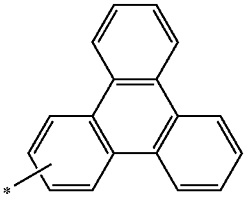

formula 3k

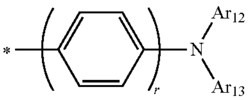

formula 3l

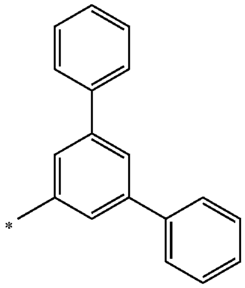

In Formula 3a to 3l above, $Ar_{12}$ and $Ar_{13}$ are each independently an unsubstituted aryl group, a substituted or unsubstituted $C_3$-$C_{20}$ heteroaryl group, or a substituted or unsubstituted $C_6$-$C_{20}$ condensed polycyclic group;

r is an integer from 0 to 2; and

* indicates a binding site.

In other embodiments, $R_2$ and $R_5$ may be hydrogen atoms, and $R_1$ may be a substituted or unsubstituted $C_6$-$C_{20}$ aryl group or a substituted or unsubstituted $C_3$-$C_{20}$ heteroaryl group, $R_3$ may be a hydrogen atom or a substituted or unsubstituted $C_6$-$C_{20}$ aryl group, and $R_4$ may be a hydrogen atom or an amino group with a $C_3$-$C_{20}$ heteroaryl group.

In some embodiments $Ar_1$ and $Ar_2$ in Formula 1 above may be each independently a substituted or unsubstituted $C_1$-$C_{20}$ alkyl group, a substituted or unsubstituted $C_5$-$C_{20}$ aryl group, or a substituted or unsubstituted $C_3$-$C_{20}$ heteroaryl group.

In some other embodiments $Ar_1$ and $Ar_2$ in Formula 1 above may be each independently a compound represented by Formulae 4a to 4d below:

formula 4a

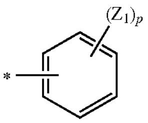

formula 4b

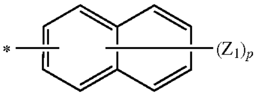

formula 4c

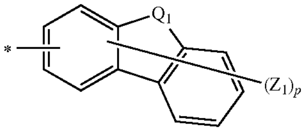

formula 4d

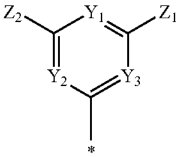

In Formulae 4a to 4d, $Q_1$ is a linking group represented by —$C(R_6)(R_7)$—, —$N(R_6)$—, —S—, or —O—; $Y_1$, $Y_2$, and $Y_3$ are each independently a linking group represented by —N= or —$C(R_8)$=; $Z_1$, $Z_2$, $R_6$, $R_7$, and $R_8$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group; p is an integer from 1 to 8; and * indicates a binding site.

In some embodiments $Ar_1$ and $Ar_2$ in Formula 1 above may be each independently a compound represented by one of Formulae 5a to 5i below:

formula 5a

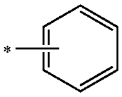

formula 5b

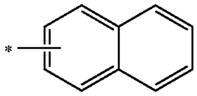

-continued formula 5c

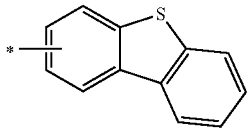

formula 5d

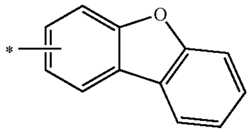

formula 5e

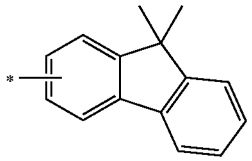

formula 5f

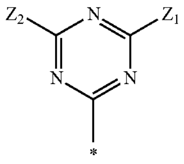

formula 5g

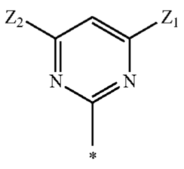

formula 5h

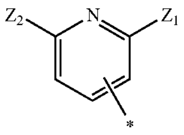

formula 5i

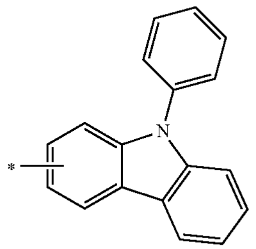

In Formulae 5a to 5i, $Z_1$ and $Z_2$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, or a substituted or unsubstituted $C_6$-$C_{20}$ condensed polycyclic group; and * indicates a binding site.

In some embodiments $Ar_3$ for X in Formula 1 above may be a substituted or unsubstituted $C_5$-$C_{20}$ arylene group, a substituted or unsubstituted $C_3$-$C_{20}$ heteroarylene group, or a substituted or unsubstituted $C_6$-$C_{20}$ condensed polycyclic group.

In some other embodiments $Ar_3$ may be a group represented by one of Formulae 6a to 6e:

formula 6a

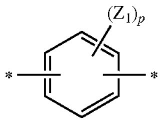

formula 6b

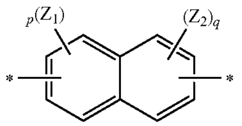

formula 6c

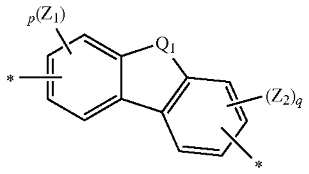

formula 6d

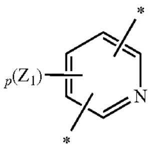

formula 6e

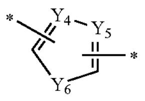

In Formulae 6a to 6e, $Q_1$ is a linking group represented by —$C(R_6)(R_7)$—, —$N(R_6)$—, or —S—;

$Y_4$, $Y_5$, and $Y_6$ are each independently a linking group represented by —N= or —$C(R_8)$=, —S—, or —O—;

$Z_1$, $Z_2$, $R_6$, $R_7$, and $R_8$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group;

p is an integer from 1 to 8; q is an integer from 1 to 8; and

* indicates a binding site.

In some embodiments n indicating the number of $Ar_3$ groups for X in Formula 1 above may be an integer of 1 or 2.

In some embodiments X in Formula 1 above may be a group represented by one of Formulae 7a to 7j:

forlmua 7a

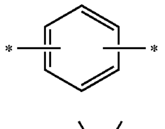

forlmua 7b

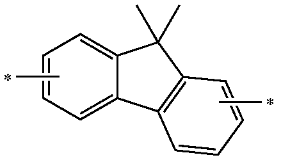

-continued forlmua 7c

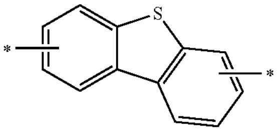

forlmua 7d

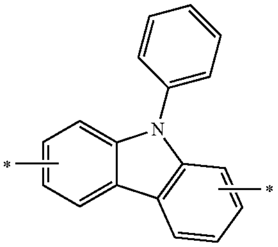

forlmua 7e

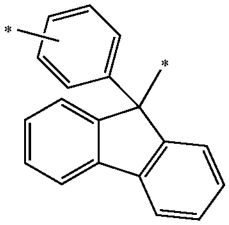

forlmua 7f

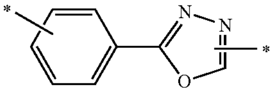

forlmua 7g

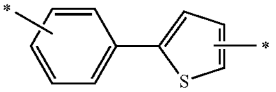

forlmua 7h

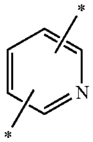

forlmua 7i

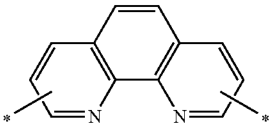

forlmua 7j

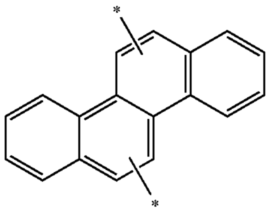

In Formulae 7a to 7j, * indicates a binding site.

In some embodiments $R_1$, $R_3$, and $R_4$ in Formula 1 above may be each independently a hydrogen atom, a deuterium atom, a halogen atom, a cyano group, a methyl group, an ethyl group, a propyl group, a butyl group, a pentyl group, or compounds represented by Formulae 3a to 3l below:

formula 3a

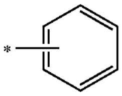

formula 3b

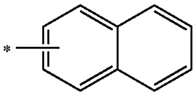

formula 3c

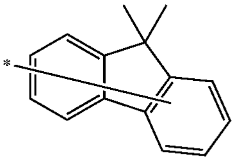

formula 3d

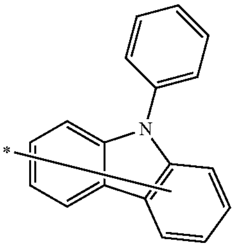

formula 3e

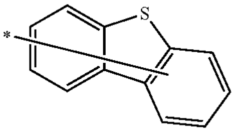

formula 3f

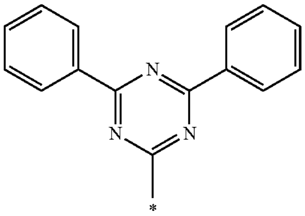

formula 3g

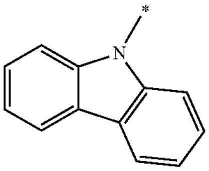

formula 3h

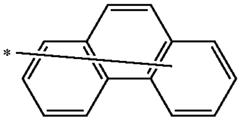

formula 3i

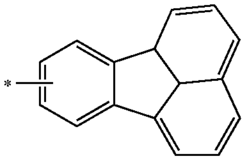

-continued formula 3j

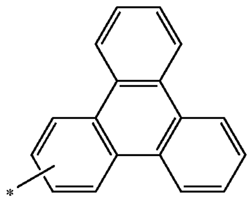

formula 3k

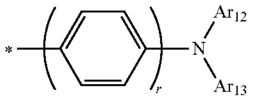

formula 3l

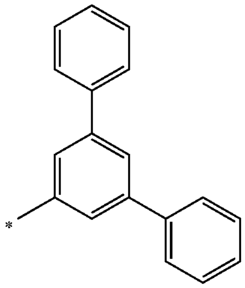

In Formula 3a to 3l above, $Ar_{12}$ and $Ar_{13}$ are each independently an unsubstituted aryl group, a substituted or unsubstituted $C_3$-$C_{20}$ heteroaryl group, or a substituted or unsubstituted $C_6$-$C_{20}$ condensed polycyclic group; r is an integer from 0 to 2, and * indicates a binding site;

$R_2$ and $R_5$ in Formula 1 may be hydrogen atoms;

$Ar_3$ in Formula 1 may be a group represented by one of Formulae 6a to 6e below;

formula 6a

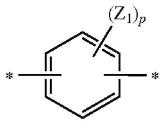

formula 6b

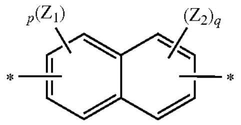

formula 6c

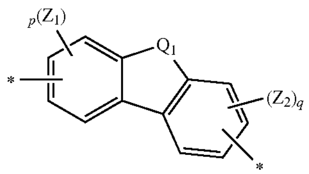

formula 6d

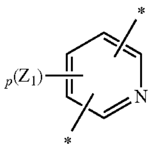

-continued formula 6e

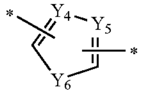

wherein, in Formulae 6a to 6e, $Q_1$ is a linking group represented by —$C(R_6)(R_7)$—, —$N(R_6)$—, or —S—; $Y_4$, $Y_5$ and $Y_6$ are each independently a linking group represented by —N═, —$C(R_8)$═, —S—, or —O—; $Z_1$, $Z_2$, $R_6$, $R_7$, and $R_8$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group; p is an integer from 1 to 8; q is an integer from 1 to 8; and * indicates a binding site;

n, which indicates the number of $Ar_3$ groups for X in Formula 1, may be an integer of 1 or 2;

$Ar_1$ and $Ar_2$ in Formula 1 may be each independently a compound represented by one of Formulae 4a to 4d below:

formula 4a

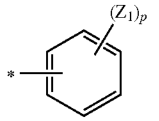

formula 4b

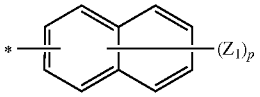

formula 4c

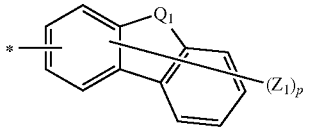

formula 4d

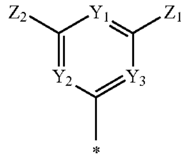

wherein, in Formulae 4a to 4d, $Q_1$ is a linking group represented by —$C(R_6)(R_7)$—, —$N(R_6)$—, —S—, or —O—; $Y_1$, $Y_2$ and $Y_3$ are each independently a linking group represented by —N═ or —$C(R_8)$═; $Z_1$, $Z_2$, $R_6$, $R_7$, and $R_8$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group; p is an integer from 1 to 8; and * indicates a binding site.

Hereinafter, substituents described with reference to formulae used herein will now be described in detail. In this regard, the numbers of carbons in substituents are presented only for illustrative purposes and do not limit the characteristics of the substituents The unsubstituted $C_1$-$C_{50}$ alkyl group used herein may be linear or branched. Examples of the alkyl group may include, but are not limited to, a methyl group, an ethyl group, a propyl group, an isobutyl group, a sec-butyl group, a pentyl group, an iso-amyl group, a hexyl group, a heptyl group, an octyl group, a nonanyl group, and a dodecyl group. At least one hydrogen atom of the alkyl group may be substituted with heavy hydrogen atom, a halogen atom, a hydroxyl group, a nitro group, a cyano group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, or a $C_3$-$C_{16}$ heteroaryl group.

The unsubstituted $C_2$-$C_{60}$ alkenyl group indicates an unsaturated alkyl groups having at least one carbon-carbon double bond in the center or at a terminal of the alkyl group. Examples of the alkenyl group include an ethenyl group, a propenyl group, a butenyl group, and the like. At least one hydrogen atom in the unsubstituted alkenyl group may be substituted with a substituent described above in conjunction with the alkyl group.

The unsubstituted $C_2$-$C_{60}$ alkynyl group indicates an alkyl group having at least one carbon-carbon triple bond in the center or at a terminal of the alkyl group. Examples of the unsubstituted $C_2$-$C_{20}$ alkynyl group include acetylene, propylene, phenylacetylene, naphthylacetylene, isopropylacetylene, t-butylacetylene, diphenylacetylene, and the like. At least one hydrogen atom in the alkynyl group may be substituted with a substituent described above in conjunction with the alkyl group.

The unsubstituted $C_3$-$C_{50}$ cycloalkyl group indicates a $C_3$-$C_{50}$ cyclic alkyl group wherein at least one hydrogen atom in the cycloalkyl group may be substituted with a substituent described above in conduction with the $C_1$-$C_{50}$ alkyl group.

The unsubstituted $C_1$-$C_{50}$ alkoxy group indicates a group having a structure of —OA wherein A is an unsubstituted $C_1$-$C_{50}$ alkyl group as described above. Nonlimiting examples of the unsubstituted $C_1$-$C_{50}$ alkoxy group include a methoxy group, an ethoxy group, a propoxy group, an isopropyloxy group, a butoxy group, and a pentoxy group. At least one hydrogen atom of the alkoxy group may be substituted with a substituent such as those described above in conjunction with the alkyl group.

The unsubstituted $C_5$-$C_{60}$ aryl group indicates a carbocyclic aromatic system containing at least one ring. At least two rings may be fused to each other or linked to each other by a single bond. The term 'aryl' refers to an aromatic system, such as phenyl, naphthyl, or anthracenyl. At least one hydrogen atom in the aryl group may be substituted with a described above with reference to the unsubstituted $C_1$-$C_{50}$ alkyl group.

Examples of the substituted or unsubstituted $C_5$-$C_{60}$ aryl group include, but are not limited to, a phenyl group, a $C_1$-$C_{10}$ alkylphenyl group (for example, ethylphenyl group), a halophenyl group (for example, o-, m-, and p-fluorophenyl group, dichlorophenyl group), a cyanophenyl group, dicyanophenyl group, a trifluoromethoxyphenyl group, a biphenyl group, a halobiphenyl group, a cyanobiphenyl group, a $C_1$-$C_{10}$ alkyl biphenyl group, a $C_1$-$C_{10}$ alkoxybiphenyl group, a o-, m-, and p-toryl group, an o-, m-, and p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a halonaphthyl group (for example, fluoronaphthyl group), a $C_1$-$C_{10}$ alkylnaphthyl group (for example, methylnaphthyl group), a $C_1$-$C_{10}$ alkoxynaphthyl group (for example, methoxynaphthyl group), a cyanonaphthyl group, an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylene group, a pyrenyl group, a chrycenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronelyl group, a trinaphthylenyl group, a heptaphenyl group, a heptacenyl group, a pyranthrenyl group, and an ovalenyl group.

The unsubstituted $C_3$-$C_{60}$ heteroaryl group includes one, two or three hetero atoms selected from N, O, P and S. At least two rings may be fused to each other or linked to each other by a single bond. Examples of the unsubstituted $C_3$-$C_{60}$ heteroaryl group include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazol group, an indol group, a quinolyl group, an isoquinolyl group, and a dibenzothiophene group. In addition, at least one hydrogen atom in the heteroaryl group may be substituted with a substituent described above in conjunction with the unsubstituted $C_1$-$C_{50}$ alkyl group.

The unsubstituted $C_5$-$C_{50}$ aryloxy group is a group represented by $—OA_1$ wherein $A_1$ may be a $C_5$-$C_{50}$ aryl group. An example of the aryloxy group is a phenoxy group. At least one hydrogen atom in the aryloxy group may be substituted with a substituent described above in conjunction with the unsubstituted $C_1$-$C_{50}$ alkyl group.

The unsubstituted $C_5$-$C_{50}$ arylthio group is a group represented by $—SA_1$ where $A_1$ may be a $C_5$-$C_{60}$ aryl group. Nonlimiting examples of the arylthio group include a benzenethio group and a naphthylthio group. At least one hydrogen atom in the arylthio group may be substituted with a substituent described above in conjunction with the unsubstituted $C_1$-$C_{50}$ alkyl group.

The unsubstituted $C_6$-$C_{60}$ condensed polycyclic group refers to a substituent including at least two rings wherein at least one aromatic ring and/or at least one non-aromatic ring are fused to each other. The unsubstituted $C_6$-$C_{60}$ condensed polycyclic group may include some of the substituents described in conjunction with the aryl group or the heteroaryl group.

The following compound is an example of the condensed polycyclic group.

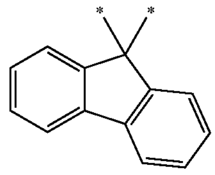

In Formula 1 below, X prevents formation of a resonance structure between a lone pair electron of a moiety B (arylamine part) and a moiety A (pyrene part) since X has a tendency to be perpendicular to the A moiety (pyrene part).

<Formula 1>

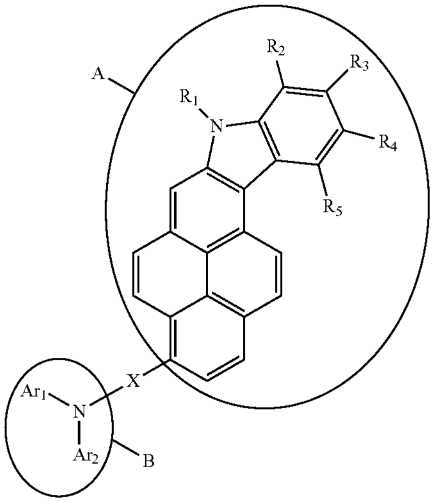

As a result, the compound of Formula 1 emits blue light having high color purity. The blue light emitted from the compound of Formula 1 may be distinguished from a bluish green light that is long-wavelength shifted compared to a conventional blue light.

Also, the compound of Formula 1 has excellent heat resistance, and thus, an organic light-emitting device using the compound may have higher efficiency and longer lifespan.

Examples of the heterocyclic compound represented by Formula 1 may include Compounds 1 through 84 represented by the following formulae. However, the heterocyclic compounds represented by Formula 1 are not limited thereto.

1

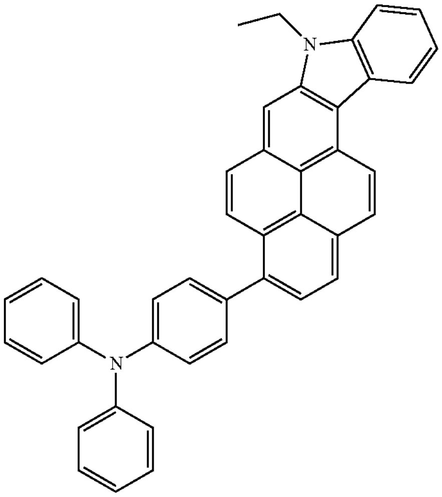

-continued

2

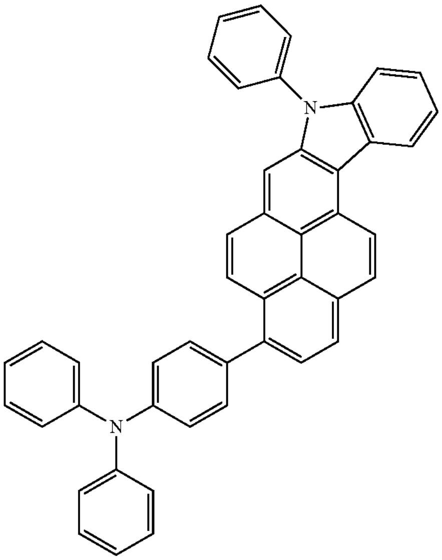

3

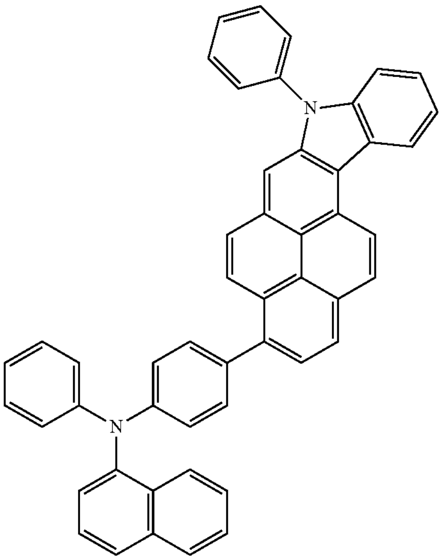

-continued
4
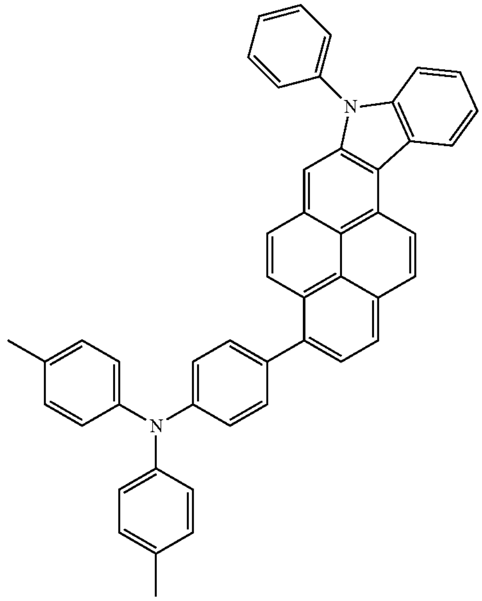
5
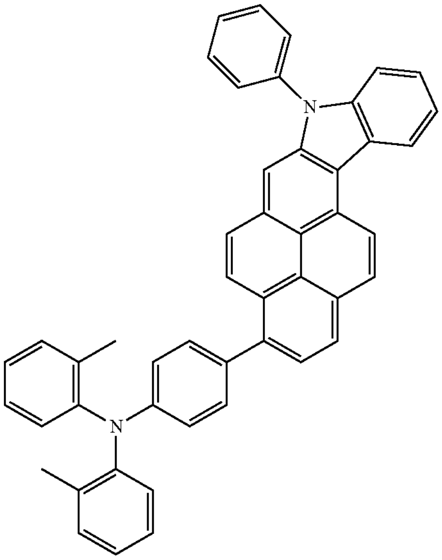
-continued
6
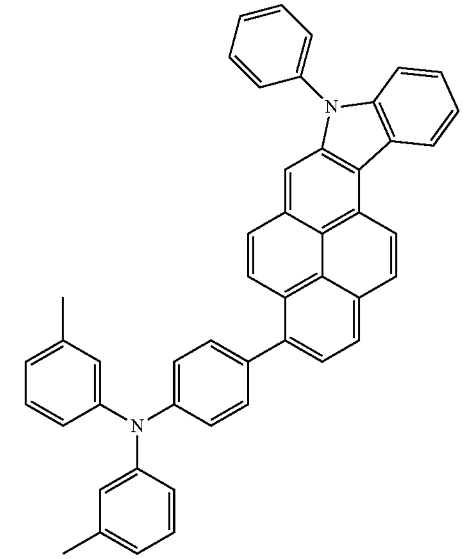
7
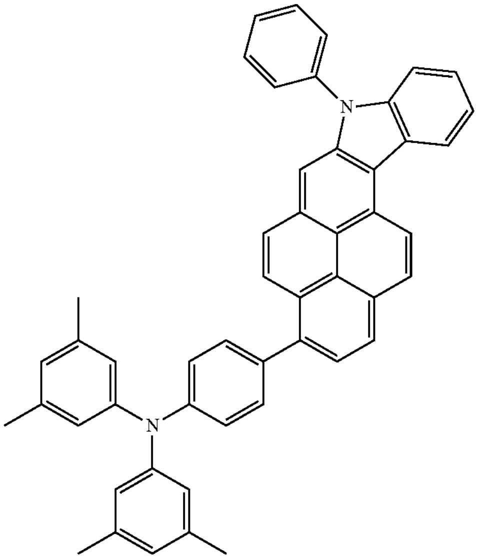

-continued
8
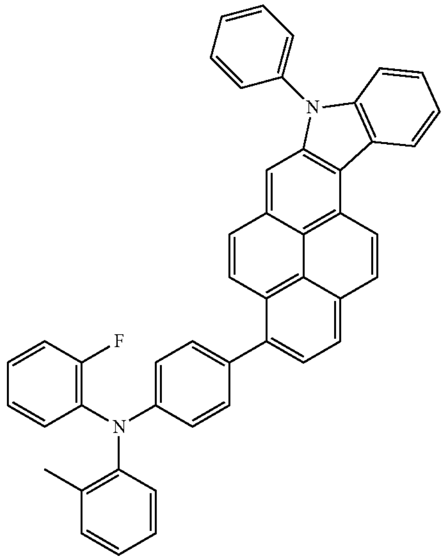
10
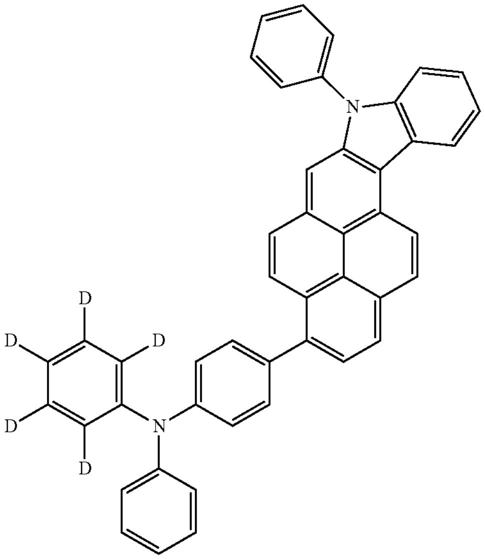
9
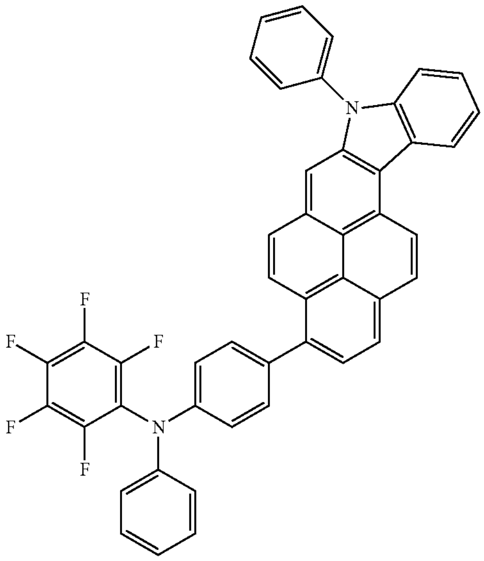
11
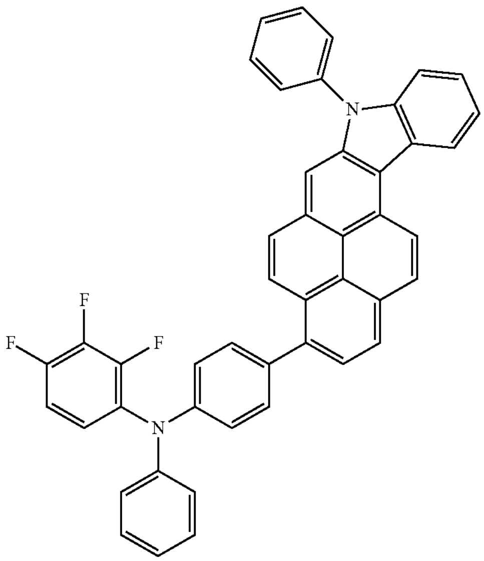

-continued
12
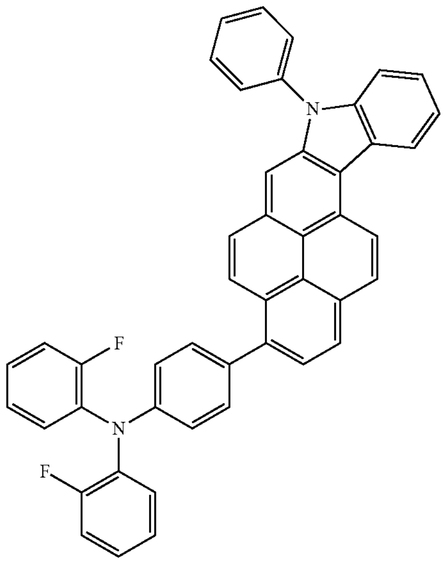
13
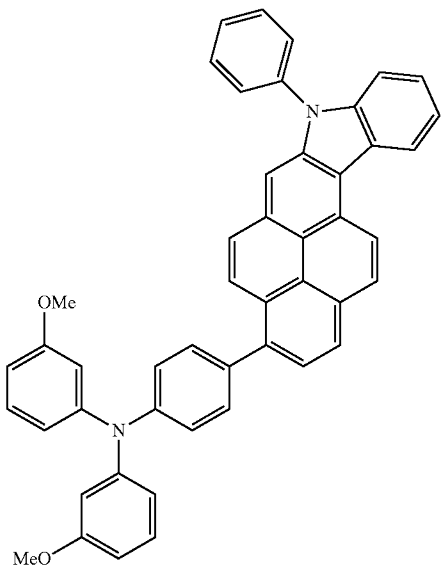
-continued
14
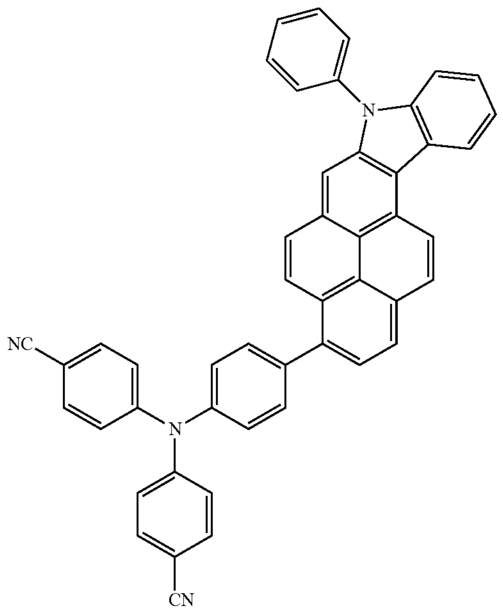
15
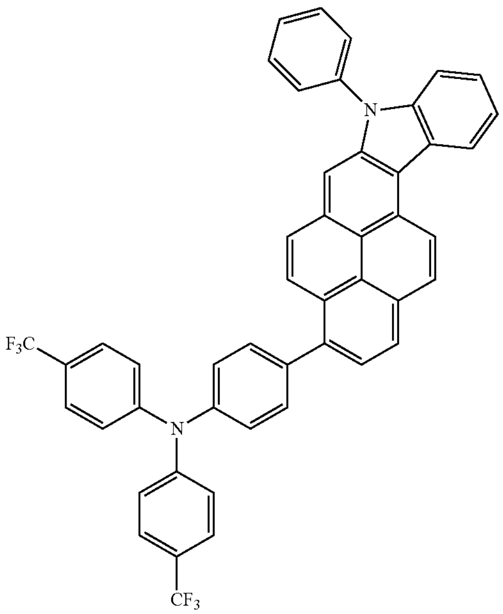

-continued
16
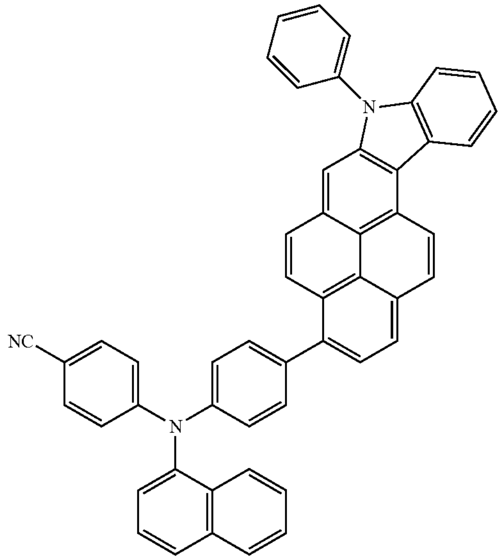
17
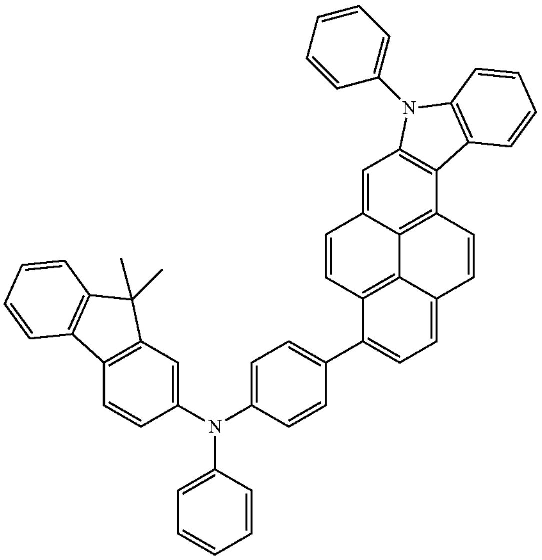
-continued
18
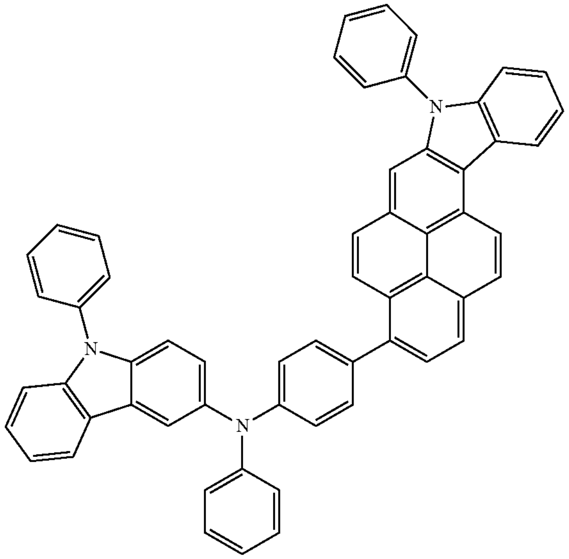
19
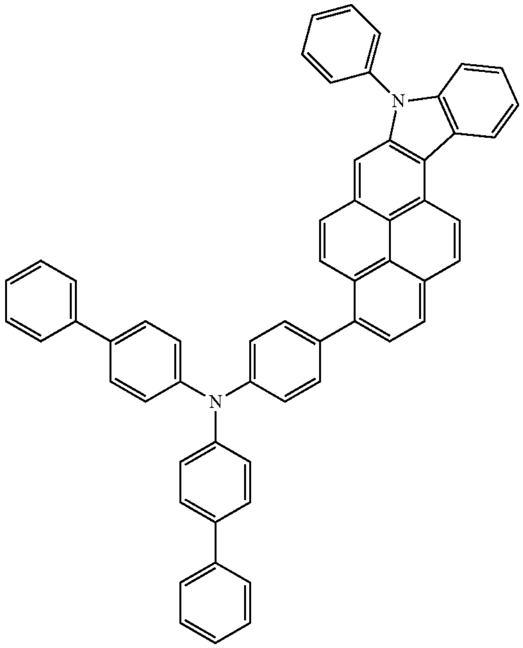

-continued
20
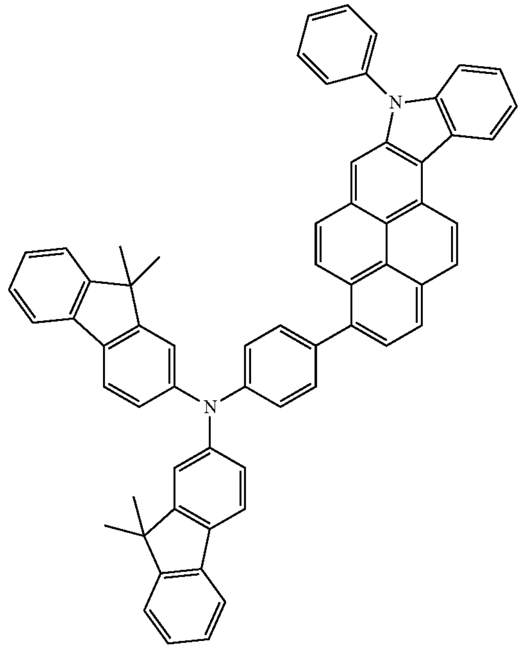
21
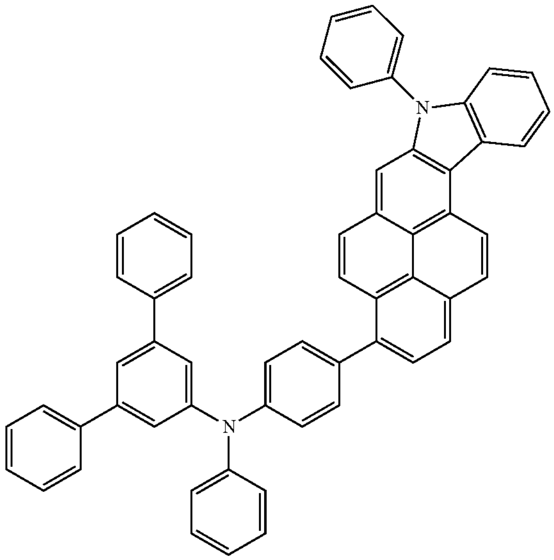
-continued
22
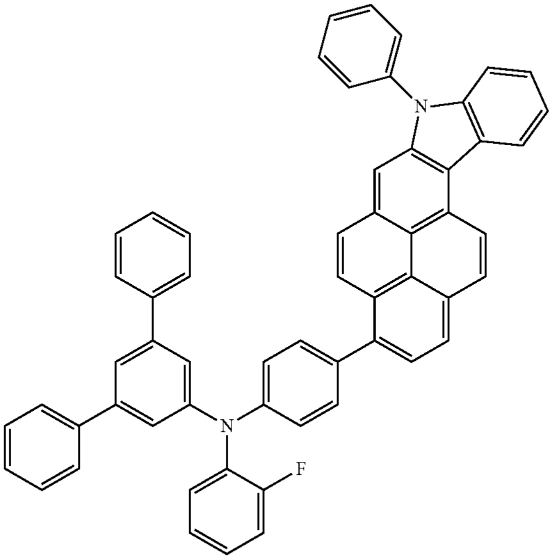
23
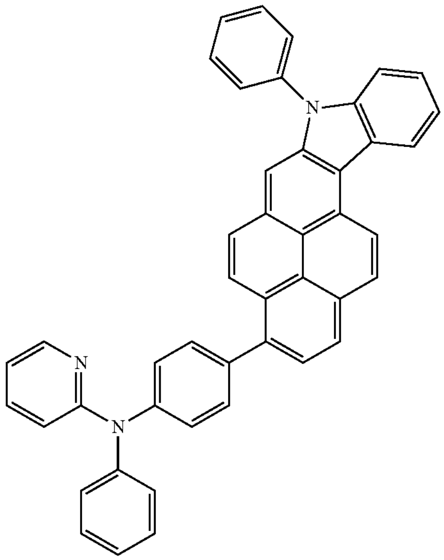

-continued
24
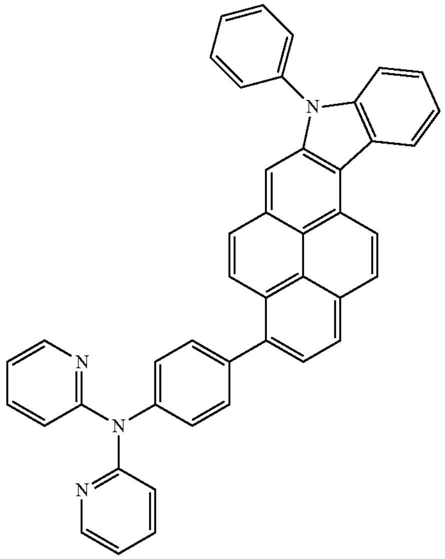
-continued
26
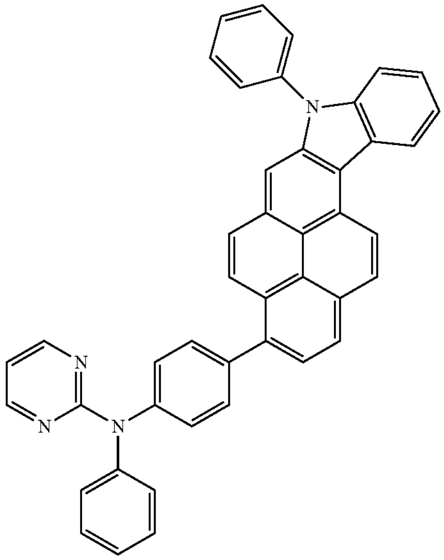
25
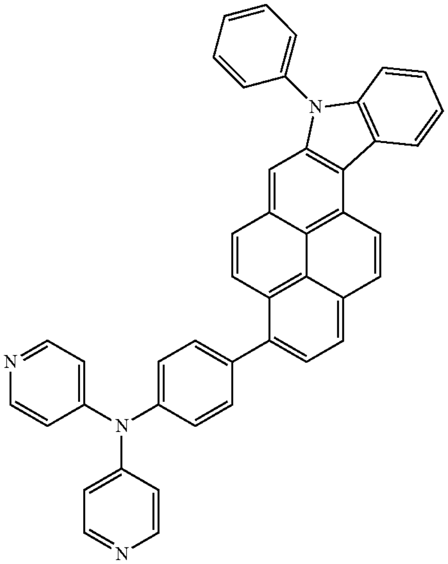
27
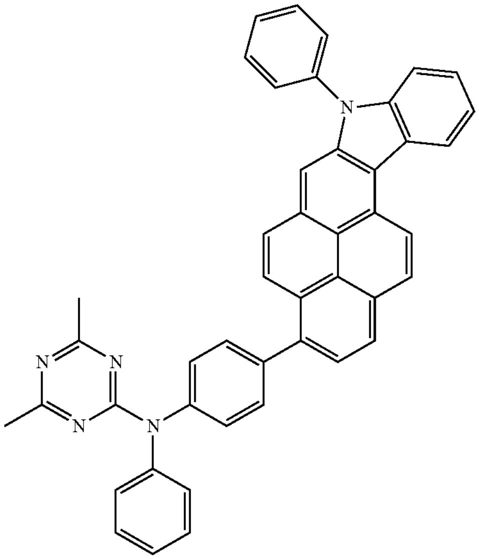

-continued
28
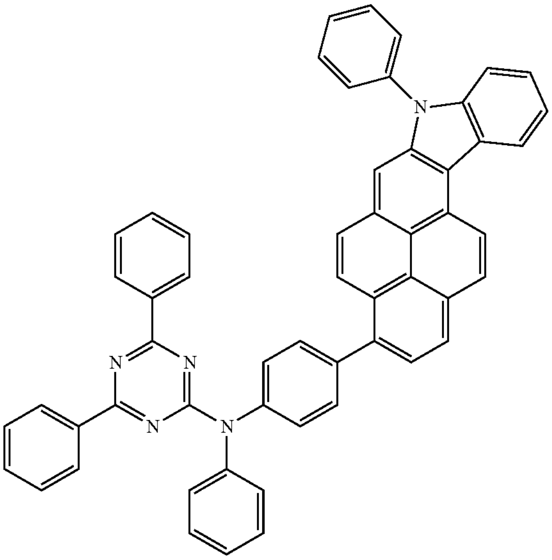
29
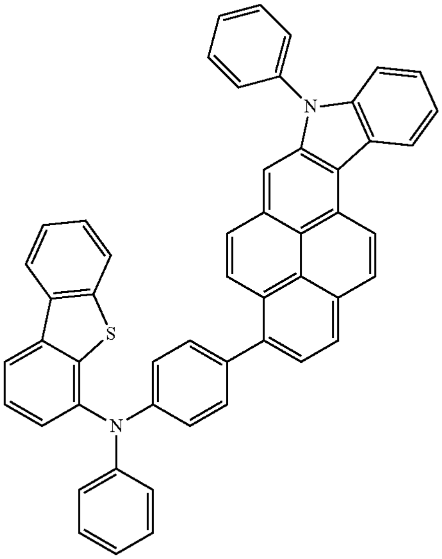
-continued
30
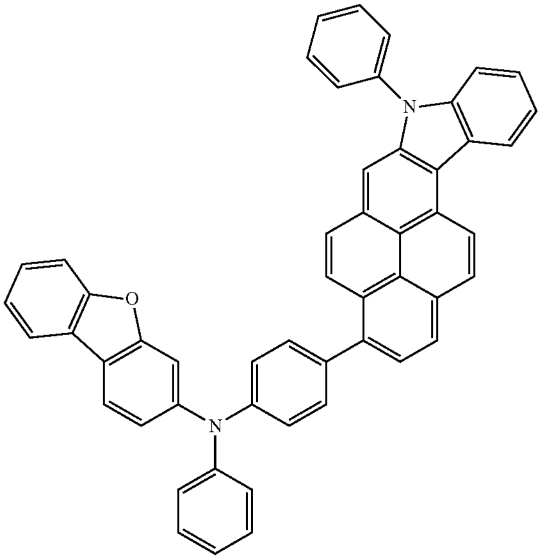
31
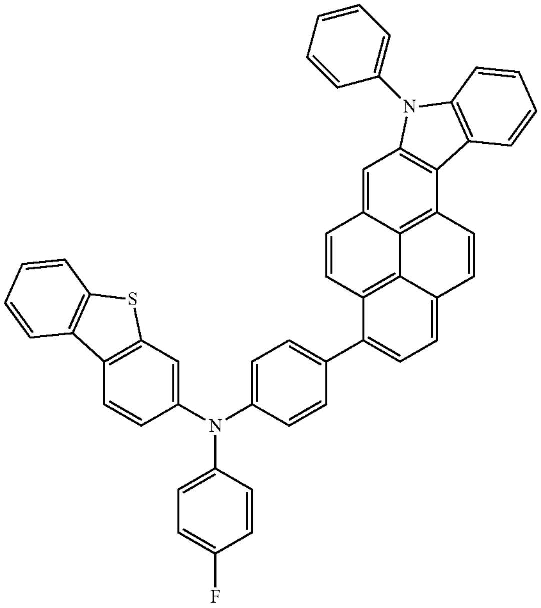

-continued
32
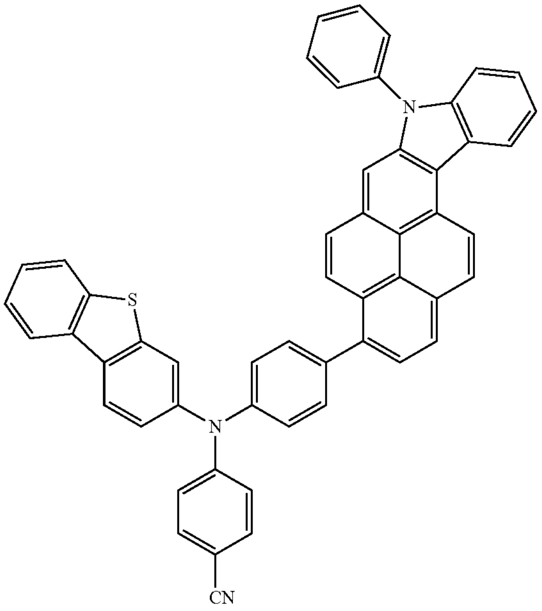
33
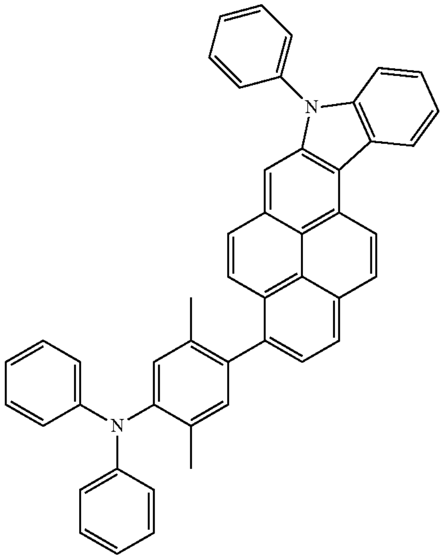
-continued
34
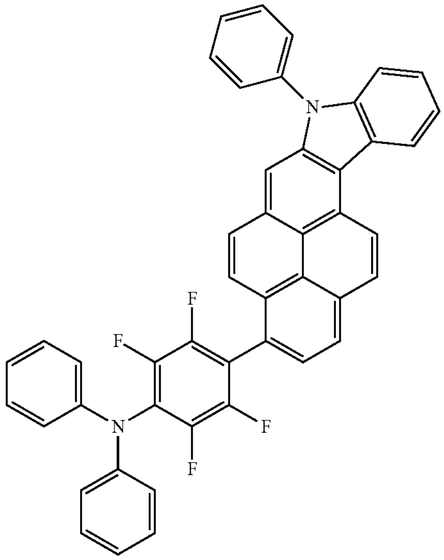
35
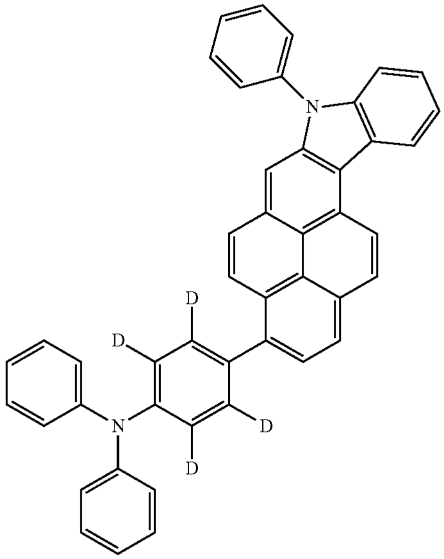

-continued
36
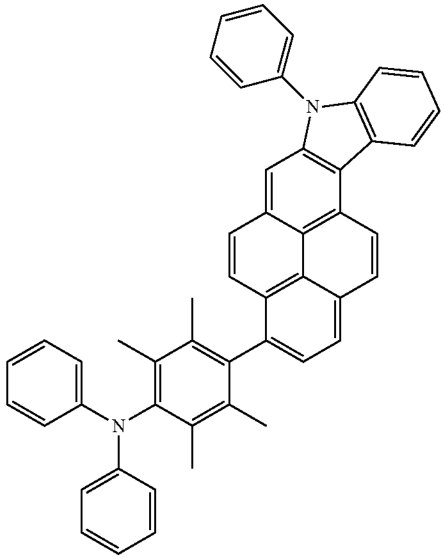
37
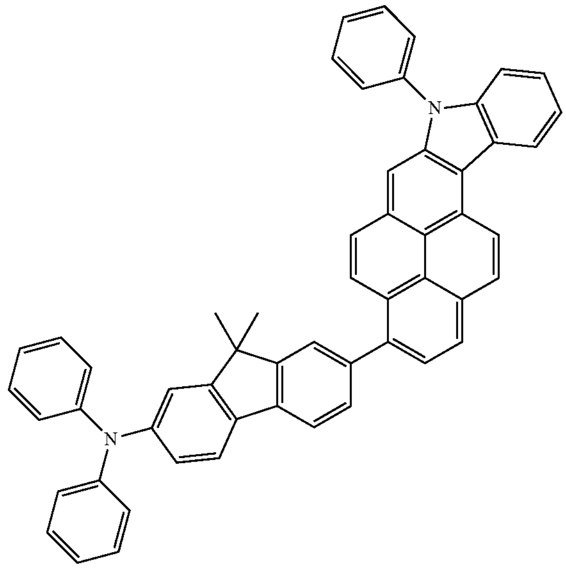
-continued
38
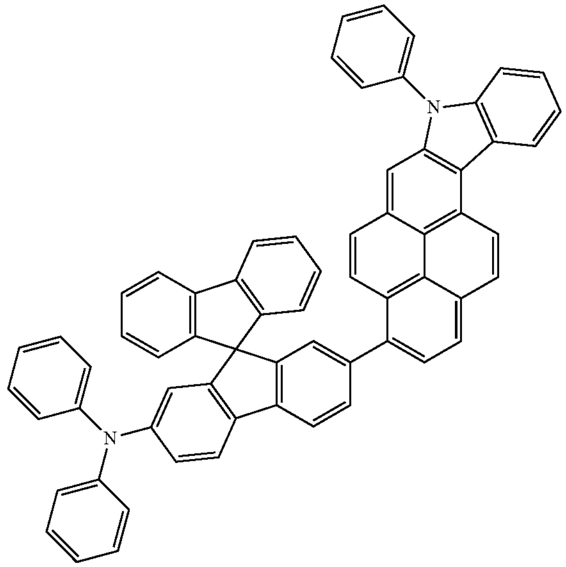
39
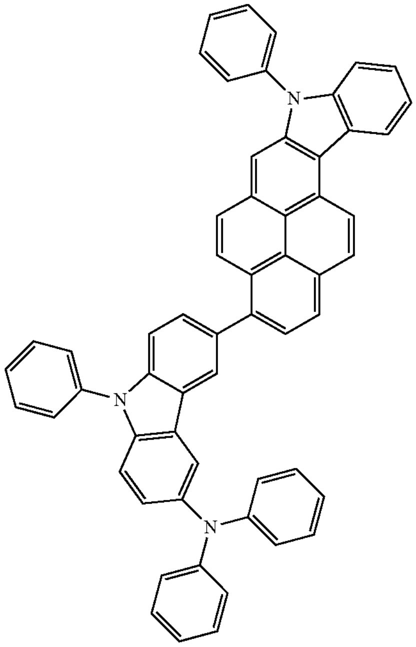

-continued
40
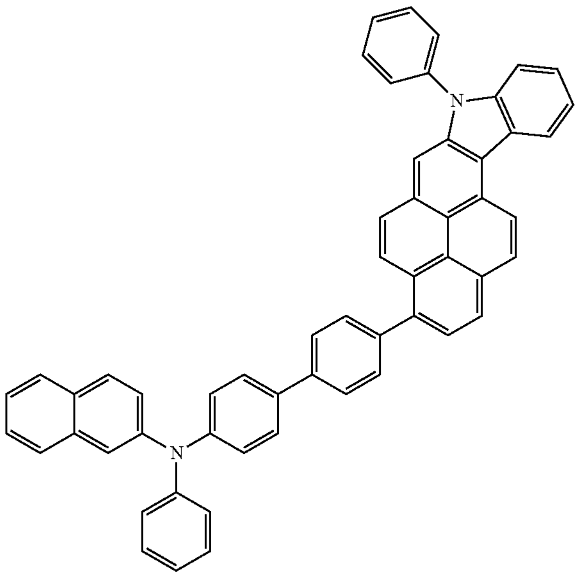
41
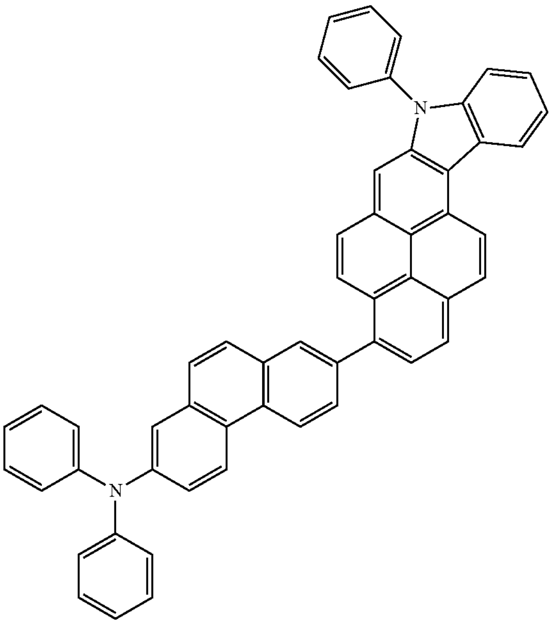
42
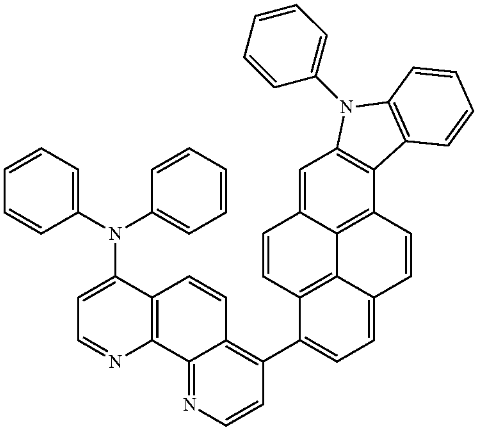
-continued
43
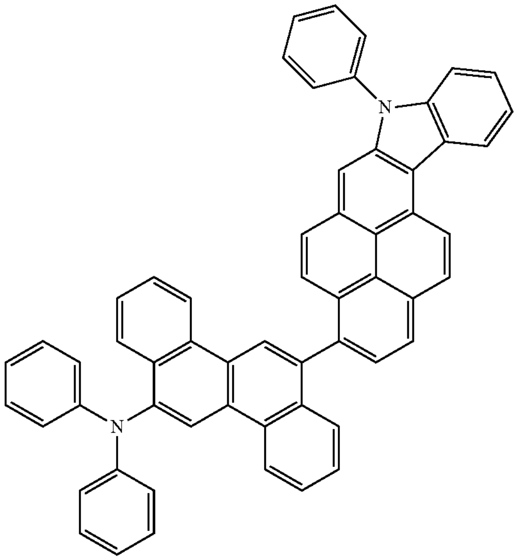
44
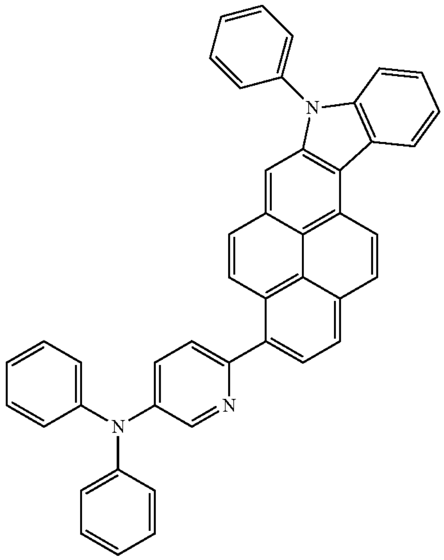

-continued
45
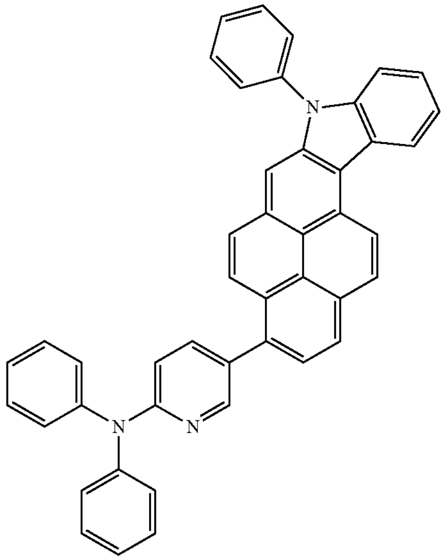
46
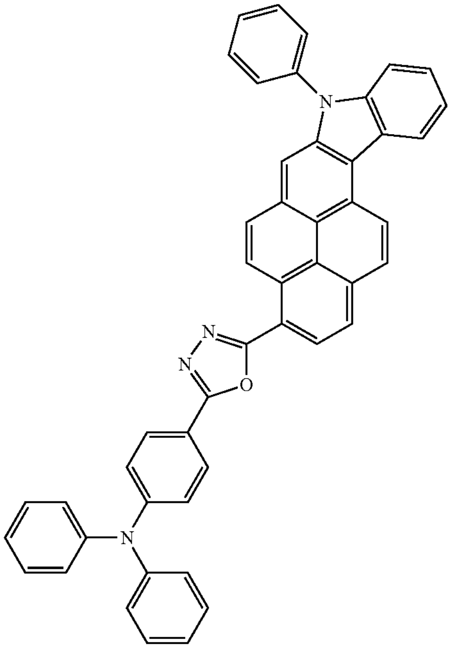
-continued
47
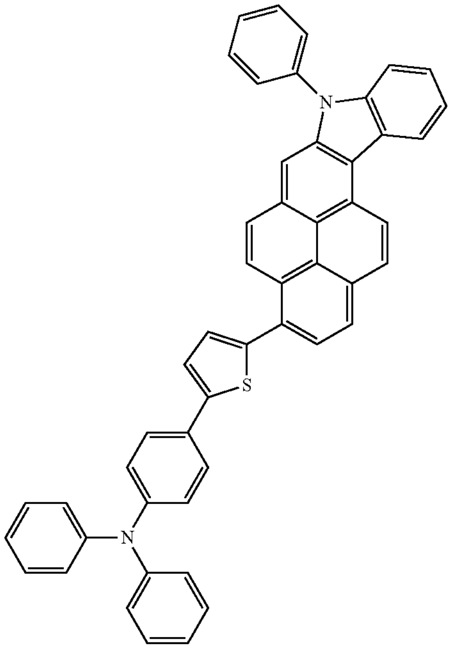
48
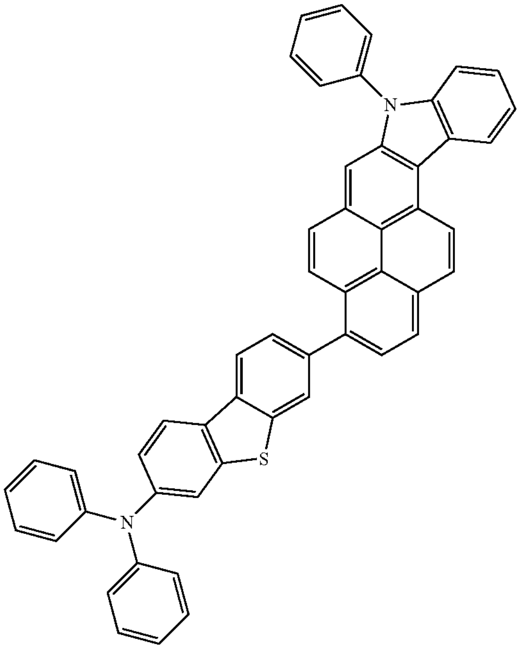

-continued
49
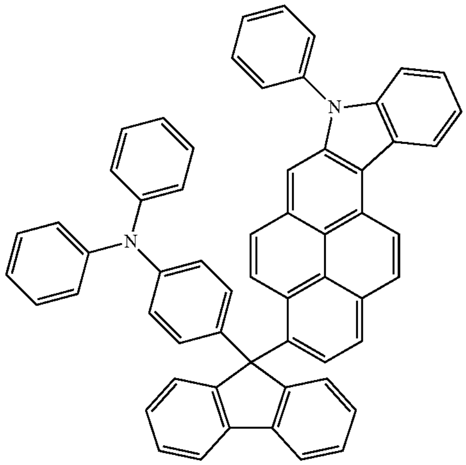
50
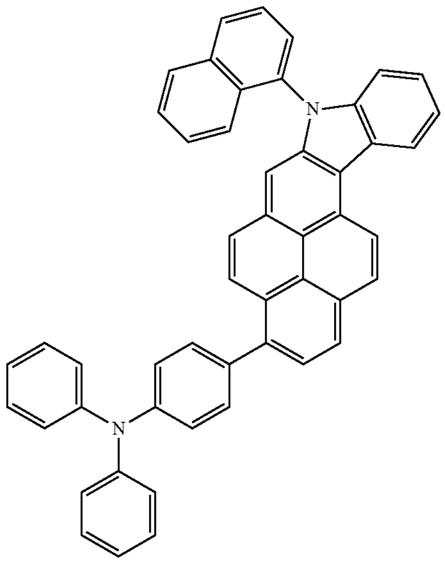
-continued
51
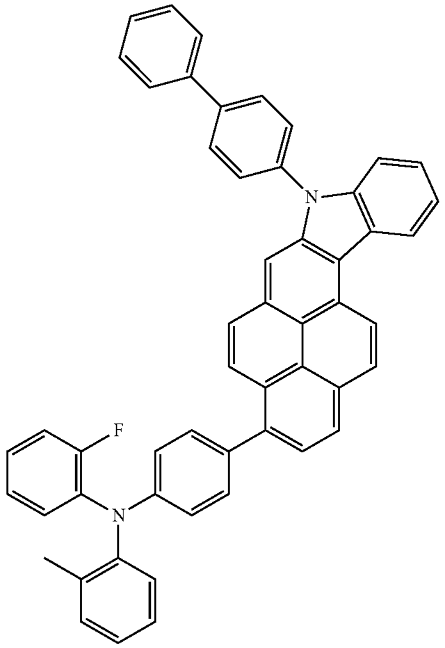
52
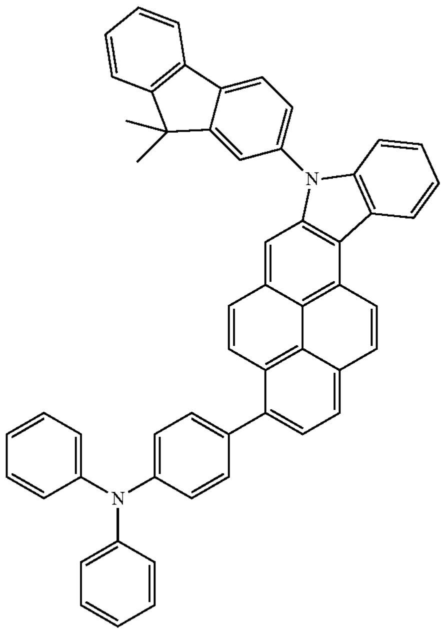

53
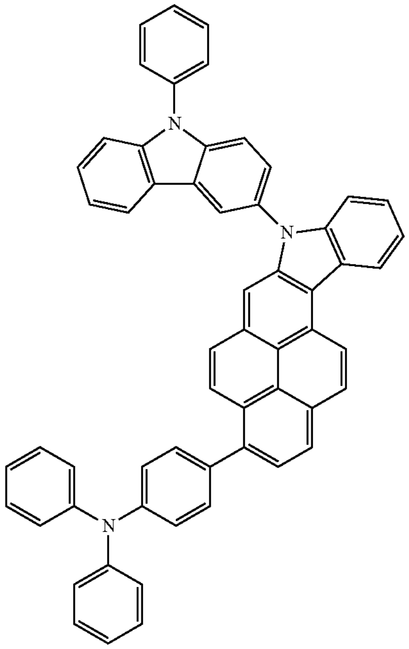
55
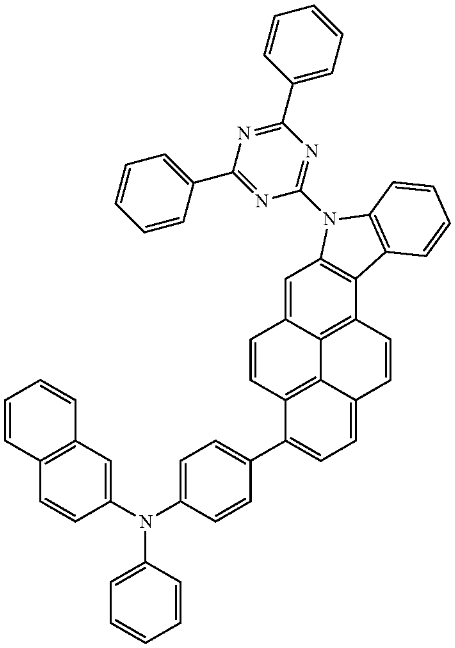
54
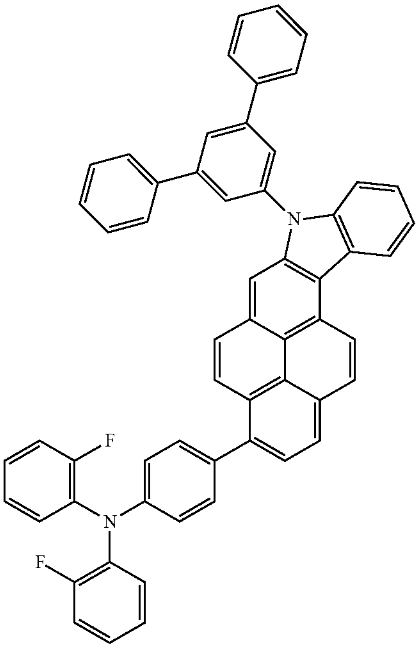
56
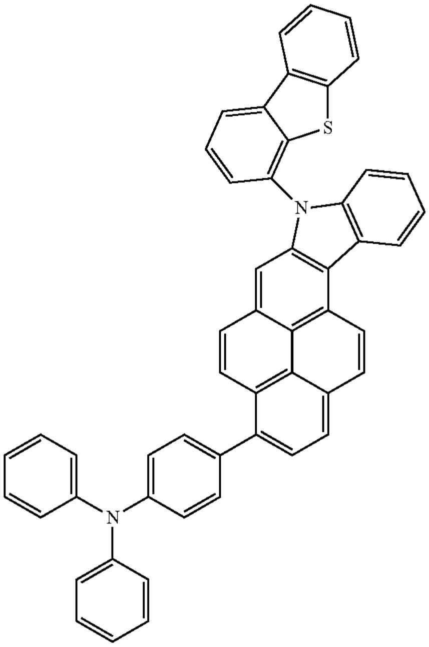

-continued
57
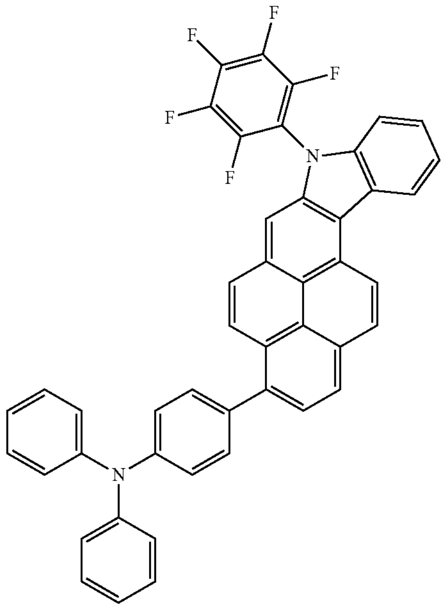
58
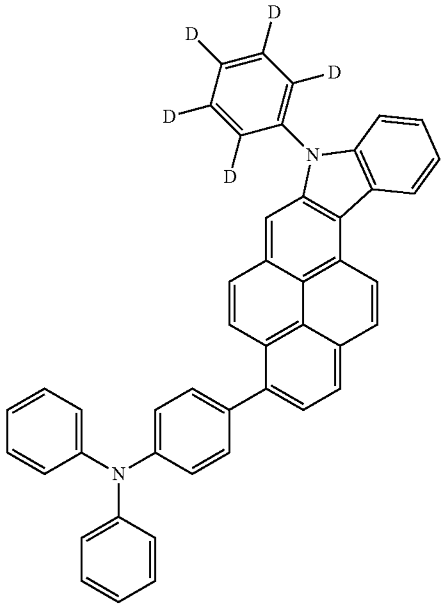
-continued
59
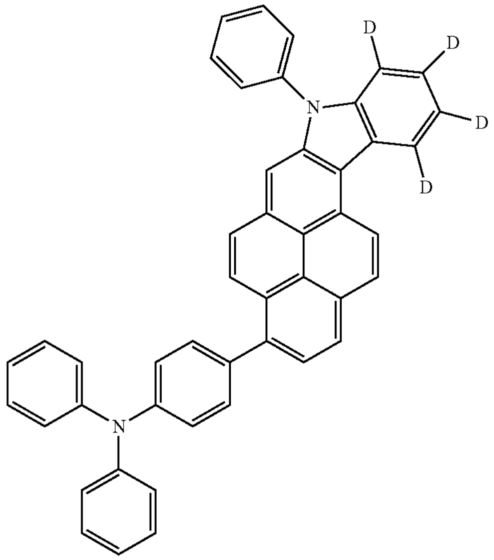
60
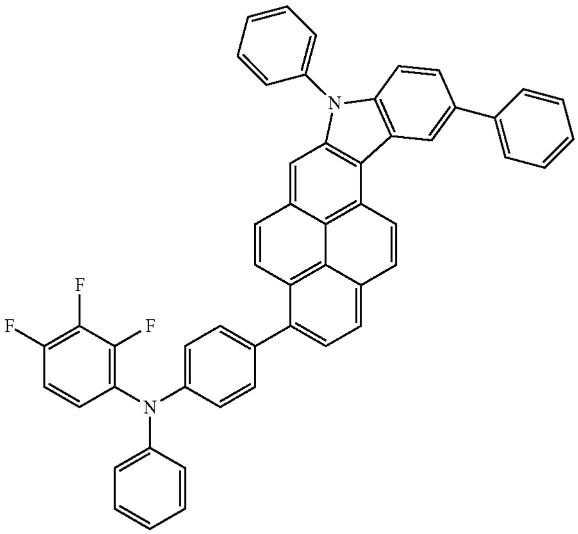
61
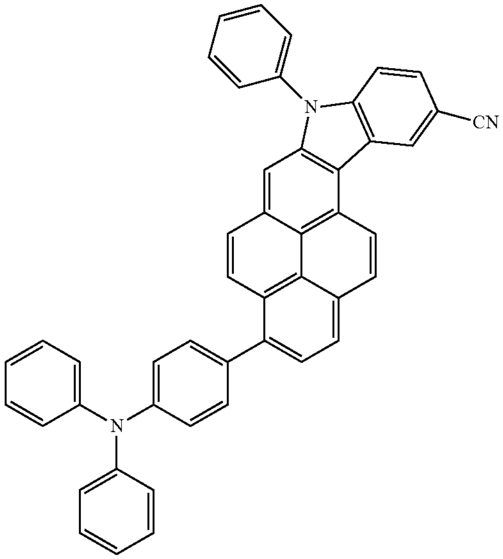

-continued
62
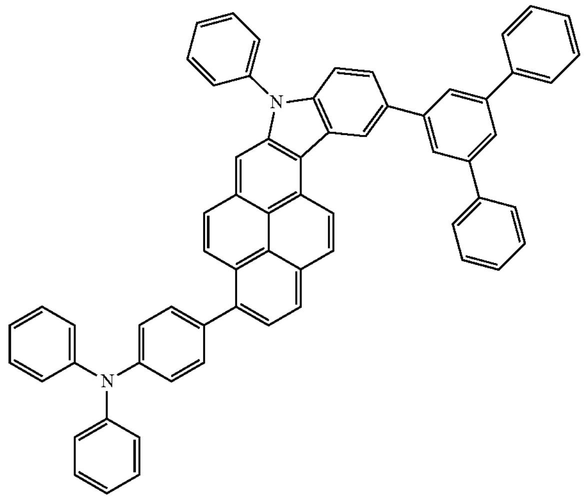
63
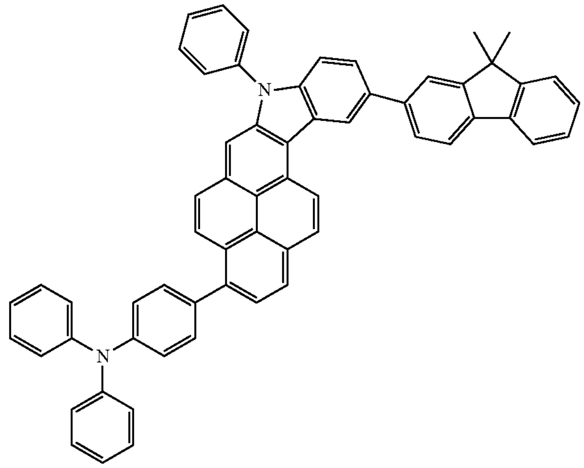
64
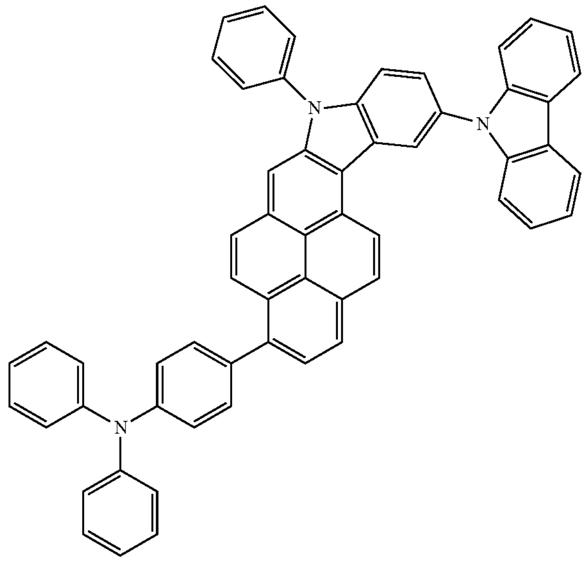
-continued
65
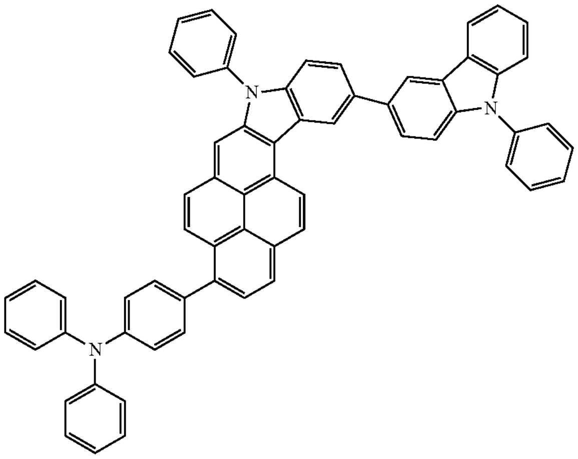
66
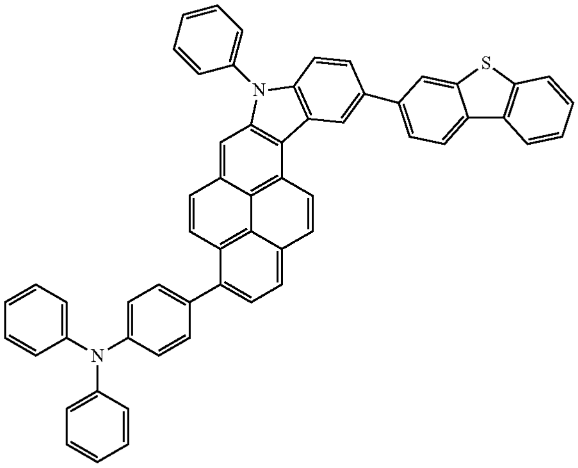
67
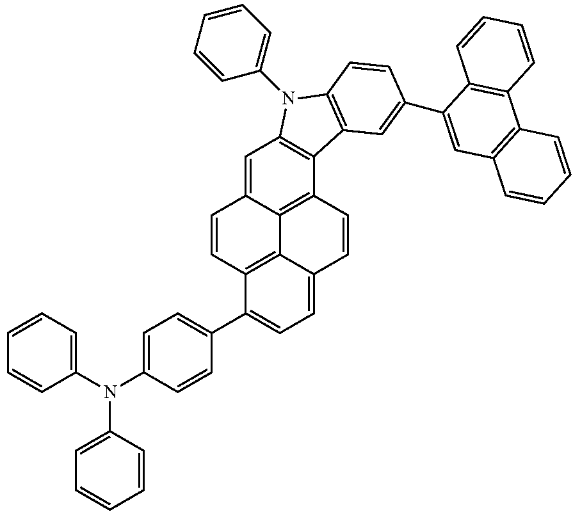

-continued
68
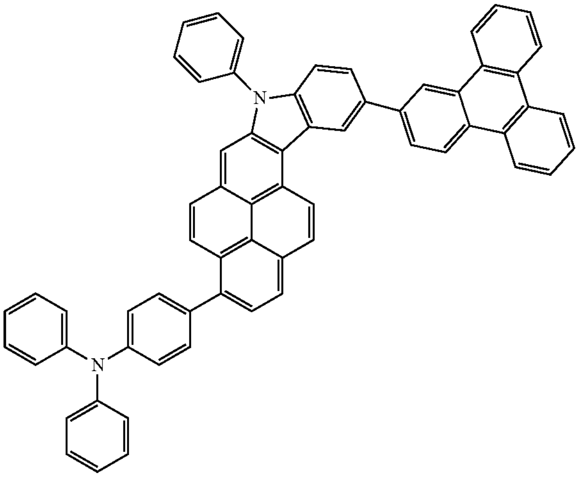
69
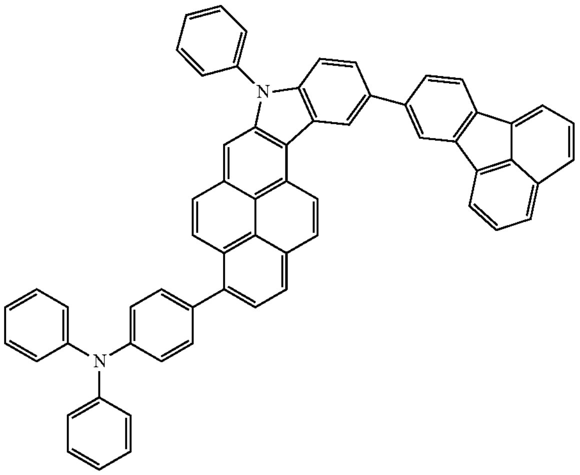
70
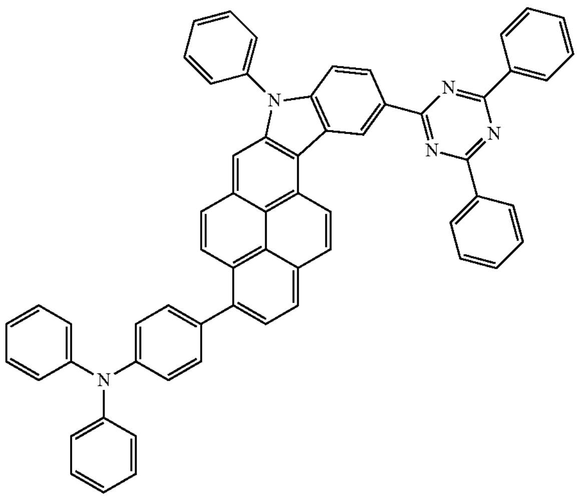
-continued
71
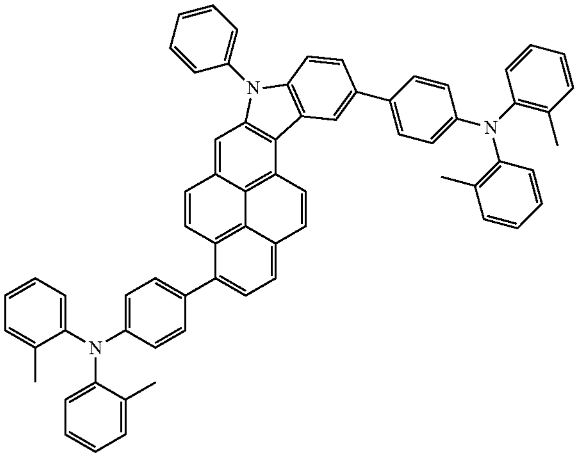
72
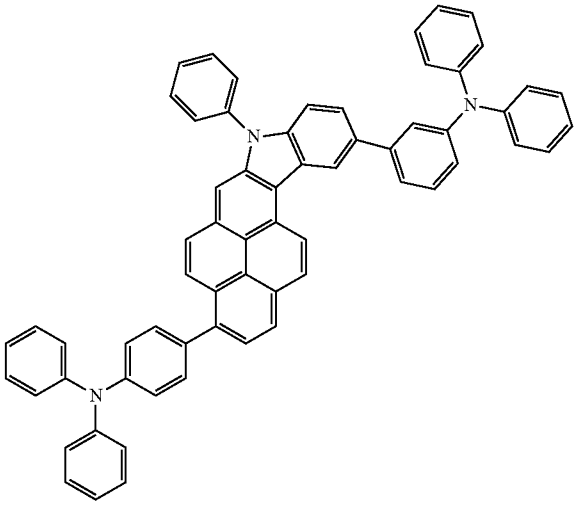
73
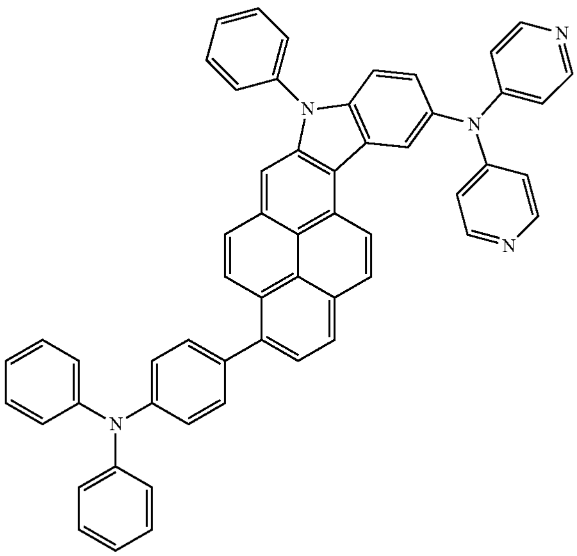

-continued
74
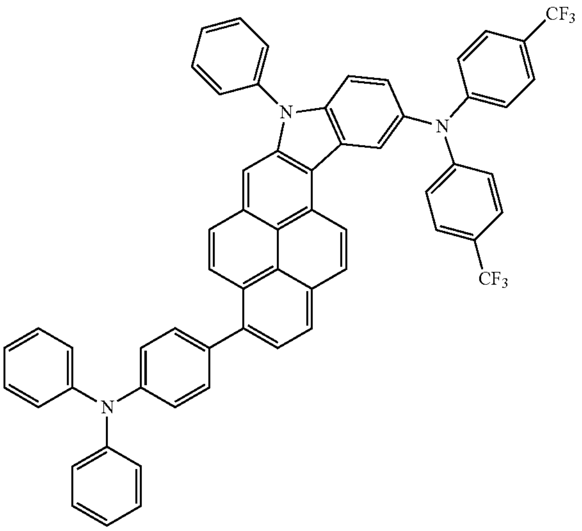
75
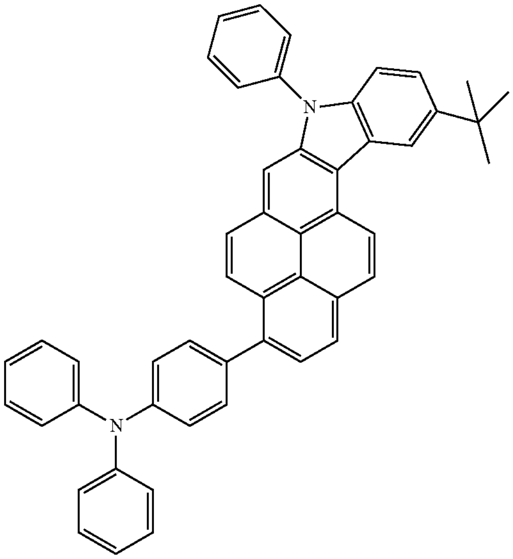
-continued
76
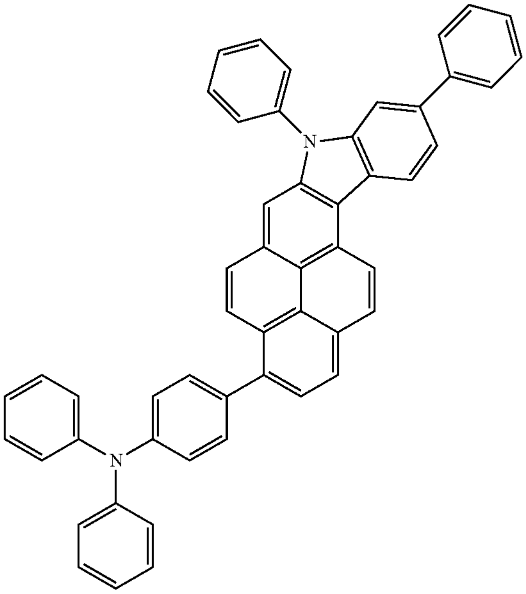
77
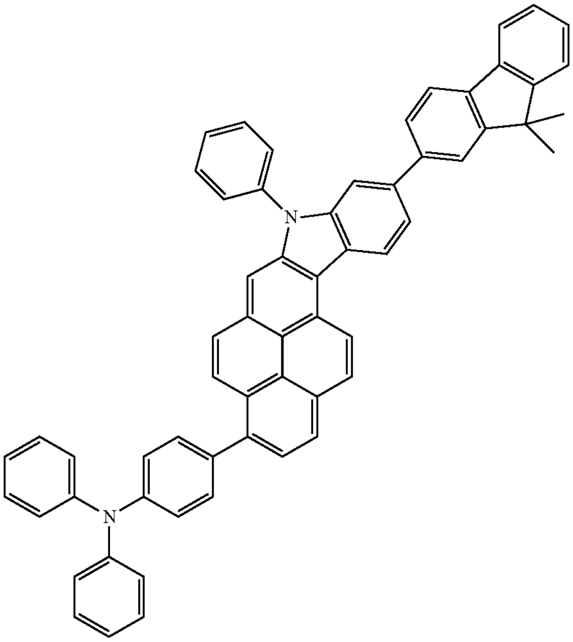

-continued
78
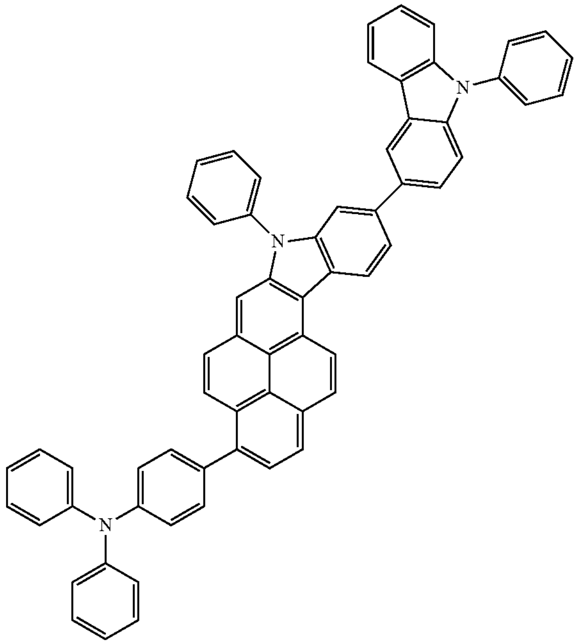
79
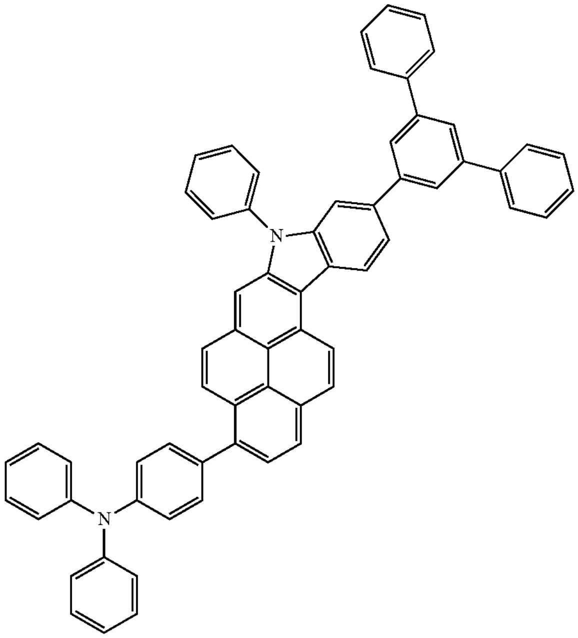
-continued
80
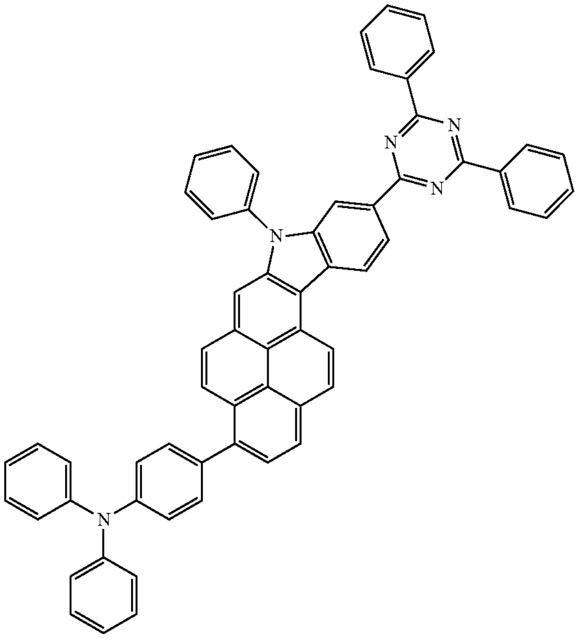
81
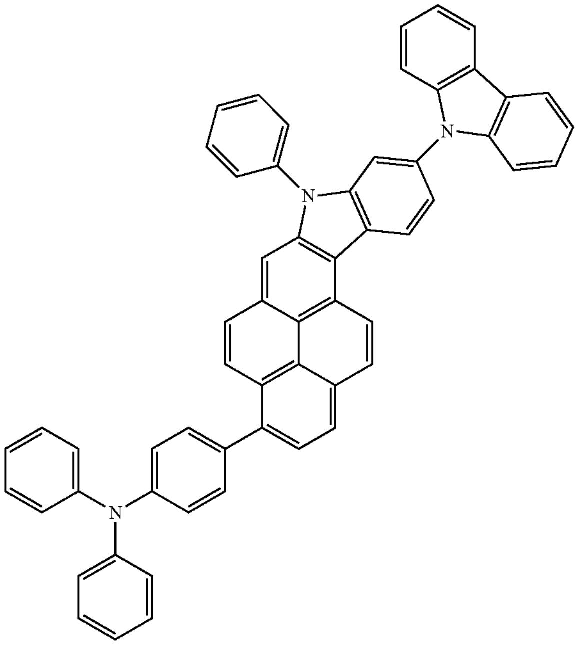

-continued

82

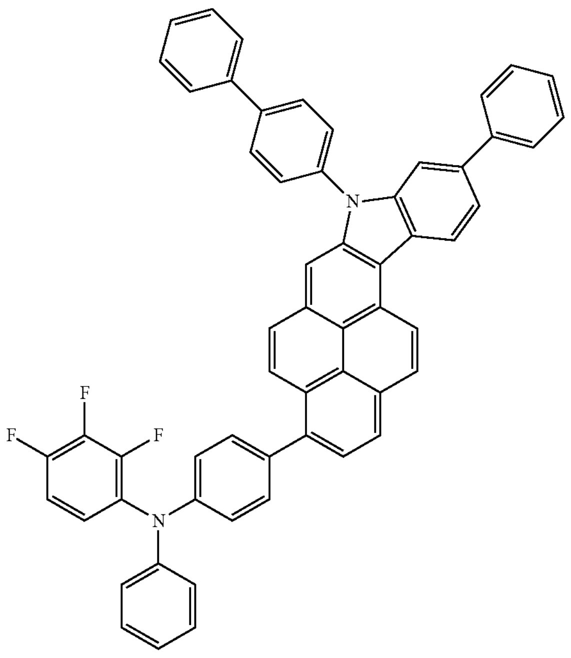

83

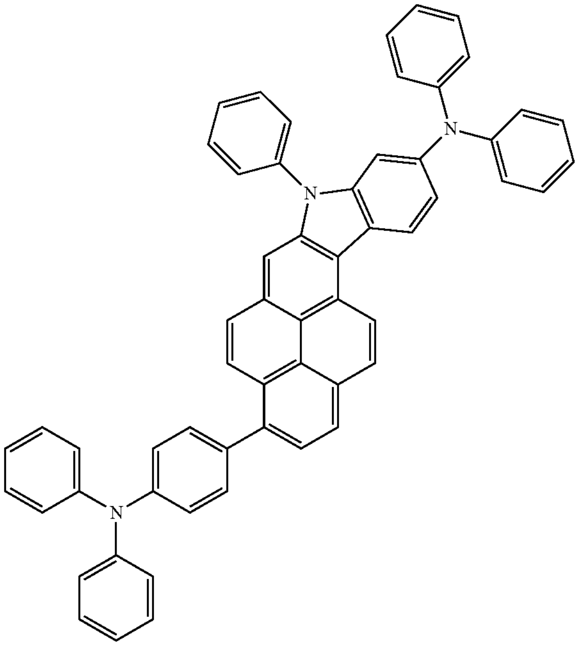

-continued

84

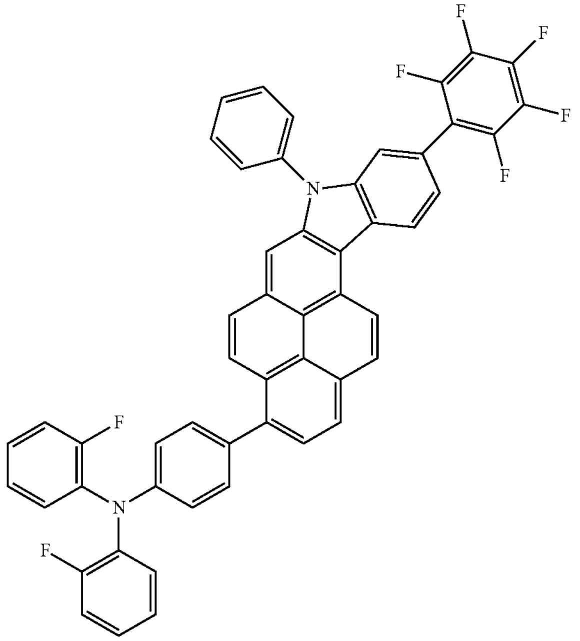

According to an embodiment, an organic light-emitting device includes a first electrode, a second electrode, and an organic layer between the first electrode and the second electrode, in which the organic layer includes a first layer including a heterocyclic compound according to an embodiment of the present invention.

The first layer including the heterocyclic compound may include a hole injection layer, a hole transport layer, or a functional layer having both hole injection and hole transport capabilities.

The first layer including the heterocyclic compound may include an electron injection layer, an electron transport layer, or a functional layer having both electron injection and electron transport capabilities.

When the first layer including the heterocyclic compound of Formula 1 is an emission layer, the heterocyclic compound of Formula 1 may be used in the emission layer as a host or a dopant for a fluorescent or phosphorescent device.

In some embodiments the first layer of the organic light-emitting device may include an emission layer, the emission layer may further include a known anthracene, arylamine or styryl compound.

In addition, at least one hydrogen atom in the anthracene, arylamine or styryl compound may be substituted with a substituent described above in conjunction with the unsubstituted $C_1$-$C_{60}$ alkyl group.

The arylamine is a $C_5$-$C_{60}$ arylamine group and may also be referred to as an amino group with a $C_5$-$C_{60}$ aryl or $C_3$-$C_{60}$ heteroaryl substituent.

In some embodiments the first layer of the organic light-emitting device may include an emission layer, a red layer, a green layer, a blue layer or a white layer of the emission layer may include a widely-known phosphorescent compound.

In some embodiments the first layer of the organic light-emitting device may include a blue emission layer. When the first layer includes a blue emission layer, the heterocyclic compound of Formula 1 may be used as a blue dopant.

The organic layer of the organic light-emitting device may include a hole injection layer, a hole transport layer, a functional layer having hole injecting and transporting capabilities, an emission layer, a hole blocking layer, an electron transport layer, an electron injecting layer, or a combination of two or more layers thereof. However, the organic layer is not limited thereto. At least one layer selected from the hole injection layer, the hole transport layer, or the functional layer having hole injecting and transporting capabilities may further include a charge-generating material, in addition to a heterocyclic compound according to an embodiment of the present invention, a known hole injecting material, and a known hole transporting material, so as to improve film conductivity.

The charge-generating material may be, for example, p-dopant. Nonlimiting examples of the p-dopant are quinine derivatives, such as tetracyanoquinodimethane (TCNQ) or 2,3,5,6-tetrafluoro-tetracyano-1,4-benzoquinonedimethane (F4TCNQ); metal oxides, such as tungsten oxide and molybdenum oxide; and a cyano group-containing compound such as Compound 100 below:

<Compound 100>

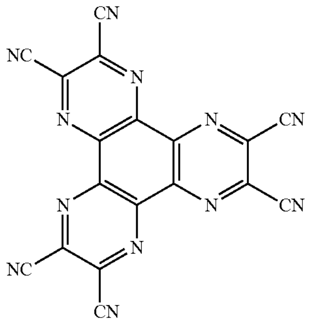

If the hole injection layer, the hole transport layer, or the functional layer having hole injecting and transporting capabilities further include the charge-generating material, the charge-generating material may be uniformly or non-uniformly dispersed in the corresponding layer.

The electron transport layer of the organic light-emitting device according to an embodiment of the present invention may further include an electron transporting organic compound and a metal-containing material. Nonlimiting examples of the electron transporting organic compound are 9,10-di(naphtalene-2-yl)anthracene (ADN); and an anthracene-based compound, such as Compounds 101 and 102 below.

<Compound 101>

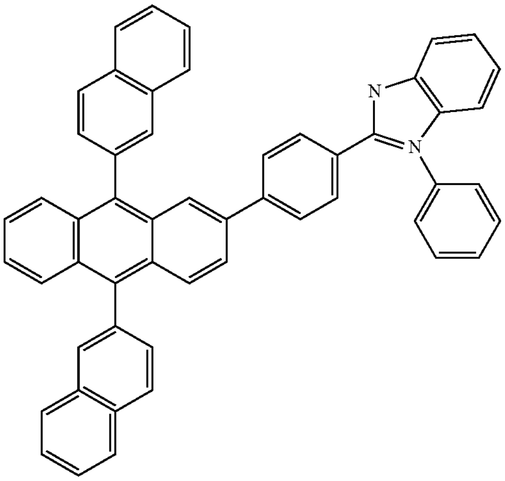

<Compound 102>

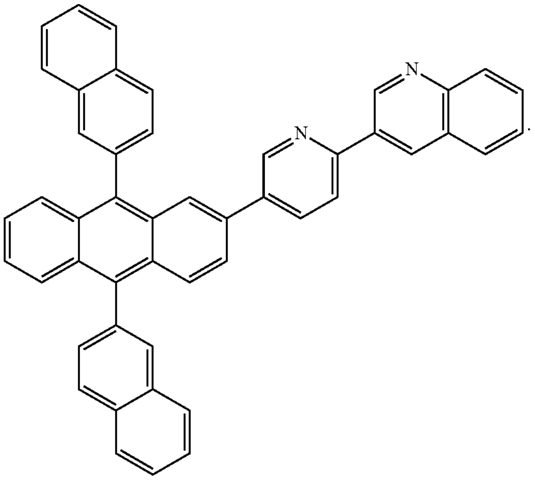

The metal-containing material may include a Li complex. Nonlimiting examples of the Li complex are lithium quinolate (LiQ) and Compound 103 below:

<Compound 103>

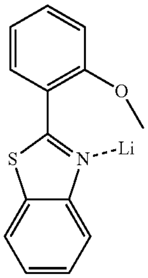

The first electrode may be an anode, and the second electrode may be a cathode, but the reverse is also possible.

In some embodiments, the organic light-emitting device may have a first electrode/hole injection layer/emission layer/second electrode structure, a first electrode/hole injection layer/hole transport layer/emission layer/electron transport layer/second electrode structure, or a first electrode/hole injection layer/hole transport layer/emission layer/electron transport layer/electron injection layer/second electrode structure. In some other embodiments, the organic light-emitting device may have a first electrode/functional layer having both hole injection and hole transport capabilities/emission layer/electron transport layer/second electrode structure, or a first electrode/functional layer having both hole injection and hole transport capabilities/emission layer/electron transport layer/electron injection layer/second electrode structure. Alternatively, the organic light-emitting device may have a first electrode/hole transport layer/emission layer/functional layer having both electron injection and electron transport capabilities/second electrode structure, a first electrode/hole injection layer/emission layer/functional layer having both electron injection and electron transport capabilities/second electrode structure, or a first electrode/hole injection layer/hole transport layer/emission layer/functional layer having both electron injection and electron transport capabilities/second electrode structure.

In some embodiments the organic light-emitting device may be either a top-emission organic light-emitting device or a bottom-emission organic light-emitting device.

Hereinafter, a method of manufacturing an organic light-emitting device according to an embodiment will be described with reference to FIG. 1. FIG. 1 illustrates the structure of an organic light-emitting device according to an embodiment. Referring to FIG. 1, the organic light-emitting device according to the present embodiment includes a substrate (not shown), a first electrode (anode), a hole injection layer (HIL), a hole transport layer (HTL), an emission layer (EML), an electron transport layer (ETL), an electron injection layer (EIL), and a second electrode (cathode).

First, the first electrode is formed on the substrate by using a deposition or sputtering method. The first electrode may comprise a first electrode material having a high work function. The first electrode may constitute an anode or a cathode. The substrate may be a substrate conventionally used in organic light-emitting devices, and may include, for example, a glass substrate or a transparent plastic substrate with excellent mechanical strength, thermal stability, transparency, surface smoothness, ease of handling, and water resistance. Examples of the first electrode material include materials, such as indium tin oxide (ITO), indium zinc oxide (IZO), tin oxide (SnO2), zinc oxide (ZnO), aluminum (Al), silver (Ag), and magnesium (Mg), which have excellent conductivity. The first electrode may be formed as a transparent or reflective electrode.

Then, the HIL may be formed on the first electrode by using any of a variety of methods, and in some embodiments, by using vacuum deposition, spin coating, casting, Langmuir-Blodgett (LB) deposition, or the like.

When the HIL is formed using vacuum deposition, the deposition conditions may vary according to the material that is used to form the HIL, and the structure and thermal characteristics of the HIL. For example, the deposition conditions may include a deposition temperature of from about 100 to about 500° C., a vacuum pressure of about $10^{-8}$ to about $10^{-3}$ ton, and a deposition rate of from about 0.01 to about 100 Å/sec.

When the HIL is formed using spin coating, coating conditions may vary according to the material used to form the HIL, and the structure and thermal properties of the HIL. For example, the coating conditions may include a coating speed of from about 2000 rpm to about 5000 rpm, and a thermal treatment temperature of from about 80° C. to about 200° C. at which the solvent remaining after coating may be removed.

The HIL may comprise the heterocyclic compound of Formula 1 or any material that is commonly used to form a HIL. Nonlimiting examples of the material that can be used to form the HIL include a phthalocyanine compound such as copperphthalocyanine, 4,4',4"-tris (3-methylphenylphenylamino) triphenylamine (m-MTDATA), N,N'-di(1-naphthyl)-N,N'-diphenylbenzidine (NPB), TDATA, 2T-NATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and polyaniline)/poly(4-styrenesulfonate (PANI/PSS).

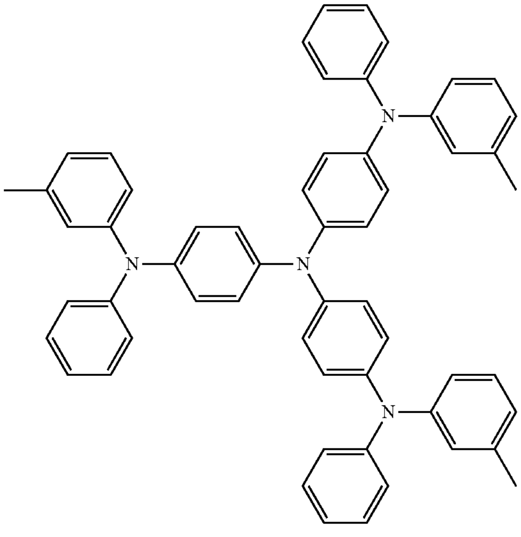

m-MTDATA

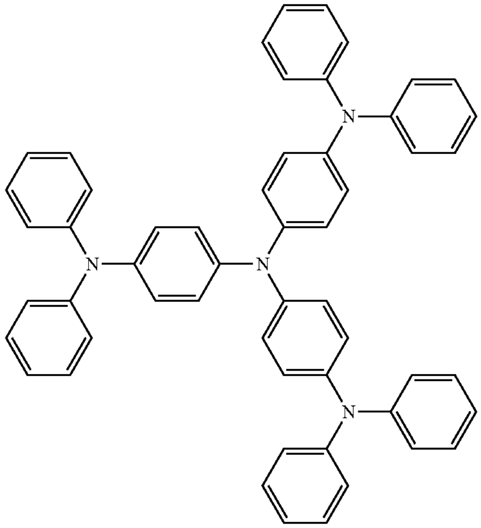

TDATA

-continued

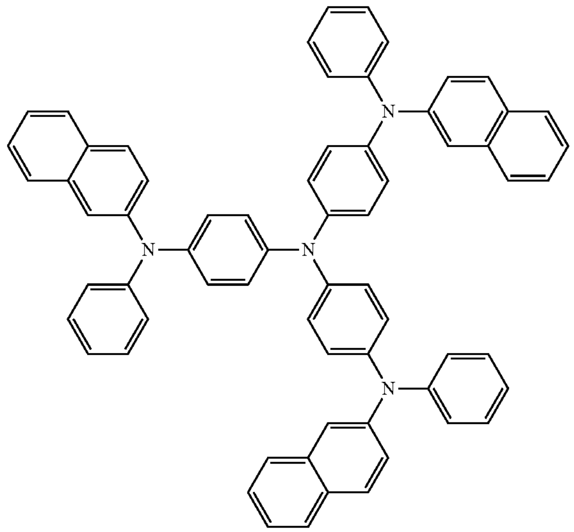

2T-NATA

The HIL may have a thickness of from about 100 Å to about 10000 Å, and in some embodiments, a thickness of from about 100 Å to about 1000 Å. When the thickness of the HIL is within these ranges, the HIL may have good hole injection characteristics without an increase in driving voltage.

Next, the HTL may be formed on the HIL by using any of a variety of methods, and in some embodiments, by using vacuum deposition, spin coating, casting, LB deposition, or the like. When the HTL is formed using vacuum deposition or spin coating, the deposition or coating conditions may be similar to those applied to form the HIL, though the deposition or coating conditions may vary according to the material that is used to form the HTL.

The HTL may comprise the heterocyclic compound of Formula 1 or any known HTL material. Nonlimiting examples of such HTL materials include carbazole derivatives such as N-phenylcarbazole or polyvinylcarbazole, and amine derivatives having an aromatic condensed ring, such as NPB, N,N'-bis(3-methylphenyl)-N,N'-diphenyl-[1,1-biphenyl]-4,4'-diamine (TPD).

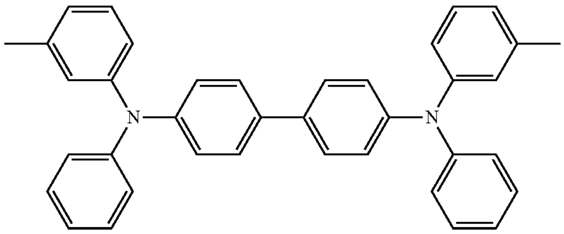

TPD

-continued

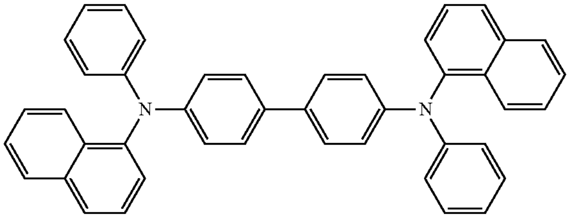

NPB

The HTL may have a thickness of from about 50 Å to about 1000 Å, and in some embodiments, a thickness of from about 100 Å to about 600 Å. When the thickness of the HTL is within these ranges, the HTL may have good hole transport characteristics without a substantial increase in driving voltage.

Next, the EML may be formed on the HTL by using any of a variety of methods, and in some embodiments, by using vacuum deposition, spin coating, casting, LB deposition, or the like. When the EML is formed using vacuum deposition or spin coating, the deposition or coating conditions may be similar to those applied to form the HIL, though the deposition or coating conditions may vary according to the material that is used to form the EML.

The EML may include the heterocyclic compound of Formula 1 described above. For example, the heterocyclic compound of Formula 1 may be used as a host or a dopant. The EML may be formed using a variety of well-known light-emitting materials, in addition to the heterocyclic compound of Formula 1. Alternatively, the EML may also be formed using a well-known host and a dopant. Dopants that may be used to form the EML may include either a fluorescent dopant or a phosphorescent dopant, which are widely known in the art.

Examples of the host include Alq3, 4,4'-N,N'-dicarbazole-biphenyl (CBP), poly(n-vinylcarbazole) (PVK), 9,10-di (naphthalene-2-yl)anthracene (ADN), TCTA, 1,3,5-tris(N-phenylbenzimidazole-2-yl)benzene (TPBI), 3-tert-butyl-9,10-di-2-naphthylanthracene (TBADN), E3, and distyrylarylene (DSA), bur are not limited thereto.

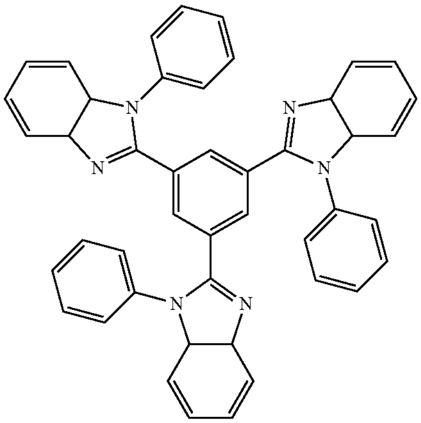

TPBI

-continued
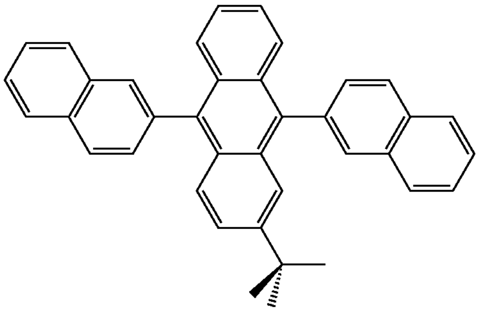
TBADN
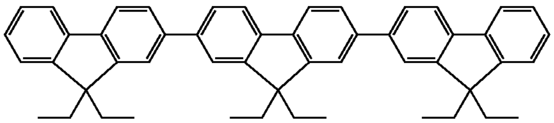
E3
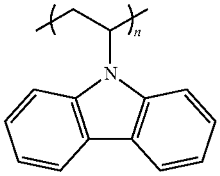
PVK
Nonlimiting examples of red dopants include platinum(II) octaethylporphyrin (PtOEP), Ir(piq)$_3$, Btp$_2$Ir(acac), and DCJTB.
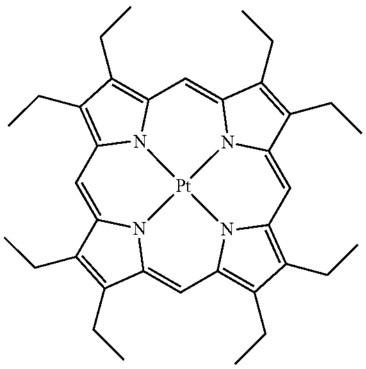
PtOEP
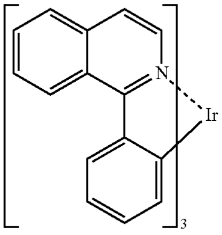
Ir(piq)$_3$
-continued
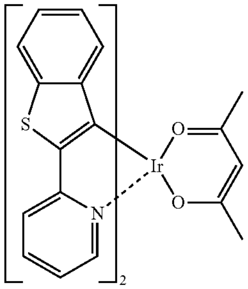
Btp$_2$Ir(acac)
Nonlimiting examples of green dopants include Ir(ppy)$_3$ (where "ppy" denotes phenylpyridine), Ir(ppy)$_2$(acac), Ir(m-pyp)$_3$, and C545T.
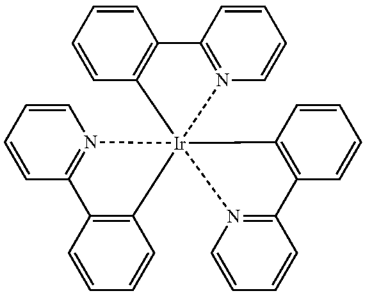
Ir(ppy)$_3$
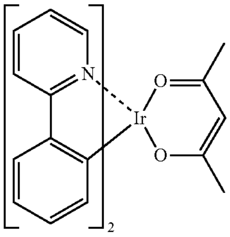
Ir(ppy)$_2$(acac)
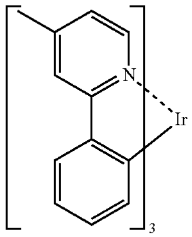
Ir(mpyp)$_3$ -continued

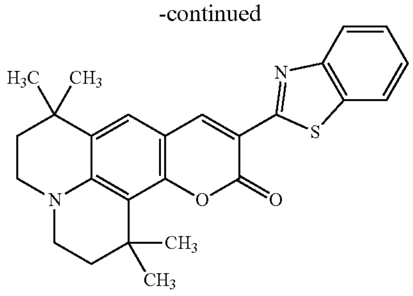

C545T

Non-limiting examples of blue dopants include the heterocyclic compound of Formula 1, $F_2$Irpic, ($F_2$ ppy)$_2$Ir(tmd), Ir(dfppz)$_3$, ter-fluorene, 4,4'-bis(4-diphenylaminostyryl)biphenyl (DPAVBi), and 2,5,8,11-tetra-t-butyl phenylene (TBP).

used to form a HBL. Nonlimiting examples of such HBL materials include oxadiazole derivatives, triazole derivatives, phenathroline derivatives, Balq, and BCP.

The HBL may have a thickness of from about 50 Å to about 1,000 Å, and in some embodiments, from about 100 Å to about 300 Å. When the thickness of the HBL is within these ranges, the HBL may have good hole blocking characteristics without a substantial increase in driving voltage.

Next, the ETL is formed on the EML (or HBL) by using any of a variety of methods, and in some embodiments, by using vacuum deposition, spin coating, casting, or the like. When the ETL is formed using vacuum deposition or spin coating, the deposition or coating conditions may be similar to those applied to form the HIL, though the deposition or coating conditions may vary according to the material that is used to form the ETL.

The ETL material may include the heterocyclic compound of Formula 1 described above. Alternatively, the ETL may comprise any material that is widely known in the art. Non-

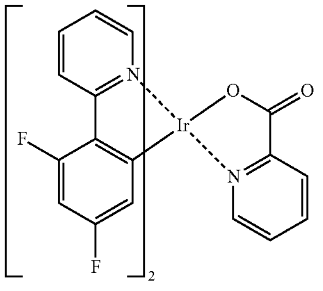

$F_2$Irpic

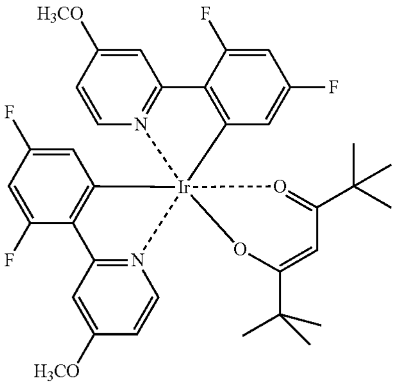

Ir(ppy)$_3$

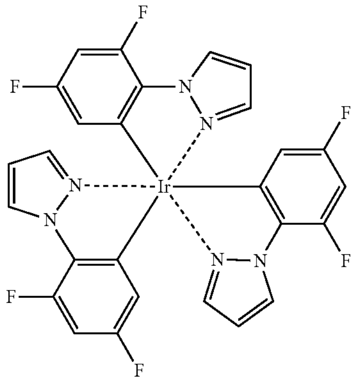

Ir(dfppz)$_3$

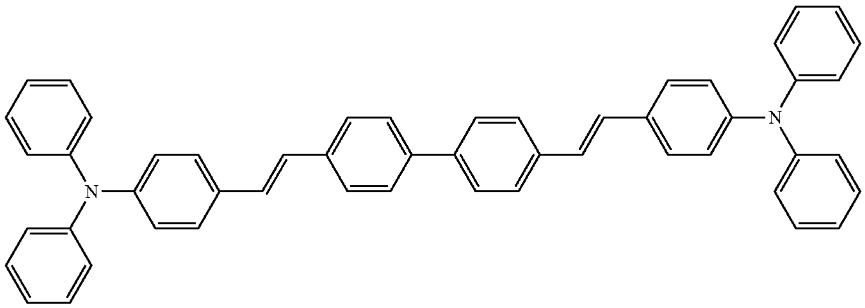

DPAVBi

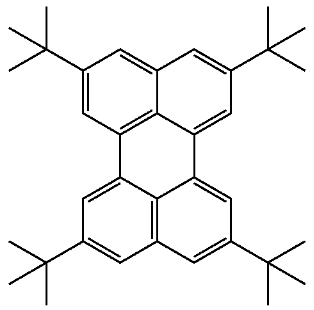

TBP

The amount of the dopant may be from about 0.1 to about 20 parts by weight, and in some embodiments, from about 0.5 to about 12 parts by weight, based on 100 parts by weight of the EML material, which is equivalent to the total weight of the host and the dopant. When the amount of the dopant is within these ranges, concentration quenching may be substantially prevented.

The EML may have a thickness of from about 100 Å to about 1,000 Å, and in some embodiments, from about 200 Å to about 600 Å. When the thickness of the EML is within these ranges, the EML may have good light-emitting characteristics without a substantial increase in driving voltage.

When the EML includes a phosphorescent dopant, a HBL (not shown in FIG. 1) may be formed on the EML in order to prevent diffusion of triplet excitons or holes into the ETL. In this case, the HBL may comprise any material commonly limiting examples of the ETL material include quinoline derivatives, such as tris(8-quinolinolate)aluminum (Alq3), TAZ, and BAlq.

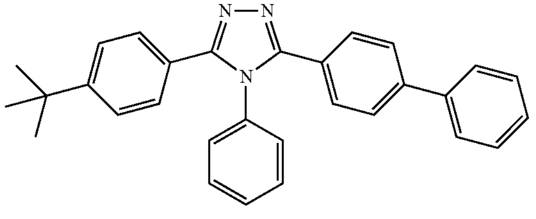

TAZ

-continued

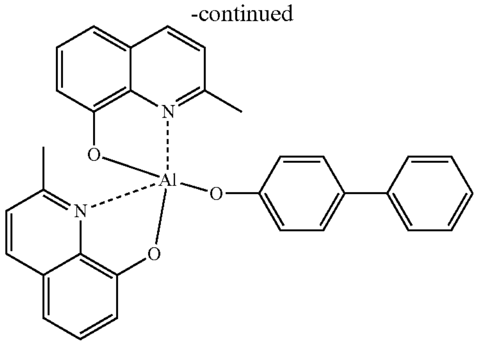

BAlq

The ETL may have a thickness of from about 100 Å to about 1,000 Å, and in some embodiments, from about 100 Å to about 500 Å. When the thickness of the ETL is within these ranges, the ETL may have good electron transport characteristics without a substantial increase in driving voltage.

In addition, the EIL, which facilitates injection of electrons from the cathode, may be formed on the ETL.

The EIL may include the heterocyclic compound of Formula 1 described above. In some embodiments well-known EIL materials, such as LiF, NaCl, CsF, $Li_2O$, or BaO, may be used to form the EIL. The deposition or coating conditions may be similar to those applied to form the HIL, although the deposition and coating conditions may vary according to the material that is used to form the EIL.

The EIL may have a thickness of from about 1 Å to about 100 Å, and in some embodiments, from about 5 Å to about 90 Å. When the thickness of the EIL is within these ranges, the EIL may have good electron injection characteristics without a substantial increase in driving voltage.

Finally, the second electrode may be formed on the EIL by using, for example, vacuum deposition, sputtering, or the like. The second electrode may constitute a cathode or an anode. The material for forming the second electrode may include a metal, an alloy, or an electrically conductive compound, which are materials having a low work function, or a mixture thereof. Nonlimiting examples of such materials include lithium (Li), magnesium (Mg), aluminum (Al), aluminum-lithium (Al—Li), calcium (Ca), magnesium-indium (Mg—In), and magnesium-silver (Mg—Ag). In addition, in order to manufacture a top-emission organic light-emitting device, a transparent cathode comprising a transparent material such as ITO or IZO may be used as the second electrode.

According to embodiments, the organic light-emitting device may be included in various types of flat panel display devices, such as in a passive matrix organic light-emitting display device or in an active matrix organic light-emitting display device. In particular, when the organic light-emitting device is included in an active matrix organic light-emitting display device including a thin-film transistor, the first electrode on the substrate may function as a pixel electrode, electrically connected to a source electrode or a drain electrode of the thin-film transistor. Moreover, the organic light-emitting device may also be included in flat panel display devices having double-sided screens.

According to embodiments, the organic light-emitting device may include the first layer, wherein the first layer may be formed by depositing a heterocyclic compound according to an embodiment of the present invention or by using a wet method of coating a solution of the heterocyclic compound according to an embodiment of the present invention.

Hereinafter, the present embodiments will be described in detail with reference to synthesis examples of Compounds 2, 11, 24, 34, 45, 48, 55, 57, 73, and 82 and other examples. However, these examples are for illustrative purposes only and are not intended to limit the scope of the present embodiments.

EXAMPLES

Synthesis Example 1

Synthesis of Intermediate I-1

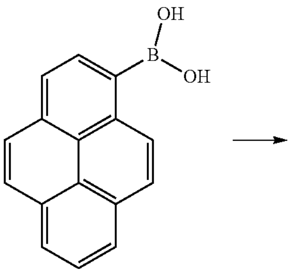

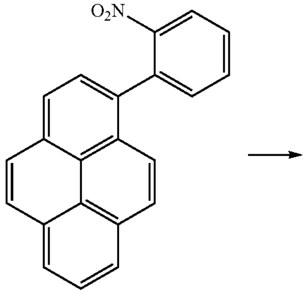

I-1

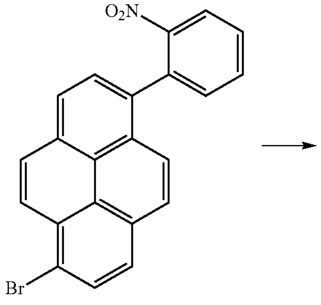

I-2

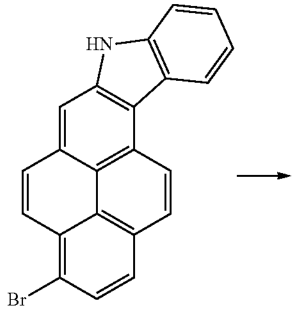

I-3

-continued

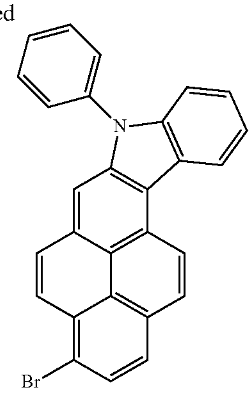

I-4

4.93 g (20.0 mmol) of pyren-1-yl-1-boronic acid, 4.04 g (20.0 mmol) of 2-bromonitrobenzene, 1.15 g (1.0 mmol) of $Pd(PPh_3)_4$, and 8.29 g (60.0 mmol) of $K_2CO_3$ were dissolved in 60 mL of a mixed tetrahydrofuran (THF) and $H_2O$ (2:1) solution to obtain a solution, which was then stirred at from about 70° C. for about 5 hours. The reaction solution was cooled to room temperature, and 40 mL of water was added thereto, followed by three times of extraction with 50 mL of ethylether. The organic phase was collected, and was dried using magnesium sulfate to evaporate the solvent. The residue was separated and purified using silica gel column chromatography to obtain 5.95 g of Intermediate I-1 (Yield: 92%). This compound was identified using HR-MS and NMR. $C_{22}H_{13}NO_2$ estimated value: 323.0946; measured value: 323.0939

$^1H$ NMR ($CDCl_3$, 400 MHz) δ (ppm) 8.22-8.20 (d, 2H), 8.17-8.10 (m, 4H), 8.03-8.01 (d, 1H), 8.01-7.98 (d, 1H), 7.88-7.85 (d, 1H), 7.69-7.67 (m, 2H), 7.66-7.56 (m, 2H)

Synthesis Example 2

Synthesis of Intermediate I-2

4.85 g (15.0 mmol) of Intermediate I-1 was dissolved in 100 mL of dichloromethane 100 ml to obtain a solution, and 1.75 ml (15.0 mmol) of bromine ($Br_2$) was slowly dropwise added to the solution at about 0° C. to obtain a reaction solution. The reaction solution was stirred at room temperature for from about 12 hours. 60 mL of water and 30 mL of a 20% aqueous thiosodium sulfate solution were added to the reaction solution, followed by three times of extraction with 80 mL of dichloromethane. The organic phase was collected, and was dried using magnesium sulfate to evaporate the solvent. The residue was separated and purified by silica gel column chromatography, followed by recrystallization with a dichloromethane/hexane solution to obtain 3.38 g of Intermediate I-2 (Yield 56%). This compound was identified using HR-MS and NMR. $C_{22}H_{12}BrNO_2$ estimated value: 401.0051; measured value: 401.0046

$^1H$ NMR ($CDCl_3$, 400 MHz) δ (ppm) 8.50-8.47 (d, 1H), 8.40-8.22 (dd, 2H), 8.18-8.15 (dd, 1H), 8.10-8.00 (m, 3H), 7.91-7.89 (d, 1H), 7.83-7.80 (d, 1H), 7.79-7.74 (dt, 1H), 7.70-7.65 (dt, 1H), 7.59-7.53 (dd, 1H)

Synthesis Example 3

Synthesis of Intermediate I-3

4.02 g (10.0 mmol) of Intermediate I-2 and 5.77 g (22 mmol) of triphenylphosphine ($PPh_3$) were dissolved in 30 mL of 1,2-dichlorobenzene to obtain a solution, which was then stirred at about 170° C. for about 12 hours. The reaction solution was cooled to room temperature, and the solvent was removed therefrom under vacuum conditions, followed by three times of extraction with 50 mL of water and 50 mL of dichloromethane. The organic phase was collected, and was dried using magnesium sulfate to evaporate the solvent. The residue was separated and purified using silica gel column chromatography to obtain 2.66 g of Intermediate I-3 (Yield: 72%). This compound was identified using HR-MS and NMR. $C_{22}H_{12}BrN$ estimated value: 369.0153; measured value: 323.0939

$^1H$ NMR (THF-$d_8$, 400 MHz) δ (ppm) 11.06 (s, 1H), 9.37-9.34 (d, 1H), 8.88-8.85 (d, 1H), 8.73-8.69 (d, 1H), 8.33 (s, 1H), 8.23-8.17 (t, 2H), 8.08-8.00 (dd, 2H), 7.69-7.66 (d, 1H), 7.56-7.51 (dt, 1H), 7.44-7.38 (dt, 1H)

Synthesis Example 4

Synthesis of Intermediate I-4

3.70 g (10.0 mmol) of Intermediate I-3, 3.06 g (15.0 mmol) of iodobenzene, 0.19 g (1.0 mmol) of CuI, 0.05 g (0.2 mmol) of 18-Crown-6, and 4.15 g (30.0 mmol) of $K_2CO_3$ were dissolved in 30 mL of 1,3-dimethyl-3,4,5,6-tetrahydro-2(1H)-pyrimidinone (DMPU) to obtain a solution, which was then stirred at about 170° C. for about 12 hours. The reaction solution was cooled to room temperature, followed by three times of extraction with 50 mL of water and 50 mL of dichloromethane. The organic phase was collected, and was dried using magnesium sulfate to evaporate the solvent. The residue was separated and purified using silica gel column chromatography to obtain 4.15 g of Intermediate I-4 (Yield: 93%). This compound was identified using HR-MS and NMR. $C_{28}H_{16}BrN$ estimated value: 445.0466; measured value: 445.0459

$^1H$ NMR ($CDCl_3$, 400 MHz) δ (ppm) 9.09-9.05 (d, 1H), 8.67-8.65 (dd, 1H), 8.53-8.50 (d, 1H) 8.01-7.99 (d, 1H), 7.94 (s, 1H), 7.86-7.75 (m, 3H), 7.56-7.47 (m, 5H), 7.44-7.31 (m, 4H)

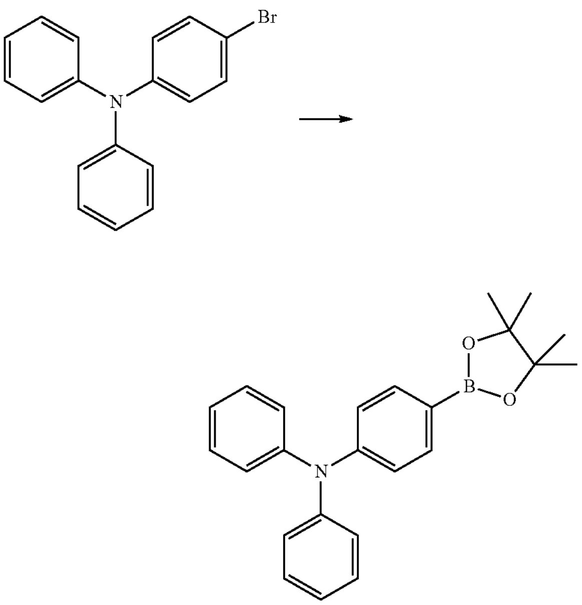

I-5

Synthesis Example 5

Synthesis of Intermediate I-5

3.24 g (10.0 mmol) of 4-bromotriphenylamine, 2.54 g (10.0 mmol) of bis(pinacolato)diborone, 0.36 g (0.5 mmol) of [1,1'-bis(diphenylphosphino)ferrocene]dichloro palladium (II) (hereinafter, $PdCl_2(dppf)_2$), and 2.94 g (30.0 mmol) of KOAc were dissolved in 40 mL of dimethylsulfoxide (DMSO) to obtain a solution, which was then stirred at about 80° C. for about 6 hours. The reaction solution was cooled to room temperature, followed by three times of extraction with 50 mL of water and 50 mL of diethylether. The organic phase was collected, and was dried using magnesium sulfate to evaporate the solvent. The residue was separated and purified using silica gel column chromatography to obtain 2.57 g of Intermediate I-5 (Yield: 89%). This compound was identified using HR-MS and NMR. $C_{24}H_{26}BNO_2$ estimated value: 371.2057; measured value 371.2051

$^1H$ NMR ($CDCl_3$, 400 MHz) δ (ppm) 7.67-7.63 (m, 2H), 7.30-7.21 (m, 4H), 7.14-7.06 (m, 4H), 7.05-7.00 (m, 4H), 1.32 (s, 12H)

Synthesis Example 6

Synthesis of Compound 2

2.23 g (5.0 mmol) of Intermediate I-4, 1.86 g (5.0 mmol) of Intermediate I-5, 0.29 g (0.25 mmol) of $Pd(PPh_3)_4$, and 2.07 g (15.0 mmol) of $K_2CO_3$ were dissolved in 30 mL of a mixed solution $THF/H_2O$ (2:1) to obtain a solution, which was then stirred at about 70° C. for about 5 hours. The reaction solution was cooled to room temperature, followed by three times of extraction with 50 mL of water and 50 mL of diethylether. The organic phase was collected, and was dried using magnesium sulfate to evaporate the solvent. The residue was separated and purified using silica gel column chromatography to obtain 2.11 g of Compound 2 (Yield: 69%). This compound was identified using HR-MS and NMR. $C_{46}H_{30}N_2$ estimated value: 610.2409; measured value [M+1] 611.2401

$^1H$ NMR ($CDCl_3$, 400 MHz) δ (ppm) 9.25-9.21 (d, 1H), 8.92-8.85 (m, 1H), 8.66-8.62 (d, 1H), 8.26-8.24 (d, 1H), 8.17 (s, 1H), 8.07 (s, 2H), 8.01-7.98 (d, 1H), 7.76-7.74 (d, 4H), 7.62-7.56 (m, 6H), 7.39-7.23 (m, 10H), 7.12-7.00 (dt, 2H)

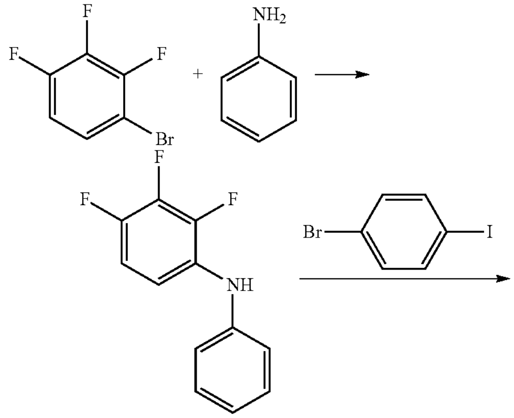

I-6

-continued

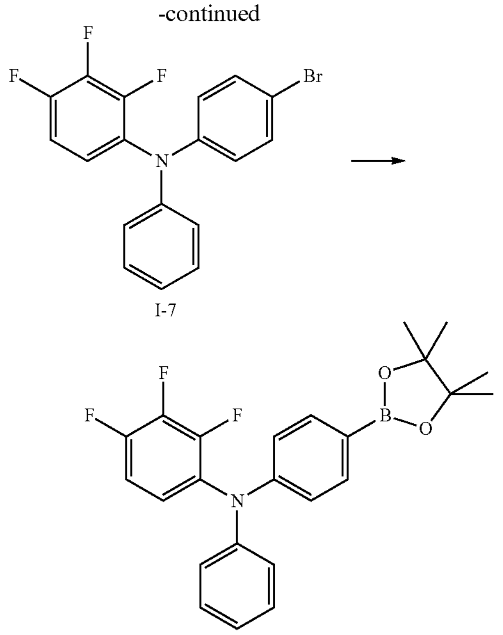

I-7

I-8

Synthesis Example 7

Synthesis of Intermediate I-6

4.22 g (20.0 mmol) of 1-bromo-2,3,4-trifluorobenzene, 2.79 g (30.0 mmol) of aniline, 0.37 g (0.4 mmol) of $Pd_2(dba)_3$, 0.08 g (0.4 mmol) of $PtBu_3$, and 2.88 g (30.0 mmol) of KOtBu were dissolved in 60 mL of toluene to obtain a solution, which was then stirred at about 85° C. for about 4 hours. The reaction solution was cooled to room temperature, followed by three times of extraction with 50 mL of water and 50 mL of diethylether. The organic phase was collected, and was dried using magnesium sulfate to evaporate the solvent. The residue was separated and purified using silica gel column chromatography to obtain 3.93 g of Intermediate I-6 (Yield: 88%). This compound was identified using HR-MS and NMR. $C_{12}H_8F_3N$ estimated value: 223.0609; measured value 223.0901

$^1H$ NMR ($CDCl_3$, 400 MHz) δ (ppm) 7.34-7.26 (m, 2H), 7.04-7.00 (m, 3H), 6.99-6.92 (m, 1H), 6.87-6.77 (m, 1H), 5.62 (s, 1H)

Synthesis Example 8

Synthesis of Intermediate I-7

3.45 g (15.0 mmol) of Intermediate I-6, 2.83 g (10.0 mmol) of 4-bromoiodobenzene, 0.18 g (0.2 mmol) of $Pd_2(dba)_3$, 0.04 g (0.4 mmol) of $PtBu_3$, and 1.44 g (15.0 mmol) of KOtBu were dissolved in 40 mL of toluene to obtain a solution, which was then stirred at about 85° C. for about 4 hours. The reaction solution was cooled to room temperature, followed by three times of extraction with 30 mL of water and 30 mL of diethylether. The organic phase was collected, and was dried using magnesium sulfate to evaporate the solvent. The residue was separated and purified using silica gel column chromatography to obtain 2.38 g of Intermediate I-7 (Yield: 63%). This compound was identified using HR-MS and NMR. $C_{18}H_{11}BrF_3N$ estimated value: 377.0027; measured value 377.0023

$^1H$ NMR ($CDCl_3$, 400 MHz) δ (ppm) 7.38-7.31 (m, 2H), 7.30-7.25 (m, 2H), 7.11-7.07 (dt, 1H), 7.06-7.01 (m, 2H), 6.98-6.91 (m, 2H), 6.88-6.85 (m, 2H)

Synthesis Example 9

Synthesis of Intermediate I-8

3.78 g (10.0 mmol) of Intermediate I-7, 2.54 g (10.0 mmol) of bis(pinacolato)diborone, 0.36 g (0.5 mmol) of $PdCl_2(dppf)_2$, and 2.94 g (30.0 mmol) of KOAc were dissolved in 40 mL of DMSO to obtain a solution, which was then stirred at about 80° C. for about 6 hours. The reaction solution was cooled to room temperature, followed by three times of extraction with 50 mL of water and 50 mL of diethylether. The organic phase was collected, and was dried using magnesium sulfate to evaporate the solvent. The residue was separated and purified using silica gel column chromatography to obtain 3.40 g of Intermediate I-8 (Yield: 80%). This compound was identified using HR-MS and NMR. $C_{24}H_{23}BF_3NO_2$ estimated value: 425.1774; measured value 425.1769

$^1H$ NMR ($CDCl_3$, 400 MHz) δ (ppm) 7.72-7.68 (m, 2H), 7.32-7.25 (m, 2H), 7.13-7.05 (m, 3H), 6.99-6.85 (m, 4H), 1.35 (s, 12H)

Synthesis Example 10

Synthesis of Compound 11

Compound 11 was synthesized from Intermediate I-4 and Intermediate I-8 in the same manner as in the synthesis of Compound 2. This compound was identified using HR-MS and NMR. $C_{46}H_{27}F_3N_2$ estimated value: 664.2126; measured value [M+1] 665.2124

$^1H$ NMR ($CDCl_3$, 400 MHz) δ (ppm) 8.80-8.78 (d, 1H), 8.44-8.41 (d, 1H), 8.23-8.20 (m, 1H), 8.10-8.07 (d, 1H), 8.04 (s, 1H), 8.00-7.99 (d, 1H), 7.95-7.88 (m, 2H), 7.56-7.53 (m, 2H), 7.91-7.47 (m, 3H), 7.35-7.29 (m, 8H), 6.64-6.60 (m, 1H), 6.45-6.43 (d, 2H), 6.35-6.33 (d, 1H), 5.71-5.70 (d, 1H)

I-9

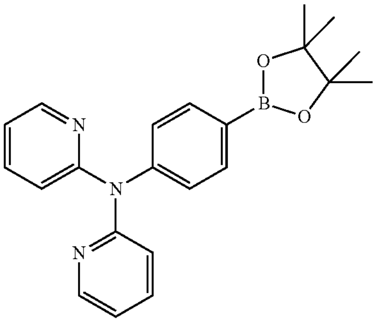

-continued

I-10

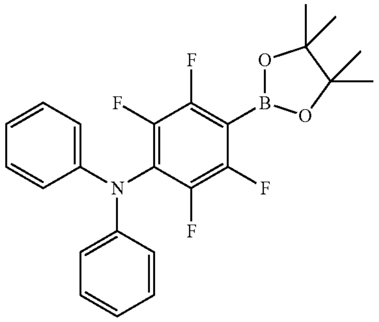

I-11

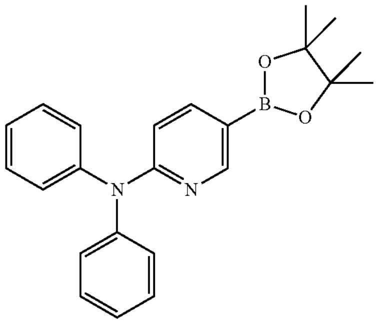

I-12

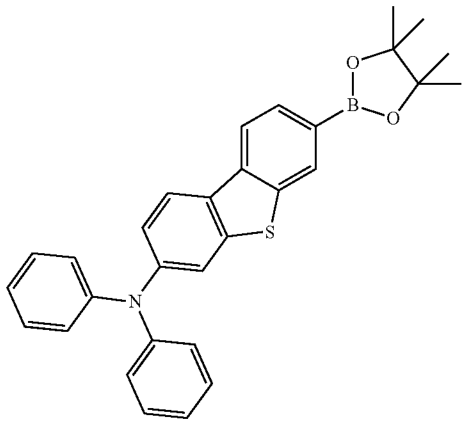

Synthesis Example 11

Synthesis of Intermediate I-9

Intermediate I-9 was synthesized from 2-aminopyridine and 2-bromopyridine in the same manner as in the synthesis of Intermediate I-7 from Intermediate I-6 and Intermediate I-8 from Intermediate I-7. This compound was identified using HR-MS. $C_{22}H_{24}BN_3O_2$ estimated value: 373.1962; measured value 373.1956

$^1H$ NMR ($CDCl_3$, 400 MHz) δ (ppm) 8.22-8.21 (d, 2H), 7.96-7.94 (d, 2H), 7.55-7.51 (t, 2H), 7.36-7.34 (d, 4H), 6.93-6.91 (t, 2H), 1.34 (s, 12H)

Synthesis Example 12

Synthesis of Intermediate I-10

Intermediate I-10 was synthesized from diphenylamine and 1,4-dibromo-tetrafluorobenzene in the same manner as in the synthesis of Intermediate I-9. This compound was identified using HR-MS. $C_{24}H_{22}BF_1NO_2$ estimated value: 443.1680; measured value 443.1685

$^1H$ NMR ($CDCl_3$, 400 MHz) δ (ppm) 7.37-7.33 (t, 4H), 6.62-6.60 (t, 2H), 5.73-5.71 (d, 4H), 1.35 (s, 12H)

Synthesis Example 13

Synthesis of Intermediate I-11

Intermediate I-11 was synthesized from diphenylamine and 2-bromo-5-iodopyridine in the same manner as in the synthesis of Intermediate I-9. This compound was identified using HR-MS. $C_{23}H_{25}BN_2O_2$ estimated value: 372.2009; measured value 372.2006

$^1H$ NMR ($CDCl_3$, 400 MHz) δ (ppm) 8.82 (s, 1H), 7.91-7.89 (d, 1H), 7.50-7.48 (m, 5H), 7.00-6.97 (t, 2H), 6.95-6.91 (d, 4H), 6.49-6.47 (d, 1H), 1.33 (s, 12H)

Synthesis Example 14

Synthesis of Intermediate I-12

Intermediate I-12 was synthesized from diphenylamine and 3,7-dibromo-dibenzothiophene in the same manner as in the synthesis of Intermediate I-9. This compound was identified using HR-MS. $C_{30}H_{28}BNO_2S$ estimated value: 477.1934; measured value 477.1931

$^1H$ NMR ($CDCl_3$, 400 MHz) δ (ppm) 8.28-8.25 (d, 2H), 8.02-8.00 (d, 1H), 7.72-7.70 (d, 1H), 7.56 (s, 1H), 7.33-7.29 (t, 4H), 7.00-6.98 (d, 1H), 6.64-6.62 (t, 2H), 5.89-5.86 (d, 4H), 1.35 (s, 12H)

Synthesis Example 15

Synthesis of Compound 24

Compound 24 was synthesized from Intermediate I-4 and Intermediate I-9 in the same manner as in the synthesis of Compound 2. This compound was identified using HR-MS. $C_{44}H_{28}N_4$ estimated value: 612.2314; measured value [M+1] 613.2310

$^1H$ NMR ($CDCl_3$, 400 MHz) δ (ppm) 8.80 (d, 1H), 8.44-8.41 (d, 1H), 8.23-8.20 (m, 2H), 8.10-8.07 (d, 1H), 8.04 (s, 1H), 8.00-7.98 (d, 1H), 7.94-7.88 (m, 2H), 7.58-7.51 (m, 3H), 7.50-7.47 (m, 6H), 7.37-7.29 (m, 6H), 7.01-6.97 (m, 2H), 6.91-6.89 (dd, 2H)

Synthesis Example 16

Synthesis of Compound 34

Compound 24 was synthesized from Intermediate I-4 and Intermediate I-10 in the same manner as in the synthesis of Compound 2. This compound was identified using HR-MS. $C_{46}H_{26}F_4N_2$ estimated value: 682.2032; measured value [M+1] 683.2029

$^1H$ NMR ($CDCl_3$, 400 MHz) δ (ppm) 8.79-8.77 (d, 1H), 8.40-8.39 (d, 1H), 8.25-8.22 (m, 1H), 8.14-8.11 (d, 1H), 8.06-8.01 (m, 2H), 7.93-7.91 (d, 1H), 7.59-7.57 (d, 1H), 7.51-7.46 (m, 4H), 7.35-7.31 (m, 8H), 6.64-6.60 (t, 2H), 5.73-5.71 (m, 4H)

Synthesis Example 17

Synthesis of Compound 45

Compound 24 was synthesized from Intermediate I-4 and Intermediate I-11 in the same manner as in the synthesis of Compound 2. This compound was identified using HR-MS. $C_{45}H_{29}N_3$ estimated value: 611.2361; measured value [M+1] 612.2357

$^1H$ NMR ($CDCl_3$, 400 MHz) δ (ppm) 8.93-8.91 (m, 1H), 8.77-8.75 (d, 1H), 8.43-8.42 (d, 1H), 8.23-8.19 (m, 2H), 8.17-8.11 (m, 3H), 8.07-8.01 (m, 3H), 5.55-7.46 (m, 8H), 7.33-7.26 (m, 3H), 7.01-6.96 (m, 2H), 6.93-6.90 (m, 4H), 6.61-6.58 (d, 1H)

Synthesis Example 18

Synthesis of Compound 48

Compound 24 was synthesized from Intermediate I-4 and Intermediate I-12 in the same manner as in the synthesis of Compound 2. This compound was identified using HR-MS. $C_{52}H_{32}N_2S$ estimated value: 716.2286; measured value [M+1] 717.2281

$^1H$ NMR ($CDCl_3$, 400 MHz) δ (ppm) 8.74-8.72 (d, 1H), 8.39-8.37 (d, 1H), 8.22-8.17 (m, 3H), 8.13-8.04 (m, 5H), 7.98-7.96 (d, 1H), 7.72-7.70 (d, 1H), 7.54-7.45 (m, 5H), 7.37-7.27 (m, 8H), 7.04-6.98 (m, 1H), 6.66-6.60 (m, 2H), 6.23-6.21 (d, 4H)

Synthesis Example 19

Synthesis of Compound 55

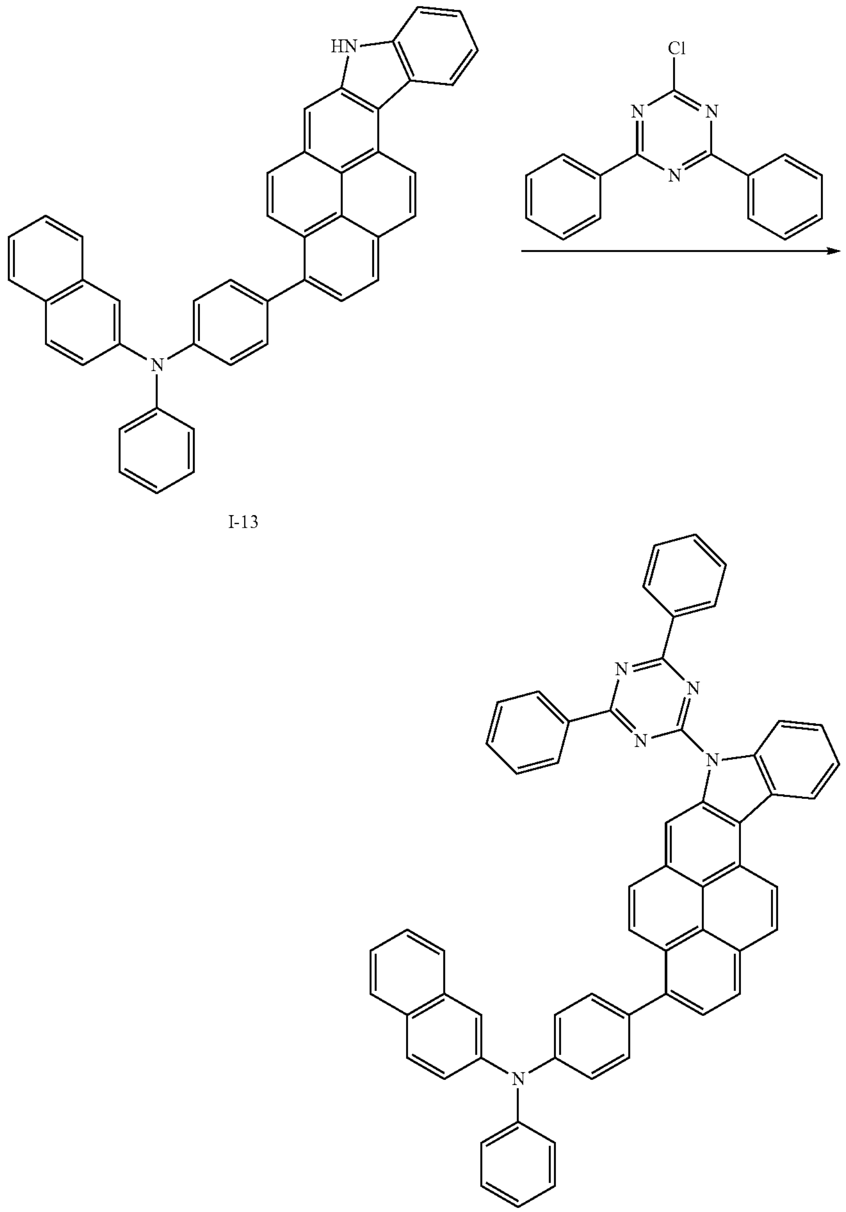

I-13

55

2-bromonaphthalene and aniline were reacted in the same manner as in the synthesis of Intermediate I-8 to synthesize a secondary amine, and then the secondary amine was Suzuki-reacted with 4-bromo-1-iodobenzene. Then, the reaction product was reacted with Bis(pinacolato)diborone and $PdCl_2(dppf)_2$ to synthesize a boron compound. Then, the boron compound and Intermediate I-3 were reacted to synthesize Intermediate I-13.

2.92 g (5.0 mmol) of Intermediate I-13 was dissolved in 20 ml of DMF 20 and then the solution was slowly added to a solution prepared by dissolving 0.6 g (15.0 mmol) of 60% sodium hydride (NaH) in 10 ml of DMF for 10 minutes. After one hour at room temperature, a solution prepared by dissolving 2.67 g (10.0 mmol) of 2-chloro-4,6-diphenyl-(1,3,5)-triazine in 10 ml of DMF was slowly added thereto for 30 minutes and the mixture was stirred at room temperature for 3 hours. After the reaction was finished, the reaction solution was extracted three times with water and 60 ml of diethylether. The organic phase was collected, and was dried using magnesium sulfate to evaporate the solvent. The residue was separated and purified using silica gel column chromatography to obtain 3.83 g (Yield 47%) of Compound 55. This compound was identified using HR-MS. $C_{59}H_{37}N_5$ estimated value: 815.3049; measured value [M+1] 816.3044

$^1$H NMR ($CDCl_3$, 400 MHz) δ (ppm) 8.85-8.78 (m, 3H), 8.59-8.56 (m, 4H), 8.44-8.41 (d, 1H), 8.22-8.21 (d, 1H), 8.08-7.98 (m, 2H), 7.94-7.86 (m, 3H), 7.70-7.62 (m, 2H), 7.57-7.50 (m, 3H), 7.47-7.25 (m, 11H), 7.16-7.11 (m, 1H), 6.87-6.79 (m, 1H), 6.63-6.59 (m, 3H), 6.12-6.09 (m, 2H)

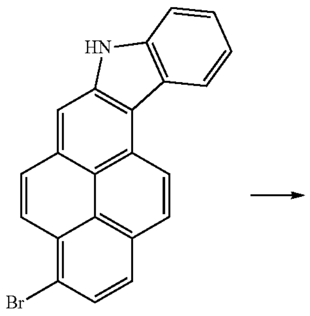

I-3

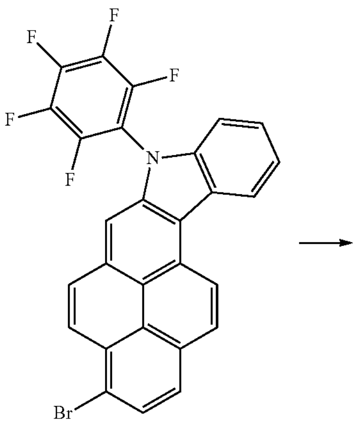

I-14

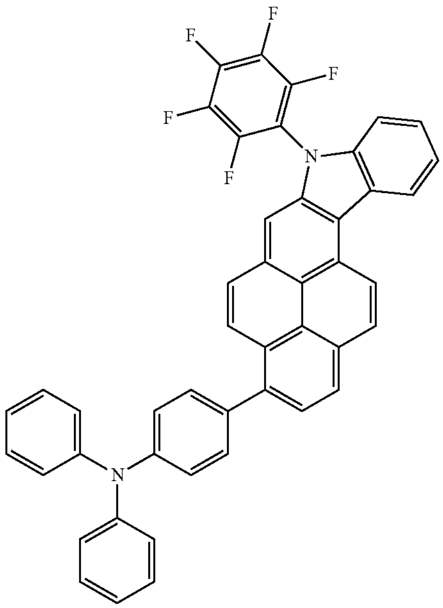

57

Synthesis Example 20

Synthesis of Compound 57

Intermediate I-14 was synthesized from bromopentafluorobenzene in the same manner as in the synthesis of Intermediate I-4, and Compound 57 was synthesized from Intermediate I-14 and Intermediate I-5 in the same manner as in the synthesis of Compound 2. This compound was identified using HR-MS. $C_{45}H_{25}F_5N_2$ estimated value: 700.1938; measured value [M+1] 701.1932

$^1$H NMR ($CDCl_3$, 400 MHz) δ (ppm) 8.70-8.68 (d, 1H), 8.34-8.31 (d, 1H), 8.16-8.14 (m, 1H), 8.05-8.02 (m, 2H), 7.80-7.78 (d, 1H), 7.70-7.58 (m, 2H), 7.41-7.23 (m, 8H), 6.86-6.82 (m, 3H), 6.65-6.61 (m, 2H), 5.99-5.97 (m, 4H)

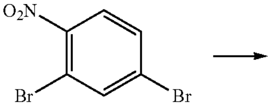

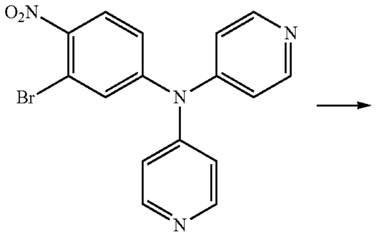

I-15

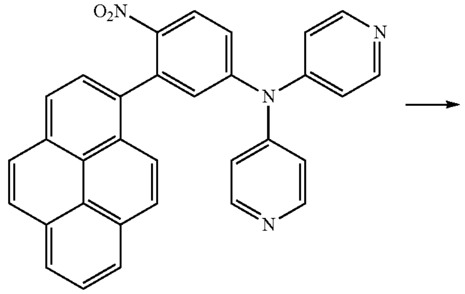

I-16

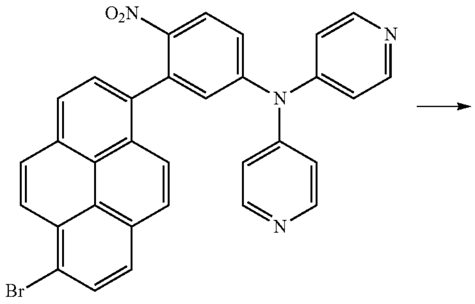

I-17

-continued

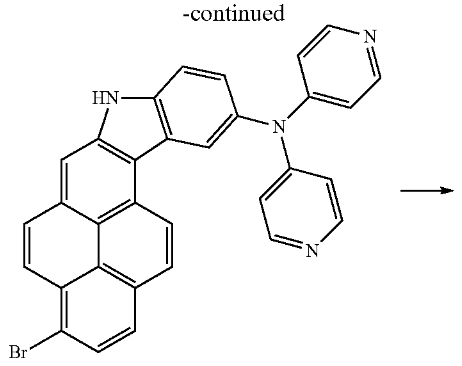

I-18

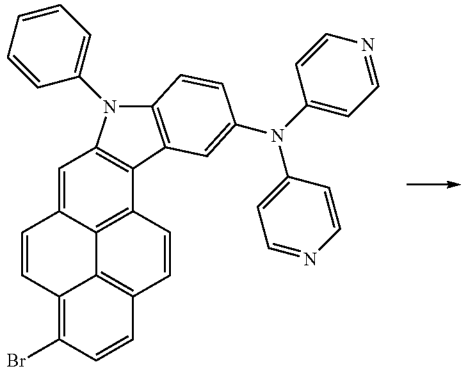

I-19

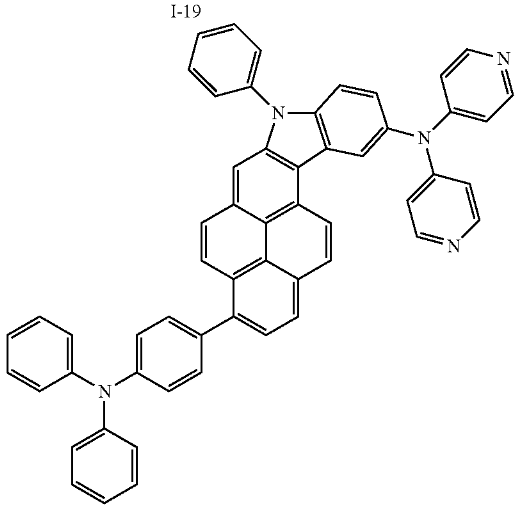

73

Synthesis Example 21

Synthesis of Intermediate I-15

5.62 g (20.0 mmol) of 2-4,Dibromo-1-nitrobenzene, 1.71 g (10.0 mmol) of di-4-pyridylamine, 0.18 g (0.2 mmol) of $Pd_2$(d ba)$_3$, 0.04 g (0.2 mmol) of $PtBu_3$, and 1.44 g (15.0 mmol) of NaOtBu were mixed and 40 ml of toluene was added to the mixture and stirred at a temperature of 85° C. for 5 hours. The reaction solution was cooled to room temperature, followed by three times of extraction with 50 mL of water and 50 mL of diethylether. The organic phase was collected, and was dried using magnesium sulfate to evaporate the solvent. The residue was separated and purified using silica gel column chromatography to obtain 1.63 g of Intermediate I-15 (Yield 44%). This compound was identified using HR-MS. $C_{16}H_{11}BrN_4O_2$ estimated value: 370.0065; measured value 370.0061

$^1$H NMR ($CDCl_3$, 400 MHz) δ (ppm) 8.20-8.18 (d, 1H), 8.17-8.12 (m, 4H), 7.64-7.62 (m, 1H), 6.98-6.96 (m, 4H), 6.51-6.47 (dd, 1H)

Synthesis Example 22

Synthesis of Intermediate I-16

Intermediate I-16 was synthesized from Intermediate I-15 in the same manner as in the synthesis of Intermediate I-1. This compound was identified using HR-MS. $C_{32}H_{20}N_4O_2$ estimated value: 492.1586; measured value 492.1583

$^1$H NMR ($CDCl_3$, 400 MHz) δ (ppm) 8.28-8.20 (m, 3H), 8.18-8.12 (m, 4H), 8.09-8.00 (m, 4H), 7.99-7.75 (m, 2H), 7.71-7.69 (d, 1H), 7.47-7.43 (m, 1H), 7.23-7.19 (dd, 1H), 6.70-6.66 (m, 4H)

Synthesis Example 23

Synthesis of Intermediate I-17

Intermediate I-17 was synthesized from Intermediate I-16 in the same manner as in the synthesis of Intermediate I-2. This compound was identified using HR-MS. $C_{32}H_{19}BrN_4O_2$ estimated value: 570.0691; measured value 570.0686

$^1$H NMR ($CDCl_3$, 400 MHz) δ (ppm) 8.85-8.83 (d, 1H), 8.35-8.33 (d, 1H), 8.28-8.21 (m, 3H), 8.18-8.12 (m, 4H), 8.08-8.02 (dd, 1H), 7.95-7.89 (m, 2H), 7.71-7.69 (d, 1H), 7.47-7.43 (m, 1H), 723-7.21 (dd, 1H), 6.78-6.76 (m, 4H)

Synthesis Example 24

Synthesis of Intermediate I-18

Intermediate I-18 was synthesized from Intermediate I-17 in the same manner as in the synthesis of Intermediate I-3. This compound was identified using HR-MS. $C_{32}H_{19}BrN_4$ estimated value: 538.0793; measured value 538.0787

$^1$H NMR ($CDCl_3$, 400 MHz) δ (ppm) 9.8 (s, 1H), 8.99-8.97 (d, 1H), 8.85-8.83 (d, 1H), 8.50-8.36 (m, 2H), 8.25-8.12 (m, 5H), 7.99-7.95 (m, 2H), 7.46-7.42 (m, 2H), 7.34-7.29 (m, 1H), 6.93-6.82 (m, 4H)

Synthesis Example 25

Synthesis of Intermediate I-19

Intermediate I-19 was synthesized from Intermediate I-18 in the same manner as in the synthesis of Intermediate I-4. This compound was identified using HR-MS. $C_{38}H_{23}BrN_4$ estimated value: 614.1106; measured value 614.1102

$^1$H NMR ($CDCl_3$, 400 MHz) δ (ppm) 9.04-9.02 (d, 1H), 8.85-8.83 (d, 1H), 8.46-8.44 (d, 1H), 8.36-8.34 (d, 1H), 8.28 (s, 1H), 8.18-8.12 (m, 4H), 8.03-7.98 (m, 2H), 7.79-7.76 (m, 1H), 7.68-7.60 (m, 1H), 7.53-7.44 (m, 5H), 7.37-7.30 (m, 1H), 6.82-6.79 (m, 4H)

Synthesis Example 26

Synthesis of Compound 73

Compound 73 was synthesized from Intermediate I-5 and Intermediate I-19 in the same manner as in the synthesis of Compound 2. This compound was identified using HR-MS. $C_{56}H_{37}N_5$ estimated value: 779.3049; measured value [M+1] 780.3042
$^1H$ NMR ($CDCl_3$, 400 MHz) δ (ppm) 8.95-8.92 (d, 1H), 8.44-8.41 (d, 1H), 8.21-8.10 (m, 5H), 8.05-7.99 (m, 2H), 7.96-7.88 (m, 2H), 7.79-7.76 (m, 1H), 7.66-7.62 (m, 1H), 7.53-7.45 (m, 4H), 7.36-7.25 (m, 8H), 6.92-6.88 (m, 4H), 6.74-6.70 (m, 2H), 6.54-6.50 (m, 2H), 6.02-6.98 (m, 4H)
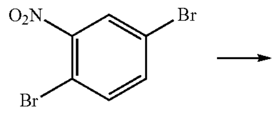
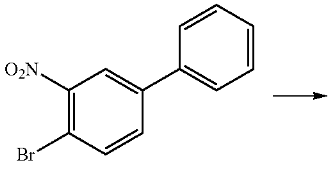
I-20
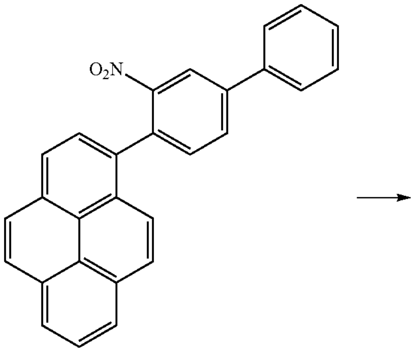
I-21
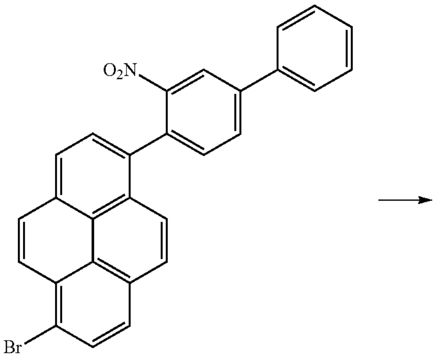
I-22
-continued
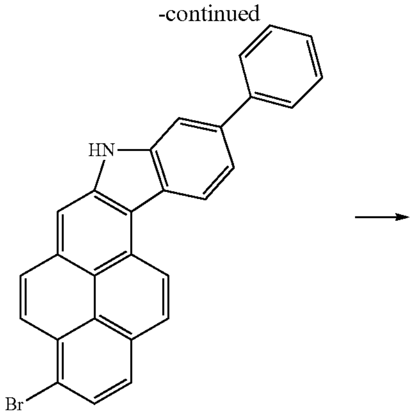
I-23
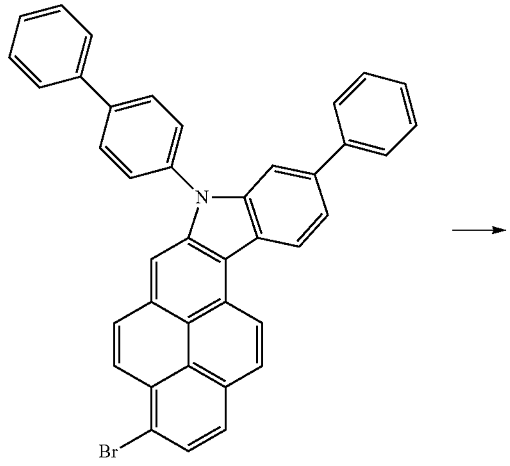
I-24
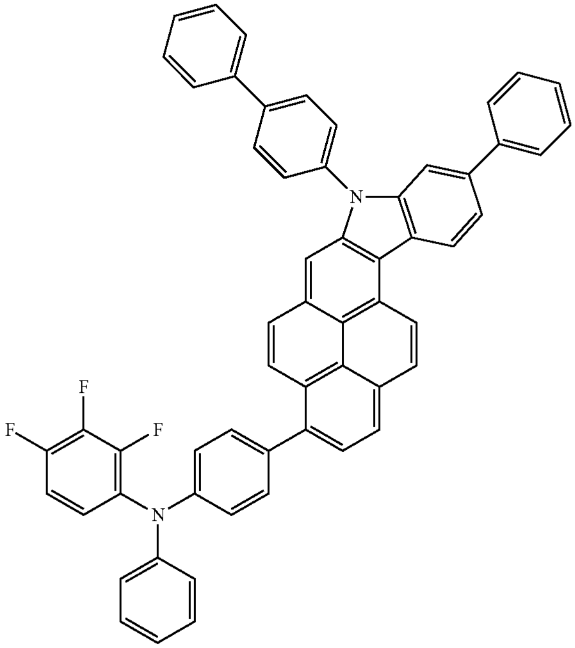
82

Synthesis Example 27

Synthesis of Intermediate I-20

5.62 g (20.0 mmol) of 1,4-Dibromo-2-nitrobenzene, 1.22 g (10.0 mmol) of phenylboronic acid, 0.58 g (0.5 mmol) of $PdPPh_3$, and 4.14 g (30.0 mmol) of $K_2CO_3$ were dissolved in 40 ml of $THF/H_2O$ (2/1) and the mixture was stirred at a temperature of 80° C. for 5 hours. The reaction solution was cooled to room temperature, followed by three times of extraction with 50 mL of water and 50 mL of diethylether. The organic phase was collected, and was dried using magnesium sulfate to evaporate the solvent. The residue was separated and purified using silica gel column chromatography to obtain 1.33 g (Yield 48%) of Intermediate I-20. This compound was identified using HR-MS. $C_{12}H_8BrNO_2$ estimated value: 276.9738; measured value 276.9732

$^1H$ NMR ($CDCl_3$, 400 MHz) δ (ppm) 8.15-8.13 (m, 1H), 7.82-7.76 (m, 2H), 7.49-7.46 (d, 1H), 7.34-7.28 (m, 1H), 7.21-7.13 (m, 2H), 7.11-7.08 (dd, 1H)

Synthesis Example 28

Synthesis of Intermediate I-21

Intermediate I-21 was synthesized from Intermediate I-20 in the same manner as in the synthesis of Intermediate I-16. This compound was identified using HR-MS. $C_{28}H_{17}NO_2$ estimated value: 399.1259; measured value 399.1253

$^1H$ NMR ($CDCl_3$, 400 MHz) δ (ppm) 8.28-8.26 (d, 1H), 8.11-8.01 (m, 6H), 7.99-7.97 (d, 1H), 7.89-7.86 (d, 1H), 7.73-7.66 (m, 2H), 7.42-7.38 (m, 1H), 7.36-7.28 (m, 1H), 7.19-7.15 (t, 2H), 6.94-6.92 (dd, 1H), 6.74-6.68 (dd, 1H)

Synthesis Example 29

Synthesis of Intermediate I-22

Intermediate I-22 was synthesized from Intermediate I-21 in the same manner as in the synthesis of Intermediate 1-17. This compound was identified using HR-MS. $C_{28}H_{16}BrNO_2$ estimated value: 477.0364; measured value 477.0359

$^1H$ NMR ($CDCl_3$, 400 MHz) δ (ppm) 8.85-8.83 (d, 1H), 8.35-8.33 (d, 1H), 8.24-8.22 (d, 1H), 8.15-8.08 (m, 2H), 7.95-7.84 (m, 3H), 7.74-7.66 (m, 2H), 7.42-7.36 (m, 1H), 7.34-7.28 (m, 1H), 7.19-7.14 (m, 2H), 6.94-6.93 (d, 1H), 6.78-6.69 (m, 1H)

Synthesis Example 30

Synthesis of Intermediate I-23

Intermediate I-13 was synthesized from Intermediate I-22 in the same manner as in the synthesis of Intermediate I-18. This compound was identified using HR-MS. $C_{28}H_{16}BrN$ estimated value: 445.0466; measured value 445.0461

$^1H$ NMR ($CDCl_3$, 400 MHz) δ (ppm) 9.8 (s, 1H), 8.84-8.80 (m, 2H), 8.50-8.46 (d, 1H), 8.40-8.36 (d, 1H), 8.26-8.19 (m, 1H), 8.05-7.95 (m, 4H), 7.72-7.65 (m, 3H), 7.50-7.46 (dt, 2H), 7.38-7.32 (m, 1H)

Synthesis Example 31

Synthesis of Intermediate I-24

Intermediate I-24 was synthesized from Intermediate I-24 and 4-bromobiphenyl in the same manner as in the synthesis of Intermediate I-19. This compound was identified using HR-MS. $C_{40}H_{24}BrN$ estimated value: 597.1092; measured value 597.1085

$^1H$ NMR ($CDCl_3$, 400 MHz) δ (ppm) 8.90-8.81 (m, 2H), 8.46-8.44 (d, 1H), 8.36-8.28 (m, 2H), 8.13-8.07 (m, 2H), 8.03-7.95 (m, 2H), 7.61-7.52 (m, 4H), 7.50-7.44 (m, 2H), 7.42-7.28 (m, 7H), 6.58-6.54 (m, 2H)

Synthesis Example 32

Synthesis of Compound 82

Compound 82 was synthesized from Intermediate I-8 and Intermediate I-24 in the same manner as in the synthesis of Compound 73. This compound was identified using HR-MS. $C_{58}H_{35}F_3N$ estimated value: 816.2752; measured value [M+1] 817.2746

$^1H$ NMR ($CDCl_3$, 400 MHz) δ (ppm) 8.80-8.76 (d, 1H), 8.46-8.43 (d, 1H), 8.32-8.29 (dd, 1H), 8.6-8.06 (m, 2H), 8.02-7.89 (m, 4H), 7.76-7.52 (m, 4H), 7.50-7.46 (m, 2H), 7.43-7.28 (m, 12H), 6.84-6.63 (m, 3H), 6.55-6.52 (m, 2H), 6.45-6.43 (d, 1H), 6.12-6.09 (m, 2H)

Example 1

To manufacture an anode, a corning 15 Ω/cm² (1200 Å) ITO glass substrate was cut to a size of 50 mm×50 mm×0.7 mm and then sonicated in isopropyl alcohol and pure water each for five minutes, and then cleaned by irradiation of ultraviolet rays for 30 minutes and exposure to ozone. The resulting glass substrate was loaded into a vacuum deposition device.

Then, 2-TNATA, which is a HIL material, was vacuum-deposited on the glass substrate to form a HIL having a thickness of about 600 Å. Then, 4,4'-bis[N-(1-naphthyl)-N-phenylamino]biphenyl (NPB), which is a hole transporting compound, was vacuum-deposited on the HIL to form a HTL having a thickness of about 300 Å.

A blue fluorescent host 9,10-di-naphthalene-2-yl-anthracene (ADN) and Compound 2 of Synthesis Example 1, which is a blue fluorescent dopant, were simultaneously deposited on the HTL with a weight ratio of 98:2 to form an EML having a thickness of 300 Å.

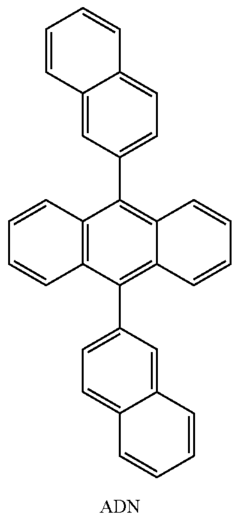 [SMILES: c1ccc2cc(-c3c4ccccc4c(-c4ccc5ccccc5c4)c4ccccc34)ccc2c1]

ADN

Then, Alq3 was deposited on the EML to form an ETL having a thickness of 300 Å, and then LiF, which is a halogenated alkali metal, was deposited on the ETL to form an EIL having a thickness of 10 Å. Then, Al was vacuum-deposited on the EIL to form a cathode having a thickness of 3000 Å, thereby forming an LiF/Al electrode and completing the manufacture of an organic light-emitting device.

The organic light-emitting device had a driving voltage of 6.57V at a current density of 50 mA/cm$^2$, a high luminosity of 2830 cd/m$^2$, a luminescent efficiency of 5.66 cd/A, and a half-lifespan of 263 hours at 100 mA/cm$^2$.

Example 2

An organic light-emitting device was manufactured in the same manner as in Example 1, except that Compound 11 was used, instead of Compound 2, to form the EML.

The organic light-emitting device had a driving voltage of 6.45V at a current density of 50 mA/cm$^2$, a high luminosity of 2970 cd/m$^2$, a luminescent efficiency of 5.94 cd/A, and a half-lifespan of 225 hours at 100 mA/cm$^2$.

Example 3

An organic light-emitting device was manufactured in the same manner as in Example 1, except that Compound 24 was used, instead of Compound 2, to form the EML.

The organic light-emitting device had a driving voltage of 6.32V at a current density of 50 mA/cm$^2$, a high luminosity of 2310 cd/m$^2$, a luminescent efficiency of 4.62 cd/A, and a half-lifespan of 201 hours at 100 mA/cm$^2$.

Example 4

An organic light-emitting device was manufactured in the same manner as in Example 1, except that Compound 34 was used, instead of Compound 2, to form the EML.

The organic light-emitting device had a driving voltage of 6.50V at a current density of 50 mA/cm$^2$, a high luminosity of 2785 cd/m$^2$, a luminescent efficiency of 5.57 cd/A, and a half-lifespan of 220 hours at 100 mA/cm$^2$.

Example 5

An organic light-emitting device was manufactured in the same manner as in Example 1, except that Compound 45 was used, instead of Compound 2, to form the EML.

The organic light-emitting device had a driving voltage of 6.42V at a current density of 50 mA/cm$^2$, a high luminosity of 2567 cd/m$^2$, a luminescent efficiency of 5.13 cd/A, and a half-lifespan of 210 hours at 100 mA/cm$^2$.

Example 6

An organic light-emitting device was manufactured in the same manner as in Example 1, except that Compound 48 was used, instead of Compound 2, to form the EML.

The organic light-emitting device had a driving voltage of 6.35V at a current density of 50 mA/cm$^2$, a high luminosity of 2473 cd/m$^2$, a luminescent efficiency of 4.95 cd/A, and a half-lifespan of 195 hours at 100 mA/cm$^2$.

Example 7

An organic light-emitting device was manufactured in the same manner as in Example 1, except that Compound 55 was used, instead of Compound 2, to form the EML.

The organic light-emitting device had a driving voltage of 6.22V at a current density of 50 mA/cm$^2$, a high luminosity of 2657 cd/m$^2$, a luminescent efficiency of 5.31 cd/A, and a half-lifespan of 183 hours at 100 mA/cm$^2$.

Example 8

An organic light-emitting device was manufactured in the same manner as in Example 1, except that Compound 57 was used, instead of Compound 2, to form the EML.

The organic light-emitting device had a driving voltage of 6.62V at a current density of 50 mA/cm$^2$, a high luminosity of 2796 cd/m$^2$, a luminescent efficiency of 5.59 cd/A, and a half-lifespan of 231 hours at 100 mA/cm$^2$.

Example 9

An organic light-emitting device was manufactured in the same manner as in Example 1, except that Compound 73 was used, instead of Compound 2, to form the EML.

The organic light-emitting device had a driving voltage of 6.26V at a current density of 50 mA/cm$^2$, a high luminosity of 2640 cd/m$^2$, a luminescent efficiency of 5.28 cd/A, and a half-lifespan of 203 hours at 100 mA/cm$^2$.

Example 10

An organic light-emitting device was manufactured in the same manner as in Example 1, except that Compound 82 was used, instead of Compound 2, to form the EML.

The organic light-emitting device had a driving voltage of 6.44V at a current density of 50 mA/cm$^2$, a high luminosity of 2940 cd/m$^2$, a luminescent efficiency of 5.88 cd/A, and a half-lifespan of 216 hours at 100 mA/cm$^2$.

Comparative Example 1

An organic light-emitting device was manufactured in the same manner as in Example 1, except that a blue fluorescent dopant 1,4-bis-(2,2-diphenylvinyl)biphenyl (DPVBi) was used, instead of Compound 2, to form the EML.

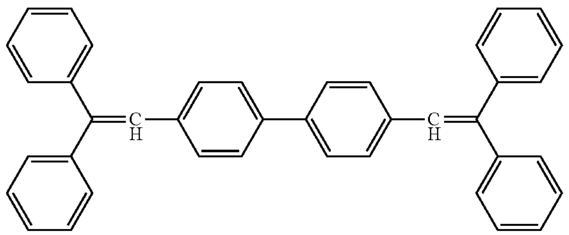

DPVBi

The organic light-emitting device had a driving voltage of 7.85V at a current density of 50 mA/cm$^2$, a luminosity of 1560 cd/m$^2$, a luminescent efficiency of 3.12 cd/A, and a half-lifespan of 113 hours at 100 mA/cm$^2$.

The organic light-emitting devices manufactured using the heterocyclic compounds represented by Formula 1 according to embodiments as blue dopants for EML had improved driving voltages and much higher 1-V-L characteristics, as compared to those manufactured using DPVBi. In particular, the organic light-emitting devices according to the embodiments had markedly improved lifetimes. These results are shown in Table 1 below.

TABLE 1

| | EML material | Driving voltage (V) | Current density ($mA/cm^2$) | Luminosity ($cd/m^2$) | Luminescent efficiency (cd/A) | Emitting light color | Half life-span (hr @100 $mA/cm^2$) |
|---|---|---|---|---|---|---|---|
| Example 1 | Compound 2 | 6.57 | 50 | 2,830 | 5.66 | blue | 263 hr |
| Example 2 | Compound 11 | 6.45 | 50 | 2,970 | 5.94 | blue | 225 hr |
| Example 3 | Compound 24 | 6.32 | 50 | 2,310 | 4.62 | blue | 201 hr |
| Example 4 | Compound 34 | 6.50 | 50 | 2,785 | 5.57 | blue | 220 hr |
| Example 5 | Compound 45 | 6.42 | 50 | 2,567 | 5.13 | blue | 210 hr |
| Example 6 | Compound 48 | 6.35 | 50 | 2,473 | 4.95 | blue | 195 hr |
| Example 7 | Compound 55 | 6.22 | 50 | 2,657 | 5.31 | blue | 183 hr |
| Example 8 | Compound 57 | 6.62 | 50 | 2,796 | 5.59 | blue | 231 hr |
| Example 9 | Compound 73 | 6.26 | 50 | 2,640 | 5.28 | bluish green | 203 hr |
| Example 10 | Compound 82 | 6.44 | 50 | 2,940 | 5.88 | blue | 216 hr |
| Comparative Example 1 | DPVBi | 7.85 | 50 | 1,560 | 3.12 | blue | 113 hr |

As described above, novel heterocyclic compounds according to the one or more of the above embodiments have good electrical characteristics, good charge transporting capabilities and good emission characteristics, and may be used to prevent crystallization due to high glass transition temperatures ($T_g$). The heterocyclic compounds may also be used as electron transporting materials for most color-fluorescent and phosphorescent devices, such as red, green, blue, and white fluorescent and phosphorescent devices, or as red, green, blue or white-light emitting materials. Thus, an organic light-emitting device with high-efficiency, low-driving voltage, high luminance and long lifespan may be manufactured using the heterocyclic compounds.

While the present embodiments have been particularly shown and described with reference to example embodiments thereof, it will be understood by those of ordinary skill in the art that various changes in form and details may be made therein without departing from the spirit and scope of the present embodiments as defined by the following claims.

What is claimed is:

1. A heterocyclic compound represented by Formula 1 below:

Formula 1

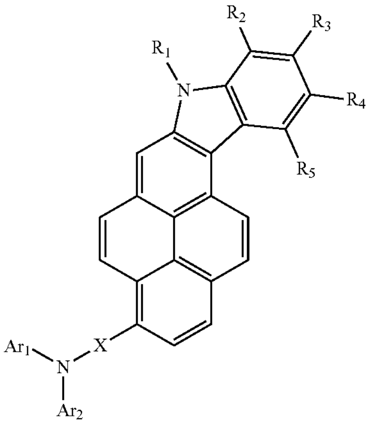

wherein $R_1$ through $R_5$ are each independently a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a substituted or unsubstituted $C_5$-$C_{60}$ aryloxy group, a substituted or unsubstituted $C_5$-$C_{60}$ arylthio group, a substituted or unsubstituted $C_5$-$C_{60}$ aryl group, an amino group substituted with a $C_5$-$C_{60}$ aryl or $C_3$-$C_{60}$ heteroaryl group, a substituted or unsubstituted $C_3$-$C_{60}$ heteroaryl group, a substituted or unsubstituted $C_6$-$C_{60}$ condensed polycyclic group, a halogen atom, a cyano group, a nitro group, a hydroxyl group, or a carboxyl group;

$Ar_1$ and $Ar_2$ are each independently a substituted or unsubstituted $C_3$-$C_{50}$ cycloalkyl group, a substituted or unsubstituted $C_5$-$C_{60}$ aryloxy group, a substituted or unsubstituted $C_5$-$C_{60}$ arythio group, a substituted or unsubstituted $C_5$-$C_{60}$ aryl group, an amino group substituted with a $C_5$-$C_{60}$ aryl or $C_3$-$C_{60}$ heteroaryl group, a substituted or unsubstituted $C_3$-$C_{60}$ heteroaryl group, or a substituted or unsubstituted $C_6$-$C_{60}$ condensed polycyclic group; and X is a divalent linking group represented by $-(Ar_3)_n-$ wherein $Ar_3$ is a substituted or unsubstituted $C_5$-$C_{60}$ arylene group, a substituted or unsubstituted $C_3$-$C_{60}$ heteroarylene group, or a substituted or unsubstituted $C_6$-$C_{60}$ condensed polycyclic group, and n is an integer from 1 to 10, wherein n groups of $Ar_3$ are identical to or different from each other, and wherein when n is greater than 1, at least two adjacent groups of the n $Ar_3$ groups are fused or linked to each other by a single bond.

2. The heterocyclic compound of claim 1, wherein $R_1$ to $R_5$ in Formula 1 are each independently a hydrogen atom, a deuterium atom, a cyano group, a halogen atom, an unsubstituted $C_1$-$C_{20}$ alkyl group, a substituted $C_1$-$C_{20}$ alkyl group with at least one fluorine (—F) substituent, a substituted or unsubstituted $C_5$-$C_{20}$ aryl group, or a substituted or unsubstituted $C_3$-$C_{20}$ heteroaryl group.

3. The heterocyclic compound of claim 1, wherein $R_1$ to $R_5$ in Formula 1 are each independently a hydrogen atom, a deuterium atom, a halogen atom, a cyano group, a substituted or unsubstituted $C_1$-$C_{20}$ alkyl group, or groups represented by Formulae 2a to 2i below:

formula 2a

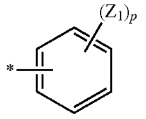

formula 2b

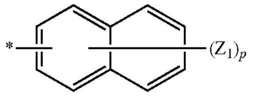

formula 2c

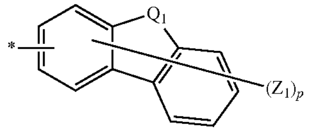

formula 2d

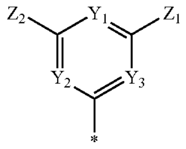

formula 2e

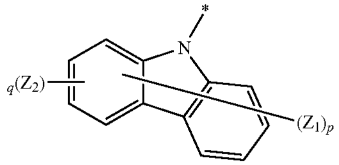

formula 2f

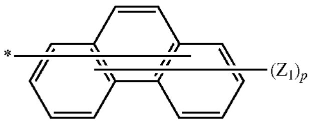

formula 2g

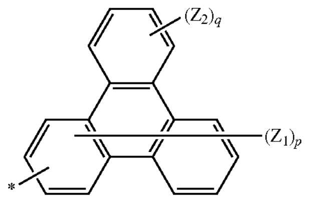

formula 2h

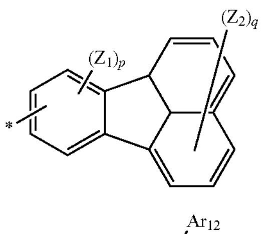

formula 2i

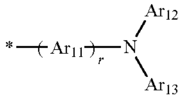

wherein, in Formulae 2a to 2i, $Q_1$ is a linking group represented by —$C(R_6)(R_7)$—, —$N(R_6)$—, —S—, or —O—;

$Y_1$, $Y_2$, and $Y_3$ are each independently a linking group represented by —N═ or —$C(R_8)$═;

$Z_1$, $Z_2$, $Ar_{12}$, $Ar_{13}$, $R_6$, $R_7$, and $R_8$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group;

$Ar_{11}$ is a substituted or unsubstituted $C_1$-$C_{20}$ alkylene group, a substituted or unsubstituted $C_5$-$C_{20}$ arylene group, or a substituted or unsubstituted $C_3$-$C_{20}$ heteroarylene group;

p is an integer from 1 to 12;

q is an integer from 1 to 12;

r is an integer from 0 to 5; and

* indicates a binding site.

4. The heterocyclic compound of claim 1, wherein $R_1$ to $R_5$ in Formula 1 are each independently a hydrogen atom, a deuterium atom, a halogen atom, a cyano group, a methyl group, an ethyl group, a propyl group, a butyl group, a pentyl group, or groups represented by Formulae 3a to 31 below:

formula 3a

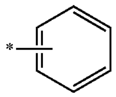

formula 3b

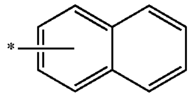

formula 3c

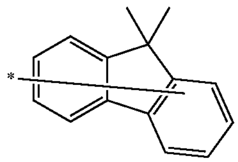

formula 3d

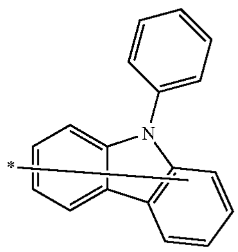

formula 3e

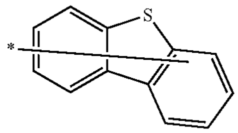

formula 3f

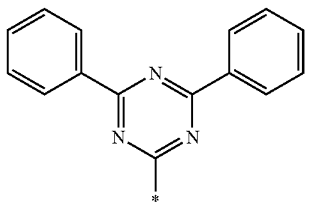

-continued formula 3g

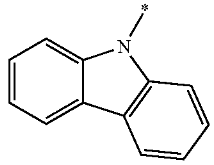

formula 3h

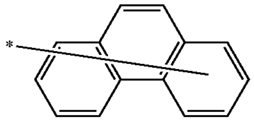

formula 3i

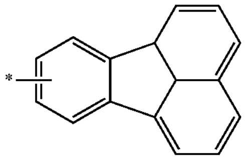

formula 3j

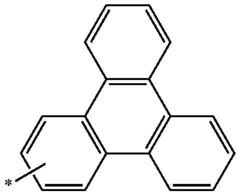

formula 3k

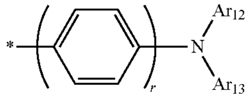

formula 3l

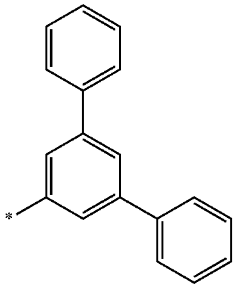

wherein in Formula 3a to 31, $Ar_{12}$ and $Ar_{13}$ are each independently an unsubstituted aryl group, a substituted or unsubstituted $C_3$-$C_{20}$ heteroaryl group, or a substituted or unsubstituted $C_6$-$C_{20}$ condensed polycyclic group;

r is an integer from 0 to 2; and

* indicates a binding site.

5. The heterocyclic compound of claim 1, wherein $R_2$ and $R_5$ in Formula 1 are hydrogen atoms; and $R_1$, $R_3$, and $R_4$ are each independently a hydrogen atom, a deuterium atom, a halogen atom, a cyano group, a methyl group, an ethyl group, a propyl group, a butyl group, a pentyl group, or groups represented by Formulae 3a to 3l below:

formula 3a

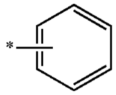

-continued formula 3b

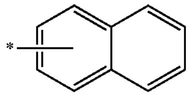

formula 3c

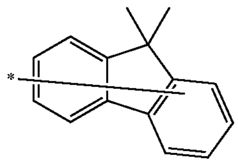

formula 3d

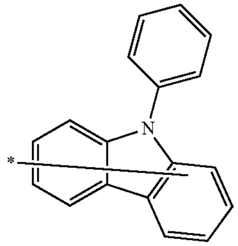

formula 3e

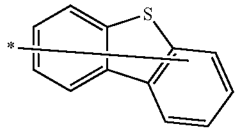

formula 3f

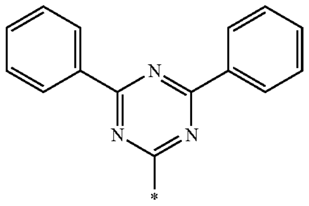

formula 3g

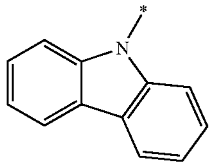

formula 3h

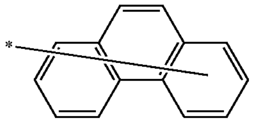

formula 3i

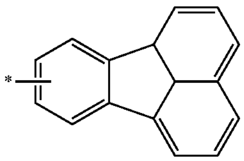

formula 3j

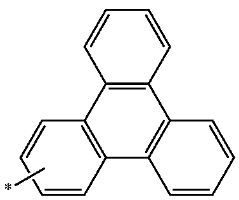

-continued formula 3k

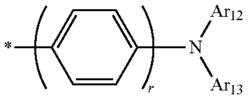

formula 3l

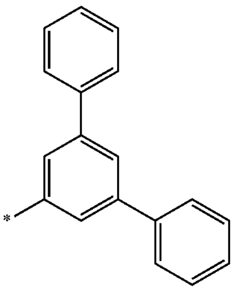

wherein, in Formula 3a to 3l, $Ar_{12}$ and $Ar_{13}$ are each independently an unsubstituted aryl group, a substituted or unsubstituted $C_3$-$C_{20}$ heteroaryl group, or a substituted or unsubstituted $C_6$-$C_{20}$ condensed polycyclic group; r is an integer from 0 to 2; and * indicates a binding site.

6. The heterocyclic compound of claim 1, wherein $R_2$ and $R_5$ are hydrogen atoms;

$R_1$ is a substituted or unsubstituted $C_6$-$C_{20}$ aryl group or a substituted or unsubstituted $C_3$-$C_{20}$ heteroaryl group, $R_3$ is a hydrogen atom or a substituted or unsubstituted $C_6$-$C_{20}$ aryl group, and $R_4$ is a hydrogen atom or an amino group substituted with a $C_3$-$C_{20}$ heteroaryl group.

7. The heterocyclic compound of claim 1, wherein $Ar_1$ and $Ar_2$ in Formula 1 are each independently a substituted or unsubstituted $C_1$-$C_{20}$ alkyl group, a substituted or unsubstituted $C_5$-$C_{20}$ aryl group, or a substituted or unsubstituted $C_3$-$C_{20}$ heteroaryl group.

8. The heterocyclic compound of claim 1, wherein $Ar_1$ and $Ar_2$ in Formula 1 are each independently a group represented by one of Formulae 4a to 4d below:

formula 4a

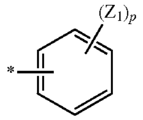

formula 4b

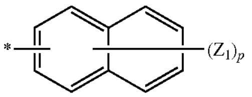

formula 4c

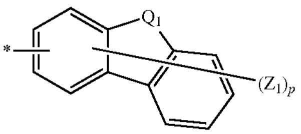

formula 4d

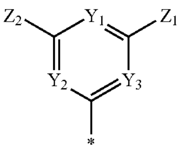

wherein, in Formula 4a to 4d, $Q_1$ is a linking group represented by —$C(R_6)(R_7)$—, —$N(R_6)$—, —S—, or —O—;

$Y_1$, $Y_2$, and $Y_3$ are each independently a linking group represented by —N= or —$C(R_8)$=;

$Z_1$, $Z_2$, $R_6$, $R_7$, and $R_8$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group;

p is an integer from 1 to 8; and

* indicates a binding site.

9. The heterocyclic compound of claim 1, wherein $Ar_1$ and $Ar_2$ in Formula 1 are each independently a group represented by one of Formulae 5a to 5i below:

formula 5a

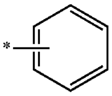

formula 5b

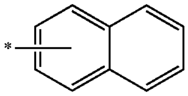

formula 5c

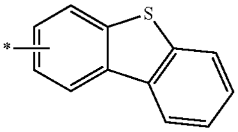

formula 5d

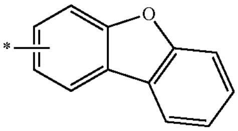

formula 5e

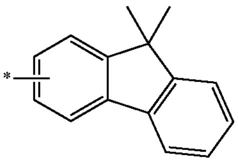

formula 5f

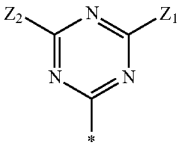

formula 5g

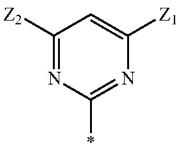

formula 5h

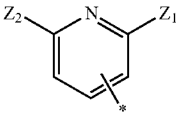

-continued formula 5i

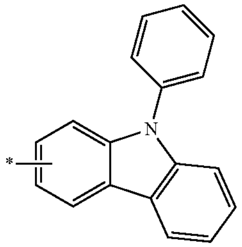

wherein $Z_1$ and $Z_2$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, or a substituted or unsubstituted $C_6$-$C_{20}$ condensed polycyclic group; and * indicates a binding site.

10. The heterocyclic compound of claim 1, wherein $Ar_3$ for X in Formula 1 is a substituted or unsubstituted $C_5$-$C_{20}$ arylene group, a substituted or unsubstituted $C_3$-$C_{20}$ heteroarylene group, or a substituted or unsubstituted $C_6$-$C_{20}$ condensed polycyclic group.

11. The heterocyclic compound of claim 1, wherein $Ar_3$ for X in Formula 1 comprises a group represented by one of Formulae 6a to 6e below:

formula 6a

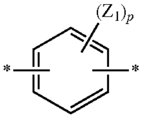

formula 6b

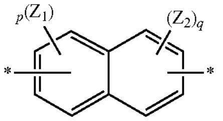

formula 6c

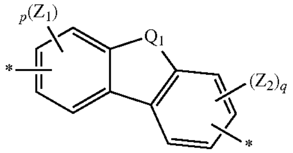

formula 6d

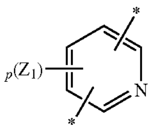

formula 6e

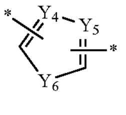

wherein, in Formula 6a to 6e, $Q_1$ is a linking group represented by —$C(R_6)(R_7)$—, —$N(R_6)$—, or —S—;

$Y_4$, $Y_5$, and $Y_6$ are each independently a linking group represented by —N= or —$C(R_8)$=, —S—, or —O—;

$Z_1$, $Z_2$, $R_6$, $R_7$, and $R_8$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group;

p is an integer from 1 to 8;

q is an integer from 1 to 8; and

* indicates a binding site.

12. The heterocyclic compound of claim 1, wherein n is 1 or 2.

13. The heterocyclic compound of claim 1, wherein X in Formula 1 comprises a group represented by one of Formulae 7a to 7j:

forlmua 7a

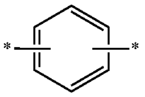

forlmua 7b

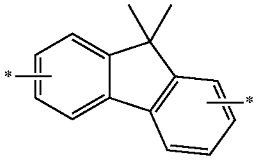

forlmua 7c

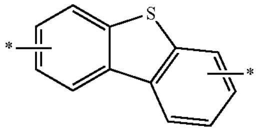

forlmua 7d

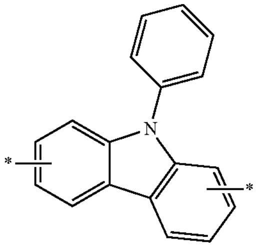

forlmua 7e

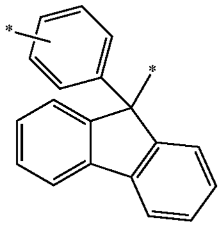

forlmua 7f

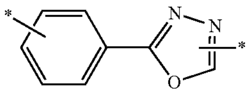

forlmua 7g

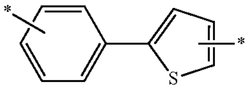

forlmua 7h

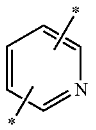

-continued forlmua 7i

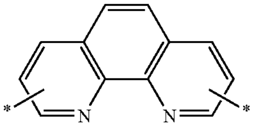

forlmua 7j

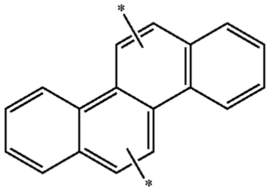

wherein, in Formula 7a to 7j, * indicates a binding site.

14. The heterocyclic compound of claim 1, wherein $R_1$, $R_3$, and $R_4$ in Formula 1 are each independently a hydrogen atom, a deuterium atom, a halogen atom, a cyano group, a methyl group, an ethyl group, a propyl group, a butyl group, a pentyl group, or groups represented by Formulae 3a to 3l below:

formula 3a

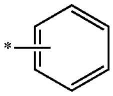

formula 3b

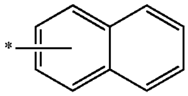

formula 3c

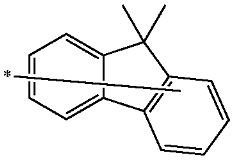

formula 3d

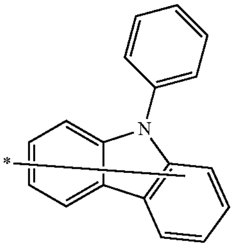

formula 3e

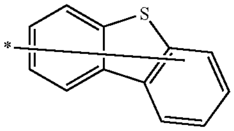

formula 3f

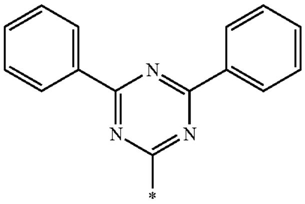

-continued formula 3g

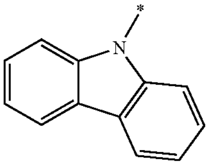

formula 3h

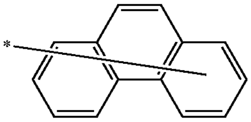

formula 3i

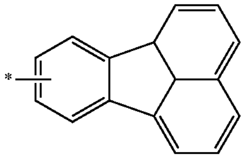

formula 3j

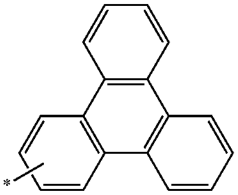

formula 3k

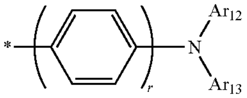

formula 3l

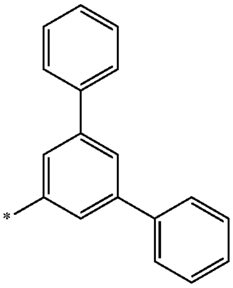

wherein, in Formula 3a to 3l, $Ar_{12}$ and $Ar_{13}$ are each independently an unsubstituted aryl group, a substituted or unsubstituted $C_3$-$C_{20}$ heteroaryl group, or a substituted or unsubstituted $C_6$-$C_{20}$ condensed polycyclic group; r is an integer from 0 to 2, and * indicates a binding site;

$R_2$ and $R_5$ are hydrogen atoms;

$Ar_3$ comprises a group represented by one of Formulae 6a to 6e below:

formula 6a

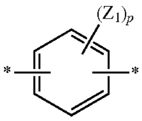

-continued formula 6b

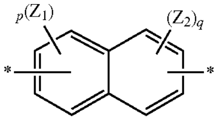

formula 6c

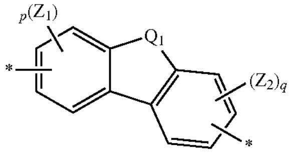

formula 6d

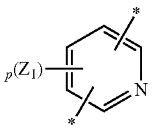

formula 6e

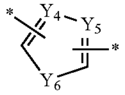

wherein, in Formulae 6a to 6e, $Q_1$ is a linking group represented by —C($R_6$)($R_7$)—, —N($R_6$)—, or —S—; $Y_4$, $Y_5$ and $Y_6$ are each independently a linking group represented by —N═, —C($R_8$)═, —S—, or —O—; $Z_1$, $Z_2$, $R_6$, $R_7$, and $R_8$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group; p is an integer from 1 to 8; q is an integer from 1 to 8; and * indicates a binding site;

n in Formula 1 is 1 or 2; and $Ar_1$ and $Ar_2$ are each independently selected from among groups represented by Formulae 4a to 4d below:

formula 4a

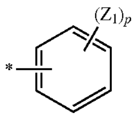

formula 4b

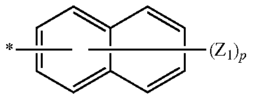

formula 4c

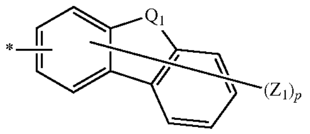

formula 4d

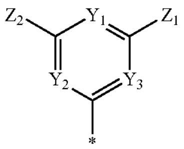

wherein, in Formulae 4a to 4d, $Q_1$ is a linking group represented by —C($R_6$)($R_7$)—, —N($R_6$)—, —S—, or —O—; $Y_1$, $Y_2$ and $Y_3$ are each independently a linking group represented by —N═ or —C($R_8$)═; $Z_1$, $Z_2$, $R_6$, $R_7$, and $R_8$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxy group; p is an integer from 1 to 8; and * indicates a binding site.

15. The heterocyclic compound of claim 1, comprising one of the compounds below:

2

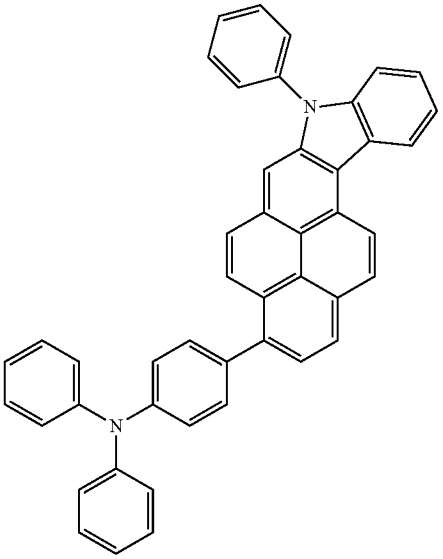

11

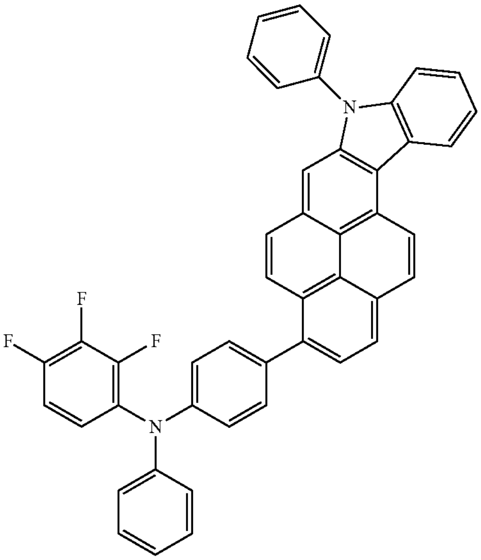

-continued
24
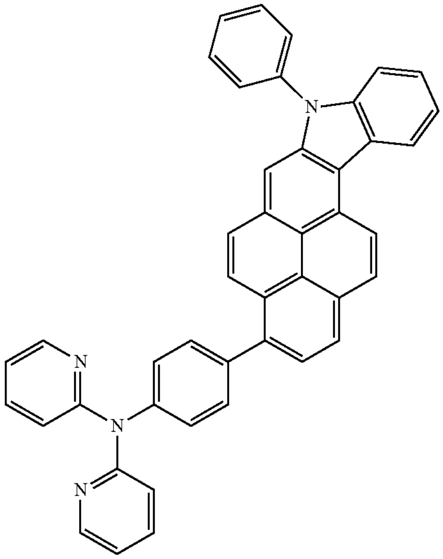
34
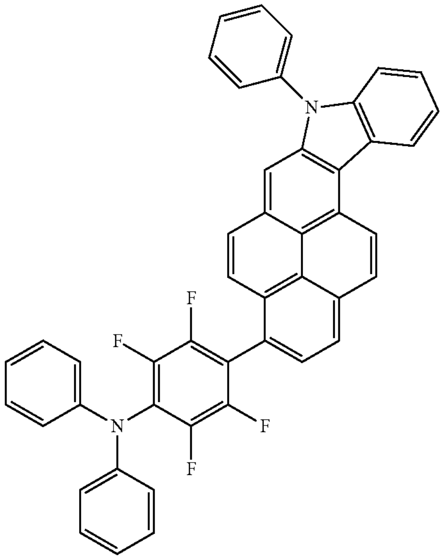
-continued
45
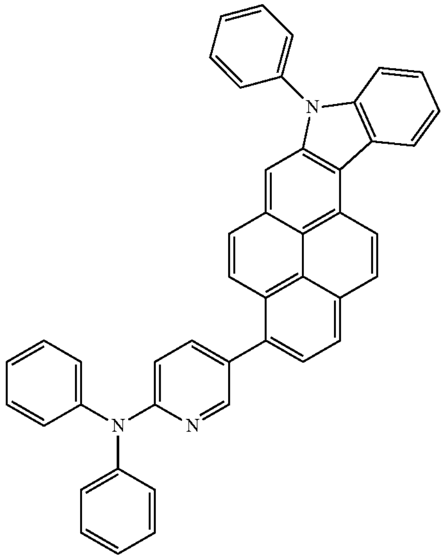
48
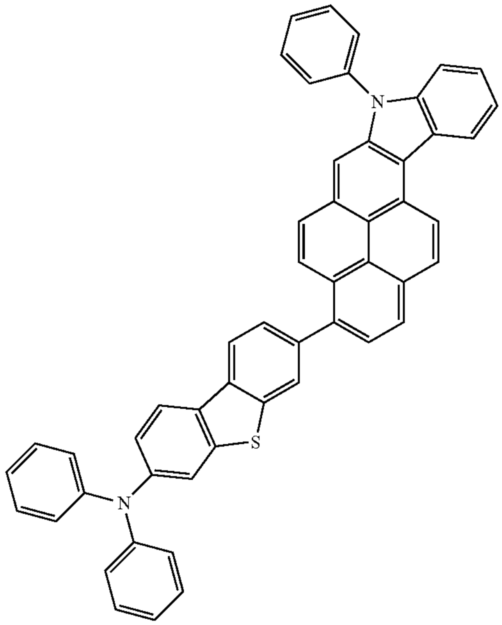

-continued

55

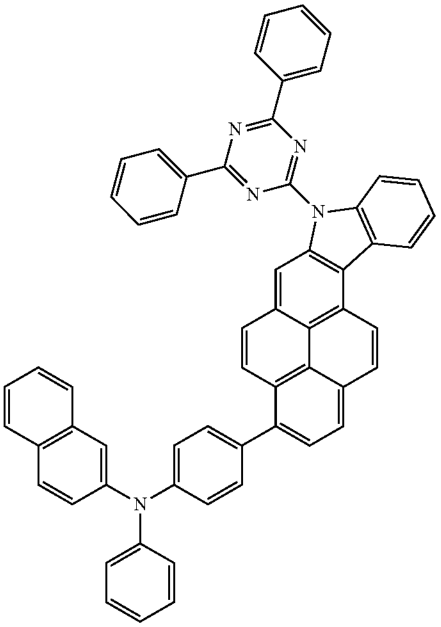

57

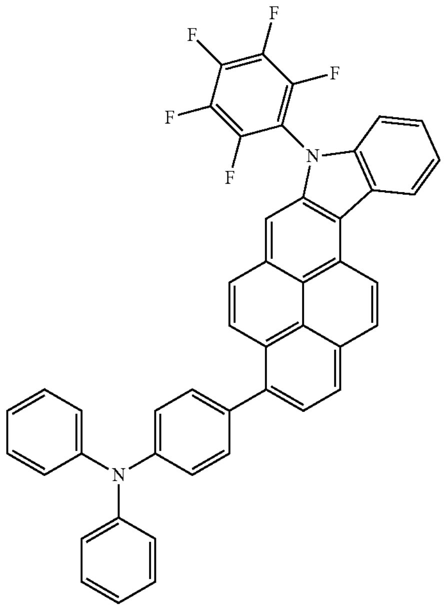

-continued

73

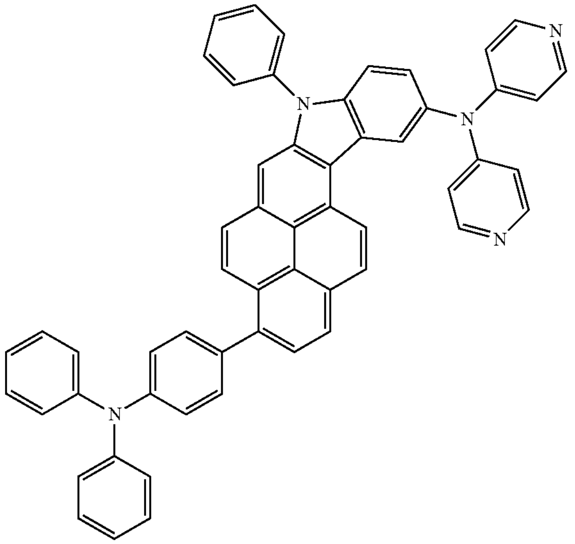

82

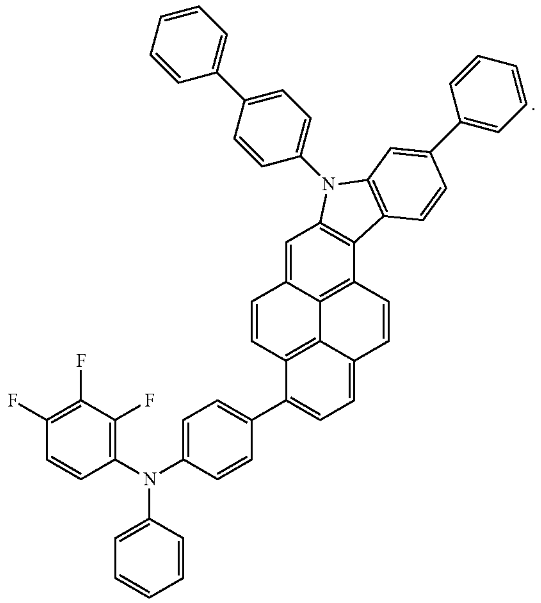

16. An organic light-emitting device comprising:

a first electrode;

a second electrode; and an organic layer between the first electrode and the second electrode, wherein the organic layer comprises a first layer comprising the heterocyclic compound of claim 1.

17. The organic light-emitting device of claim 16, wherein the first layer comprises at least one layer, a hole injection layer, a hole transport layer, a functional layer having both hole injection and hole transport capabilities, an electron injection layer, an electron transport layer, a functional layer having both electron injection and electron transport capabilities or any combination thereof.

18. The organic light-emitting device of claim 16, wherein the first layer comprises an emission layer, and the heterocyclic compound of Formula 1 is used in the emission layer as a host or a dopant for a fluorescent or phosphorescent device.

19. The organic light-emitting device of claim 16, wherein the first layer comprises an emission layer, and the emission layer comprises an anthracene compound, an arylamine compound, or a styryl compound.

20. The organic light-emitting device of claim 16, wherein the first layer comprises an emission layer, and a red layer, a green layer, a blue layer, or a white layer of the emission layer comprises a phosphorescent compound.

21. The organic light-emitting device of claim 16, wherein the first layer comprises a blue emission layer.

22. The organic light-emitting device of claim 16, wherein the first layer comprises a blue emission layer; and the heterocyclic compound of Formula 1 is used as a blue dopant.

23. The organic light-emitting device of claim 16, wherein the organic layer further comprises a hole injection layer, a hole transport layer, a functional layer having hole injecting and transporting capabilities, an emission layer, a hole blocking layer, an electron transport layer, an electron injecting layer, or a combination of two or more layers thereof.

24. The organic light-emitting device of claim 23, at least one layer selected from the hole injection layer, the hole transport layer, or the functional layer having hole injecting and transporting capabilities further comprises a charge-generating material.

25. The organic light-emitting device of claim 23, wherein the electron transport layer of the organic light-emitting device comprises an electron transporting organic material and a metal-containing material.

26. The organic light-emitting device of claim 25, wherein the metal-containing material comprises a Li complex.

27. The organic light-emitting device of claim 16, wherein the first layer is formed by using a wetting process by using the heterocyclic compound of claim 1.

28. A flat panel display device comprising the organic light-emitting device of claim 16, wherein the first electrode of the organic light-emitting device is electrically connected to a source electrode or a drain electrode of a thin-film transistor.

* * * * *